United States Patent
Nakazawa et al.

(10) Patent No.: US 10,590,287 B2
(45) Date of Patent: Mar. 17, 2020

(54) CHARGE-TRANSPORTING VARNISH AND ORGANIC ELECTROLUMINESCENT ELEMENT

(71) Applicant: NISSAN CHEMICAL INDUSTRIES, LTD., Tokyo (JP)

(72) Inventors: Taichi Nakazawa, Funabashi (JP); Toshiyuki Endo, Funabashi (JP); Yuki Takayama, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/736,370

(22) PCT Filed: Jun. 10, 2016

(86) PCT No.: PCT/JP2016/067306
§ 371 (c)(1),
(2) Date: Dec. 14, 2017

(87) PCT Pub. No.: WO2016/204079
PCT Pub. Date: Dec. 22, 2016

(65) Prior Publication Data
US 2018/0163061 A1    Jun. 14, 2018

(30) Foreign Application Priority Data
Jun. 15, 2015  (JP) .................. 2015-120202

(51) Int. Cl.
*H01B 1/00* (2006.01)
*C09D 5/24* (2006.01)
(Continued)

(52) U.S. Cl.
CPC ............... *C09D 5/24* (2013.01); *C07B 43/06* (2013.01); *C07C 13/567* (2013.01); *C07C 25/13* (2013.01);
(Continued)

(58) Field of Classification Search
CPC ......... C09D 5/24; C07B 43/06; C07C 13/567; C07C 25/13; C07C 233/75; C07C 233/80;
(Continued)

(56) References Cited

U.S. PATENT DOCUMENTS

2010/0230639 A1  9/2010 Yamada et al.
2012/0295904 A1  11/2012 Zhi et al.
(Continued)

FOREIGN PATENT DOCUMENTS

CN      101215379 A  *  7/2008
JP      49-128933 A      12/1974
(Continued)

OTHER PUBLICATIONS

Tanaka et al. "Novel Fluorine-containing Poly(aryl ether amide)s derived from 2,3,4,5,6-Pentafluorobenzoic Acid". vol. 62, No. 7. pp. 155-161. (Year: 2006).*
(Continued)

*Primary Examiner* — Mark Kopec
(74) *Attorney, Agent, or Firm* — Birch, Stewart, Kolasch & Birch, LLP

(57) ABSTRACT

Provided is a charge-transporting varnish which comprises an amide compound containing fluorine atoms and represented by formula (1) and a charge-transporting substance.

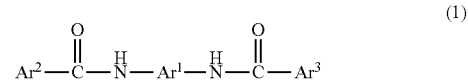

[In the formula, $Ar^1$ represents a group represented by any of formulae (1-1) to (1-9) and $Ar^2$ and $Ar^3$ each represent a given fluorinated aryl or aralkyl group.]

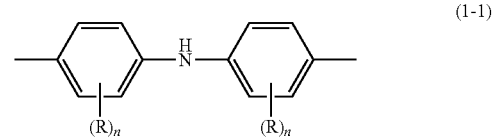

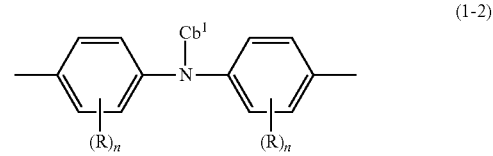

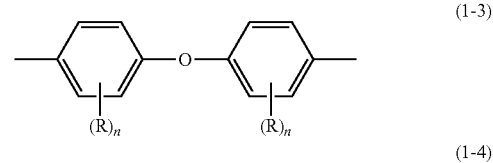

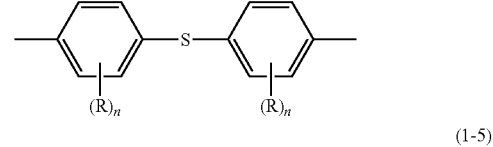

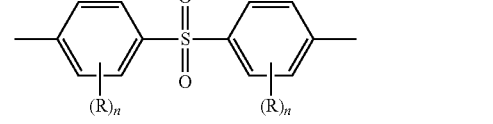

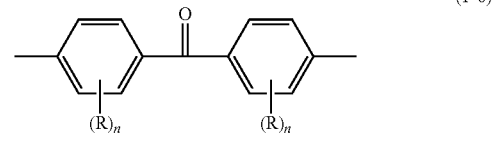

(Continued)

-continued

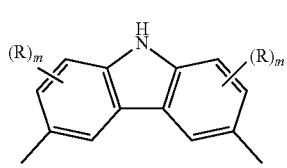

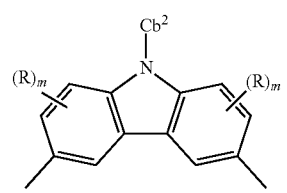

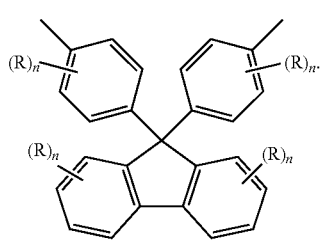

15 Claims, No Drawings

(51) Int. Cl.
| | | |
|---|---|---|
| C07C 233/00 | (2006.01) | |
| C07C 233/75 | (2006.01) | |
| C07D 209/88 | (2006.01) | |
| C07C 233/80 | (2006.01) | |
| H01L 51/50 | (2006.01) | |
| H01B 1/12 | (2006.01) | |
| C07B 43/06 | (2006.01) | |
| C07C 13/567 | (2006.01) | |
| C07C 25/13 | (2006.01) | |

(52) U.S. Cl.
CPC .......... *C07C 233/75* (2013.01); *C07C 233/80* (2013.01); *C07D 209/88* (2013.01); *H01B 1/121* (2013.01); *H01L 51/50* (2013.01); *C07C 2603/18* (2017.05); *H01L 51/506* (2013.01)

(58) Field of Classification Search
CPC ... C07C 2603/18; C07D 209/88; H01L 51/50; H01L 51/506; H01B 1/12; H01B 1/121
USPC ........................................................ 252/500
See application file for complete search history.

(56) References Cited

U.S. PATENT DOCUMENTS

| | | |
|---|---|---|
| 2014/0148548 A1 | 5/2014 | Yamanaka et al. |
| 2014/0227815 A1 | 8/2014 | Nakaie et al. |
| 2015/0053892 A1 | 2/2015 | Takeda et al. |

FOREIGN PATENT DOCUMENTS

| | | |
|---|---|---|
| JP | 53-35579 B | 9/1978 |
| JP | 2008-27646 A | 2/2008 |
| JP | 2008-78181 A | 4/2008 |
| JP | 2013-507446 A | 3/2013 |
| WO | WO 2008/069812 A1 | 6/2008 |
| WO | WO 2008/129947 A1 | 10/2008 |
| WO | WO 2011/046954 A1 | 4/2011 |
| WO | WO 2013/042623 A1 | 3/2013 |
| WO | WO 2013/129249 A1 | 9/2013 |
| WO | WO 2014/084188 A1 | 6/2014 |

OTHER PUBLICATIONS

International Search Report for PCT/JP2016/067306 dated Aug. 30, 2016.
Tanaka et al., "Novel Fluorine-containing Poly(aryl ether amide)s derived from 2,3,4,5,6-Pentafluorobenzoic Acid", SEN'I GAKKAISHI, 2006, vol. 62, No. 7, pp. 155-161.
Written Opinion of the International Searching Authority for PCT/JP2016/067306 (PCT/ISA/237) dated Aug. 30, 2016.

\* cited by examiner

CHARGE-TRANSPORTING VARNISH AND ORGANIC ELECTROLUMINESCENT ELEMENT

TECHNICAL FIELD

The present invention relates to a charge-transporting varnish and an organic electroluminescent (EL) device.

BACKGROUND ART

Organic EL devices are expected to see practical application in such fields as displays and lighting. Various research is being carried out on materials and device structures with the aim of achieving such properties as low-voltage driving, high brightness and good longevity.

A plurality of functional thin films are used in organic EL devices, one of which, the hole-injecting layer, is responsible for transferring charge between an anode and a hole-transporting layer or a light-emitting layer, and thus serves an important function in achieving low-voltage driving and high brightness in organic EL devices.

Processes for forming the hole-injecting layer are broadly divided into dry processes such as vapor deposition and wet processes such as spin coating. On comparing these processes, wet processes are better able to efficiently produce thin films having a high flatness over a large surface area. Therefore, particularly in the field of displays, wet processes are often used not only in the formation of the hole-injecting layer, but also in the formation of upper layers such as the hole-transporting layer and the light-emitting layer (see, for example, Patent Document 1).

In view of the above, the inventors have developed various charge-transporting varnishes that contain an aniline derivative as the charge-transporting substance (see, for example, Patent Documents 2 and 3). However, improvements continue to be desired in the wet process materials used to form the hole-injecting layer.

In particular, in order to be able to contribute to the brightness characteristics of the organic EL device, there is a desire for a higher uniformity not only in the hole-injecting layer, but also in the hole-transporting layer (see, for example, Patent Document 4). Hence, there exists a desire for a material which gives a charge-transporting thin film of excellent flatness and which, moreover, enables an excellent coatability to be achieved when forming a hole-transporting layer or light-emitting layer on this film by a wet process.

PRIOR ART DOCUMENTS

Patent Documents

Patent Document 1: JP-A 2008-78181
Patent Document 2: WO 2008/129947
Patent Document 3: WO 2013/042623
Patent Document 4: JP-A 2008-27646
Patent Document 5: WO 2011/046954
Patent Document 6: JP-B S53-035579
Patent Document 7: CN-A 101215379

Non-Patent Documents

Non-Patent Document 1: Sen'i Gakkaishi Vol. 62(2006), 62(7), pp. 155-161.

SUMMARY OF THE INVENTION

Problems to be Solved by the Invention

It is therefore an object of this invention to provide a charge-transporting varnish that is capable of giving a thin film which has a high flatness and a high charge transportability, which is excellent also in terms of the coatability thereon of upper layer materials, and which, when employed in an organic EL device, exhibits excellent brightness characteristics.

Means for Solving the Problems

The inventors have conducted extensive investigations in order to attain the above object, as a result of which they have discovered that, by using a charge-transporting substance and a given fluorine atom-containing amide compound, a thin film can be produced which has excellent flatness, charge transportability and coatability thereon of upper layer materials, and also that when this thin-film is used in an organic EL device, good initial characteristics and longevity characteristics can be achieved. Fluorine atom-containing amide compounds that can be used in this invention are mentioned in Patent Documents 5 to 7 and Non-Patent Document 1. However, the language in these documents neither teaches nor suggests in any way the specific arrangement of the present invention and the actions and effects particular to this invention.

Accordingly, the invention provides the following charge-transporting varnish and organic EL device.

1. A charge-transporting varnish comprising a fluorine atom-containing amide compound of formula (1) below and a charge-transporting substance,

[Chemical Formula 1]

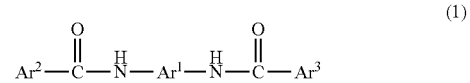

wherein $Ar^1$ is a group of any of formulas (1-1) to (1-9) below,

[Chemical Formula 2]

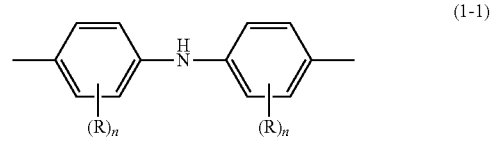

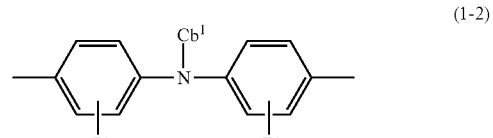

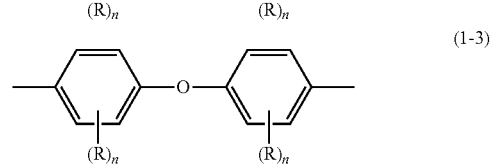

-continued

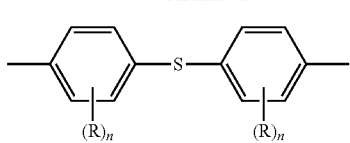 (1-4)

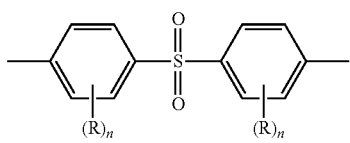 (1-5)

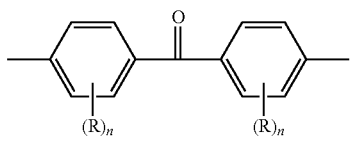 (1-6)

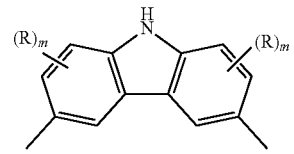 (1-7)

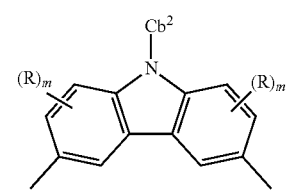 (1-8)

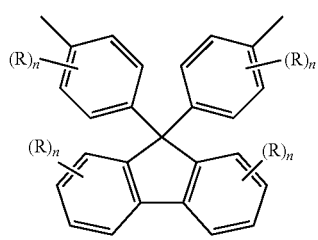 (1-9)

wherein each R is independently a cyano group, a nitro group, a halogen atom, an alkyl group of 1 to 20 carbon atoms or a haloalkyl group of 1 to 20 carbon atoms, $Cb^1$ and $Cb^1$ each are independently an alkyl group of 1 to 20 carbon atoms or an aryl group of 6 to 20 carbon atoms, n is an integer from 0 to 4, and m is an integer from 0 to 3; and $Ar^2$ and $Ar^3$ are each independently a fluoroaryl group of 6 to 20 carbon atoms which may be substituted with a cyano group, a chlorine atom, a bromine atom, an iodine to atom, a nitro group, an alkyl group of 1 to 20 carbon atoms, a fluoroalkyl group of 1 to 20 carbon atoms or a fluoroalkoxy group of 1 to 20 carbon atoms; an aryl group of 6 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms; a fluoroaralkyl group of 7 to 20 carbon atoms which may be substituted with a cyano group, a chlorine atom, a bromine atom, an iodine atom, a nitro group, a fluoroalkoxy group of 1 to 20 carbon atoms, a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms; or an aralkyl group of 7 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms.

2. The charge-transporting varnish of 1 above, wherein $Ar^2$ and $Ar^3$ are each independently a fluoroaryl group of 6 to 20 carbon atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or an aryl group of 6 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms.

3. The charge-transporting varnish of 2 above, wherein $Ar^2$ and $Ar^3$ are each independently a phenyl group which is substituted with three or more fluorine atoms and may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or a 2-(trifluoromethyl)phenyl, 3-(trifluoromethyl)phenyl, 4-(trifluoromethyl)phenyl, 4-ethoxy-3-(trifluoromethyl)phenyl, 3-fluoro-4-trifluoromethylphenyl, 4-fluoro-3-trifluoromethylphenyl, 4-fluoro-2-trifluoromethylphenyl, 2-fluoro-5-(trifluoromethyl)phenyl, 3-fluoro-5-(trifluoromethyl)phenyl, 3,5-di(trifluoromethyl)phenyl, 2,4,6-tri(trifluoromethyl)phenyl, 4-(pentafluoroethyl)phenyl, 4-(3,3,3-trifluoropropyl)phenyl, 2,3,5,6-tetrafluoro-4-trifluoromethylphenyl, 4-(perfluorovinyl)phenyl, 4-(perfluoropropenyl)phenyl or 4-(perfluorobutenyl)phenyl group.

4. The charge-transporting varnish of any of 1 to 3 above, wherein $Ar^2$ and $Ar^3$ are identical groups.

5. The charge-transporting varnish of any of 1 to 4 above, wherein n and m are both 0.

6. The charge-transporting varnish of any of 1 to 5 above, wherein $Ar^1$ is a group of formula (1-1), (1-2), (1-3), (1-7) or (1-9).
7. The charge-transporting varnish of any of 1 to 6 above, further comprising a dopant.
8. A charge-transporting thin film produced using the charge-transporting varnish of any of 1 to 7 above.
9. An organic EL device comprising the charge-transporting thin film of 8 above.
10. A fluorine atom-containing amide compound of formula (1') below,

[Chemical Formula 3]

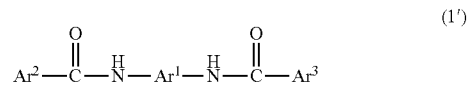
(1')

wherein $Ar^1$, $Ar^2$ and $Ar^3$ are the same as above, exclusive of combinations that represent fluorine atom-containing amide compounds of any of formulas (K1) to (K18) below.

[Chemical Formula 4]

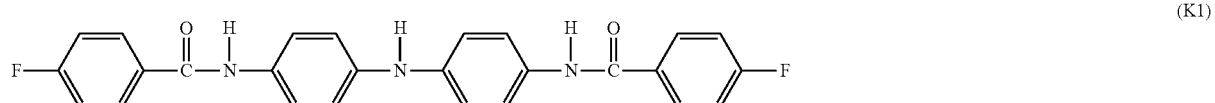
(K1)

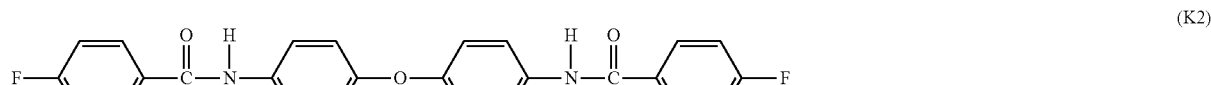
(K2)

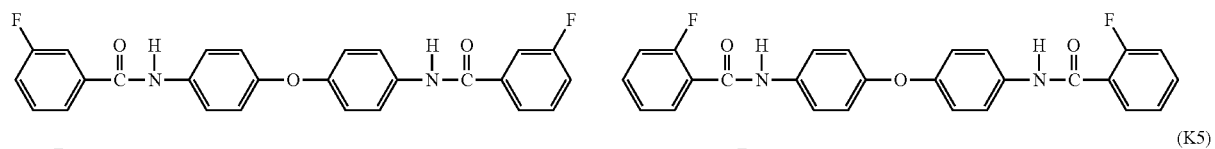
(K3) (K4)

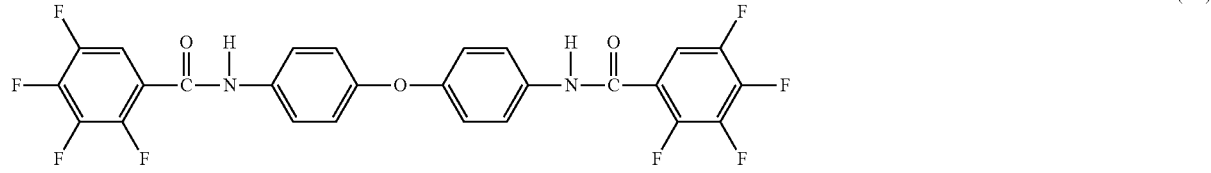
(K5) (K6) (K7)

[Chemical Formula 5]

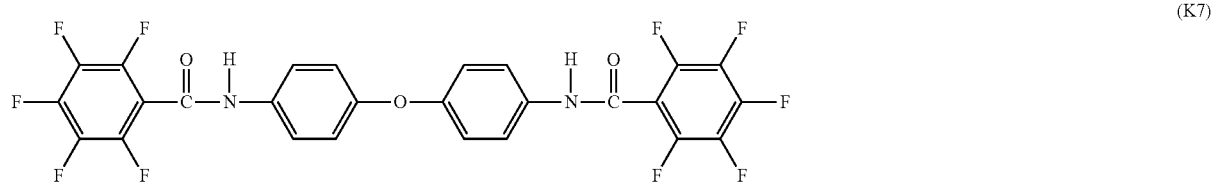
(K8) (K9)

-continued
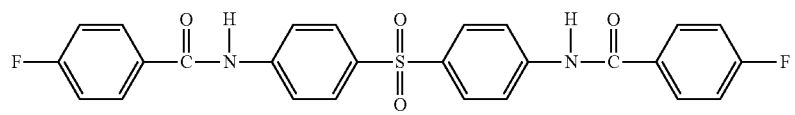
(K10)
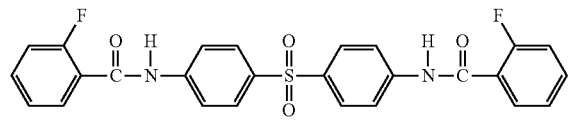
(K11)
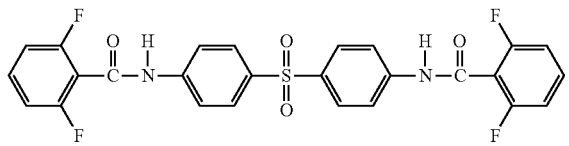
(K12)
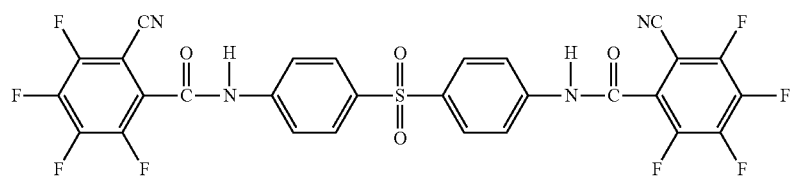
(K13)
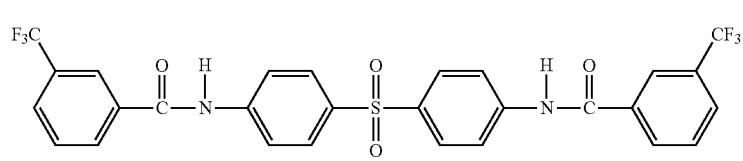
(K14)
[Chemical Formula 6]
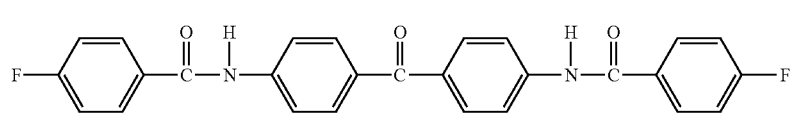
(K15)
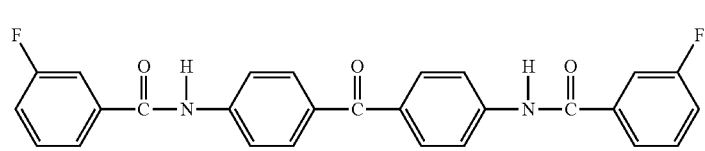
(K16)
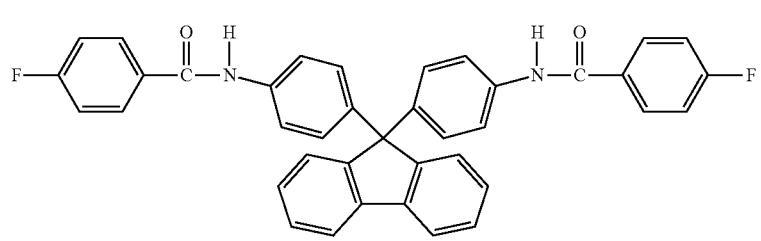
(K17)
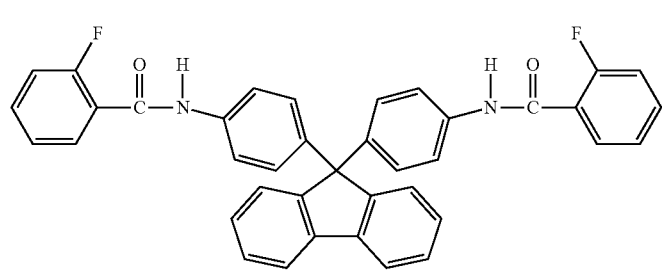
(K18)

11. The fluorine atom-containing amide compound of 10 above, wherein $Ar^2$ and $Ar^3$ are each independently a fluoroaryl group of 6 to 20 carbon atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or an aryl group of 6 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms.

12. The fluorine atom-containing amide compound of 11 above, wherein $Ar^2$ and $Ar^3$ are each independently a phenyl group which is substituted with three or more fluorine atoms and may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or a 2-(trifluoromethyl)phenyl, 3-(trifluoromethyl)phenyl, 4-(trifluoromethyl)phenyl, 4-ethoxy-3-(trifluoromethyl)phenyl, 3-fluoro-4-trifluoromethylphenyl, 4-fluoro-3-trifluoromethylphenyl, 4-fluoro-2-trifluoromethylphenyl, 2-fluoro-5-(trifluoromethyl)phenyl, 3-fluoro-5-(trifluoromethyl)phenyl, 3,5-di(trifluoromethyl)phenyl, 2,4,6-tri(trifluoromethyl)phenyl, 4-(pentafluoroethyl)phenyl, 4-(3,3,3-trifluoropropyl)phenyl, 2,3,5,6-tetrafluoro-4-trifluoromethylphenyl, 4-(perfluorovinyl)phenyl, 4-(perfluoropropenyl)phenyl or 4-(perfluorobutenyl)phenyl group.

13. The fluorine atom-containing amide compound of any of 10 to 12 above, wherein $Ar^2$ and $Ar^3$ are identical groups.

14. The fluorine atom-containing amide compound of any of 10 to 13 above, wherein n and m are both 0.

15. The fluorine atom-containing amide compound of any of 10 to 14 above, wherein $Ar^1$ is a group of formula (1-1), (1-2), (1-3), (1-7) or (1-9).

Advantageous Effects of the Invention

The thin film produced from the charge-transporting varnish of the invention has a very high charge transportability. As a result, it can be advantageously used as a thin film in organic EL devices and other electronic devices. In particular, by employing this thin film as a hole-injecting layer in an organic EL device, it is possible to obtain organic EL devices of excellent brightness characteristics and longevity characteristics.

The charge-transporting varnish of the invention can reproducibly produce thin films having excellent charge transportability, even using various wet processes capable of film formation over a large area, such as spin coating and slit coating, and moreover maintains a high wettability by solvents used in upper layer materials on the surface of the thin film. Hence, the inventive charge-transporting varnish is capable of fully accommodating recent advances in the field of organic EL devices.

EMBODIMENT FOR CARRYING OUT THE INVENTION

[Charge-Transporting Varnish]

The charge-transporting varnish of the invention includes a given fluorine atom-containing amide compound and a charge-transporting substance. In this invention, "charge transportability" is synonymous with electrical conductivity, and is also synonymous with hole transportability. The charge-transporting varnish may itself have charge transportability, or a solid film obtained using the varnish may have charge transportability.

[Fluorine Atom-Containing Amide Compound]

The fluorine atom-containing amide compound has formula (1) below.

[Chemical Formula 7]

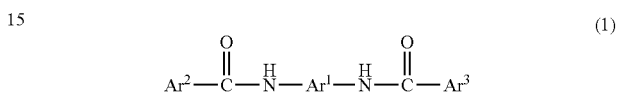

(1)

In formula (1), $Ar^1$ is a group of any of formulas (1-1) to (1-9) below.

[Chemical Formula 8]

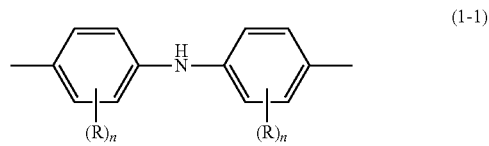

(1-1)

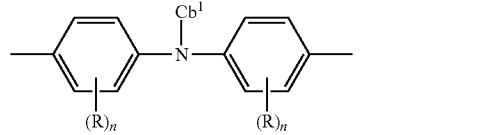

(1-2)

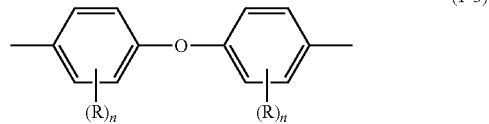

(1-3)

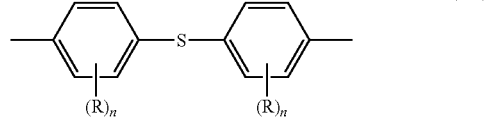

(1-4)

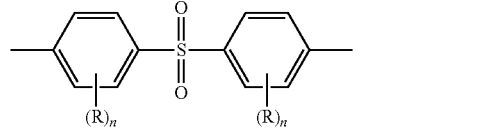

(1-5)

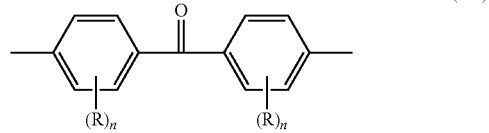

(1-6)

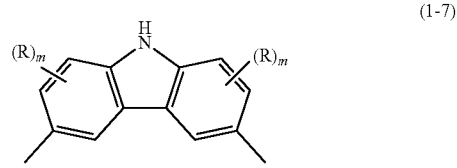

(1-7)

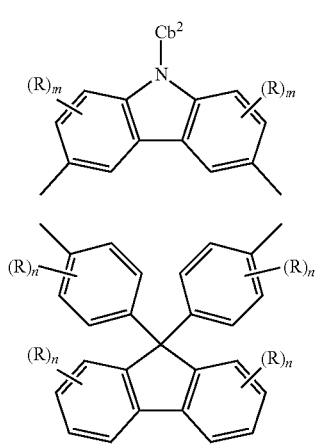

In these formulas, each R is independently a cyano group, a nitro group, a halogen atom, an alkyl group of 1 to 20 carbon atoms or a haloalkyl group of 1 to 20 carbon atoms. $Cb^1$ and $Cb^2$ are each independently an alkyl group of 1 to 20 carbon atoms or an aryl group of 6 to 20 carbon atoms. Also, n is an integer from 0 to 4, and m is an integer from 0 to 3.

The halogen atom is exemplified by fluorine, chlorine, bromine and iodine atoms.

The alkyl group of 1 to 20 carbon atoms may be linear, branched or cyclic. Examples include linear or branched alkyl groups of 1 to 20 carbon atoms, such as methyl, ethyl, n-propyl, isopropyl, n-butyl, isobutyl, s-butyl, t-butyl, n-pentyl, n-hexyl, n-heptyl, n-octyl, n-nonyl and n-decyl groups; and cyclic alkyl groups of 3 to 20 carbon atoms, such as cyclopropyl, cyclobutyl, cyclopentyl, cyclohexyl, cycloheptyl, cyclooctyl, cyclononyl, cyclodecyl, bicyclobutyl, bicyclopentyl, bicyclohexyl, bicycloheptyl, bicyclooctyl, bicyclononyl and bicyclodecyl groups.

Examples of aryl groups of 6 to 20 carbon atoms include phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups.

Taking into consideration the ease of synthesizing the fluorine atom-containing amide compound and the availability of the starting materials, it is preferable for n and m to each be independently 0 or 1, and more preferable for both to be 0. When n or m is 1 or more, R is preferably an alkyl group of 1 to 10 carbon atoms, and more preferably an alkyl group of 1 to 4 carbon atoms.

$Cb^1$ and $Cb^2$ are each preferably an alkyl group of 1 to 10 carbon atoms or an aryl group of 6 to 14 carbon atoms; more preferably an alkyl group of 1 to 4 carbon atoms, a phenyl group, a 1-naphthyl group or a 2-naphthyl group; and even more preferably a methyl or ethyl group.

$Ar^1$ is preferably a group of formula (1-1), (1-2), (1-3), (1-7) or (1-9), and more preferably a group of formula (1-1), (1-2), (1-7) or (1-9).

In formula (1), $Ar^2$ and $Ar^3$ are each independently a fluoroaryl group of 6 to 20 carbon atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; an aryl group of 6 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms; a fluoroaralkyl group of 7 to 20 carbon atoms which may be substituted with a cyano group, a chlorine atom, a bromine atom, an iodine atom, a nitro group, a fluoroalkoxy group of 1 to 20 carbon atoms, a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms; or an aralkyl group of 7 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms.

The fluoroaryl group is not particularly limited, provided that it is an aryl group in which at least one hydrogen atom on a carbon atom is substituted with a fluorine atom. Examples include 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 3,4,5-trifluorophenyl, 2,3,4,5-tetrafluorophenyl, 2,3,4,6-tetrafluorophenyl, 2,3,5,6-tetrafluorophenyl, pentafluorophenyl, 2-fluoro-1-naphthyl, 3-fluoro-1-naphthyl, 4-fluoro-1-naphthyl, 6-fluoro-1-naphthyl, 7-fluoro-1-naphthyl, 8-fluoro-1-naphthyl, 4,5-difluoro-1-naphthyl, 5,7-difluoro-1-naphthyl, 5,8-difluoro-1-naphthyl, 5,6,7,8-tetrafluoro-1-naphthyl, heptafluoro-1-naphthyl, 1-fluoro-2-naphthyl, 5-fluoro-2-naphthyl, 6-fluoro-2-naphthyl, 7-fluoro-2-naphthyl, 5-7-difluoro-2-naphthyl and heptafluoro-2-naphthyl groups.

Taking into account the balance between, for example, the solubility of the fluorine atom-containing amide compound in organic solvents and the availability of starting materials for the fluorine atom-containing amide compound, the fluoroaryl group is preferably a phenyl group which is substituted with three or more fluorine atoms and which may be substituted with a cyano group, chlorine atom, bromine atom, iodine atom, nitro group, alkyl group of 1 to 20 carbon atoms, fluoroalkyl group of 1 to 20 carbon atoms or fluoroalkoxy group of 1 to 20 carbon atoms.

The aryl group of 6 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms and may be additionally substituted with a cyano group, a halogen atom or a fluoroalkoxy group of 1 to 20 carbon atoms (which aryl group is also referred to below, for the sake of convenience, as "the substituted aryl group") is not particularly limited so long as it is an aryl group in which at least one hydrogen atom on a carbon atom is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms. Examples include 2-(trifluoromethyl)phenyl, 3-(trifluoromethyl)phenyl, 4-(trifluoromethyl)phenyl, 4-ethoxy-3-(trifluoromethyl)phenyl, 3-fluoro-4-trifluoromethylphenyl, 4-fluoro-3-trifluoromethylphenyl, 4-fluoro-2-trifluoromethylphenyl, 2-fluoro-5-(trifluoromethyl)phenyl, 3-fluoro-5-(trifluoromethyl)phenyl, 3,5-di(trifluoromethyl)phenyl, 2,4,6-tri(trifluoromethyl)phenyl, 4-(pentafluoroethyl)phenyl, 4-(3,3,3-trifluoropropyl)phenyl, 2,3,5,6-tetrafluoro-4-trifluoromethylphenyl, 4-(perfluorovinyl)phenyl, 4-(perfluoropropenyl)phenyl and 4-(perfluorobutenyl)phenyl groups.

Taking into account the balance between, for example, the solubility of the fluorine atom-containing amide compound in organic solvents and the availability of starting materials for the fluorine atom-containing amide compound, the substituted aryl group is preferably a phenyl group which is substituted with a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms and which may be additionally substituted with a cyano group, a halogen atom or a fluoroalkoxy group of 1 to 20 carbon atoms (which phenyl group is also referred to below, for the sake of convenience, as "the substituted phenyl group"), more preferably a phenyl group substituted with from 1 to 3 trifluoromethyl groups, and even more preferably a p-trifluoromethylphenyl group.

The fluoroaralkyl group is not particularly limited, provided it is an aralkyl group in which at least one hydrogen atom on a carbon atom is substituted with a fluorine atom. Examples include 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2,3,4-trifluorobenzyl, 2,3,5-trifluorobenzyl, 2,3,6-trifluorobenzyl, 2,4,5-trifluorobenzyl, 2,4,6-trifluorobenzyl, 2,3,4,5-tetrafluorobenzyl, 2,3,4,6-tetrafluorobenzyl, 2,3,5,6-tetrafluorobenzyl and 2,3,4,5,6-pentafluorobenzyl groups.

The aralkyl group of 7 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms and which may be substituted with a cyano group, a halogen atom or a fluoroalkoxy group of 1 to 20 carbon atoms is not particularly limited, provided it is an aralkyl group in which at least one hydrogen atom on a carbon atom is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms. Examples include 2-trifluoromethylbenzyl, 3-trifluoromethylbenzyl, 4-trifluoromethylbenzyl, 2,4-di(trifluoromethyl)benzyl, 2,5-di(trifluoromethyl)benzyl, 2,6-di(trifluoromethyl)benzyl, 3,5-di(trifluoromethyl)benzyl and 2,4,6-tri(trifluoromethyl)benzyl groups.

The fluoroalkyl group is not particularly limited, provided it is a linear or branched alkyl group in which at least one hydrogen atom on a carbon atom is substituted with a fluorine atom. Examples include fluoromethyl, difluoromethyl, trifluoromethyl, 1-fluoroethyl, 2-fluoroethyl, 1,2-difluoroethyl, 1,1-difluoroethyl, 2,2-difluoroethyl, 1,1,2-trifluoroethyl, 1,2,2-trifluoroethyl, 2,2,2-trifluoroethyl, 1,1,2,2-tetrafluoroethyl, 1,2,2,2-tetrafluoroethyl, 1,1,2,2,2-pentafluoroethyl, 1-fluoropropyl, 2-fluoropropyl, 3-fluoropropyl, 1,1-difluoropropyl, 1,2-difluoropropyl, 1,3-difluoropropyl, 2,2-difluoropropyl, 2,3-difluoropropyl, 3,3-difluoropropyl, 1,1,2-trifluoropropyl, 1,1,3-trifluoropropyl, 1,2,3-trifluoropropyl, 1,3,3-trifluoropropyl, 2,2,3-trifluoropropyl, 2,3,3-trifluoropropyl, 3,3,3-trifluoropropyl, 1,1,2,2-tetrafluoropropyl, 1,1,2,3-tetrafluoropropyl, 1,2,2,3-tetrafluoropropyl, 1,3,3,3-tetrafluoropropyl, 2,2,3,3-tetrafluoropropyl, 2,3,3,3-tetrafluoropropyl, 1,1,2,2,3-pentafluoropropyl, 1,2,2,3,3-pentafluoropropyl, 1,1,3,3,3-pentafluoropropyl, 1,2,3,3,3-pentafluoropropyl, 2,2,3,3,3-pentafluoropropyl and heptafluoropropyl groups.

The fluoroalkoxy group is not particularly limited, provided it is an alkoxy group in which at least one hydrogen atom on a carbon atom is substituted with a fluorine atom. Examples include fluoromethoxy, difluoromethoxy, trifluoromethoxy, 1-fluoroethoxy, 2-fluoroethoxy, 1,2-difluoroethoxy, 1,1-difluoroethoxy, 2,2-difluoroethoxy, 1,1,2-trifluoroethoxy, 1,2,2-trifluoroethoxy, 2,2,2-trifluoroethoxy, 1,1,2,2-tetrafluoroethoxy, 1,2,2,2-tetrafluoroethoxy, 1,1,2,2,2-pentafluoroethoxy, 1-fluoropropoxy, 2-fluoropropoxy, 3-fluoropropoxy, 1,1-difluoropropoxy, 1,2-difluoropropoxy, 1,3-difluoropropoxy, 2,2-difluoropropoxy, 2,3-difluoropropoxy, 3,3-difluoropropoxy, 1,1,2-trifluoropropoxy, 1,1,3-trifluoropropoxy, 1,2,3-trifluoropropoxy, 1,3,3-trifluoropropoxy, 2,2,3-trifluoropropoxy, 2,3,3-trifluoropropoxy, 3,3,3-trifluoropropoxy, 1,1,2,2-tetrafluoropropoxy, 1,1,2,3-tetrafluoropropoxy, 1,2,2,3-tetrafluoropropoxy, 1,3,3,3-tetrafluoropropoxy, 2,2,3,3-tetrafluoropropoxy, 2,3,3,3-tetrafluoroporpoxy, 1,1,2,2,3-pentafluoropropoxy, 1,2,2,3,3-pentafluoropropoxy, 1,1,3,3,3-pentafluoropropoxy, 1,2,3,3,3-pentafluoropropoxy, 2,2,3,3,3-pentafluoropropoxy and heptafluoropropoxy groups.

The fluorocycloalkyl group is not particularly limited, provided it is a cycloalkyl group in which at least one hydrogen atom on a carbon atom is substituted with a fluorine atom. Examples include 1-fluorocyclopropyl, 2-fluorocyclopropyl, 2,2-difluorocyclopropyl, 2,2,3,3-tetrafluorocyclopropyl, pentafluorocyclopropyl, 2,2-difluorocyclobutyl, 2,2,3,3-tetrafluorocyclobutyl, 2,2,3,3,4,4-hexafluorocyclobutyl, heptafluorocyclobutyl, 1-fluorocyclopentyl, 3-fluorocyclopentyl, 3,3-difluorocyclopentyl, 3,3,4,4-tetrafluorocyclopentyl, nonafluorocyclopentyl, 1-fluorocyclohexyl, 2-fluorocyclohexyl, 4-fluorocyclohexyl, 4,4-difluorocyclohexyl, 2,2,3,3-tetrafluorocyclohexyl, 2,3,4,5,6-pentafluorocyclohexyl and undecafluorocyclohexyl groups.

The fluorobicycloalkyl group is not particularly limited, provided it is a bicycloalkyl group in which at least one hydrogen atom on a carbon atom is substituted with a fluorine atom. Examples include 3-fluorobicyclo[1.1.0]butan-1-yl, 2,2,4,4-tetrafluorobicyclo[1.1.0]butan-1-yl, pentafluorobicyclo[1.1.0]butan-1-yl, 3-fluorobicyclo[1.1.1]pentan-1-yl, 2,2,4,4,5-pentafluorobicyclo[1.1.1]pentan-1-yl, 2,2,4,4,5,5-hexafluorobicyclo[1.1.1.]pentan-1-yl, 5-fluorobicyclo[3.1.0]hexan-6-yl, 6-fluorobicyclo[3.1.0]hexan-6-yl, 6,6-difluorobicyclo[3.1.0]hexan-2-yl, 2,2,3,3,5,5,6,6-octafluorobicyclo[2.2.0]hexan-1-yl, 1-fluorobicyclo[2.2.1]heptan-2-yl, 3-fluorobicyclo[2.2.1]heptan-2-yl, 4-fluorobicyclo[2.2.1]heptan-1-yl, 5-fluorobicyclo[3.1.1]heptan-1-yl, 1,3,3,4,5,5,6,6,7,7-decafluorobicyclo[2.2.1]heptan-2-yl, undecafluorobicyclo[2.2.1]heptan-2-yl, 3-fluorobicyclo[2.2.2]octan-1-yl and 4-fluorobicyclo[2.2.2]octan-1-yl groups.

The fluoroalkenyl group is not particularly limited, provided it is an alkenyl group in which at least one hydrogen atom on a carbon atom is substituted with a fluorine atom. Examples include 1-fluoroethenyl, 2-fluoroethenyl, 1,2-difluoroethenyl, 1,2,2-trifluoroethenyl, 2,3,3-trifluoro-1-propenyl, 3,3,3-trifluoro-1-propenyl, 2,3,3,3-tetrafluoro-1-propenyl, pentafluoro-1-propenyl, 1-fluoro-2-propenyl, 1,1-difluoro-2-propenyl, 2,3-difluoro-2-propenyl, 3,3-difluoro-2-propenyl, 2,3,3-trifluoro-2-propenyl, 1,2,3,3-tetrafluoro-2-propenyl and pentafluoro-2-propenyl groups.

The fluoroalkynyl group is not particularly limited, provided it is an alkynyl group in which at least one hydrogen atom on a carbon atom is substituted with a fluorine atom. Examples include fluoroethynyl, 3-fluoro-1-propynyl, 3,3-difluoro-1-propynyl, 3,3,3-trifluoro-1-propynyl, 1-fluoro-2-propynyl and 1,1-difluoro-2-propynyl groups.

Of these, $Ar^2$ and $Ar^3$ are preferably the above fluoroaryl groups of 6 to 20 carbon atoms which may be substituted or the above substituted aryl groups, more preferably the above fluorophenyl groups which may be substituted or the above substituted phenyl groups, and even more preferably the above trifluorophenyl groups which may be substituted, the above tetrafluorophenyl groups which may be substituted, the above pentafluorophenyl groups which may be substituted or a phenyl group substituted with one to three trifluoromethyl groups. From the standpoint of the ease of synthesizing the fluorine atom-containing amide compound, $Ar^2$ and $Ar^3$ are preferably identical groups.

Specific examples of groups preferred as $Ar^2$ and $Ar^3$ include, but are not limited to, the following.

[Chemical Formula 9]

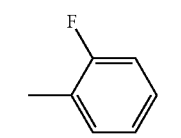 (A1)

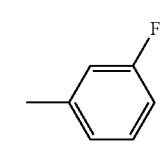 (A2)

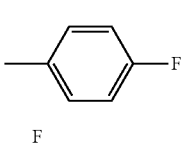 (A3)

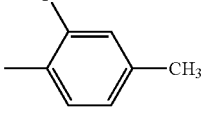 (A4)

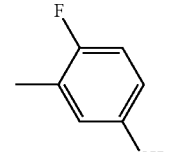 (A5)

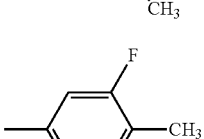 (A6)

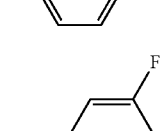 (A7)

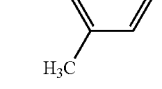 (A8)

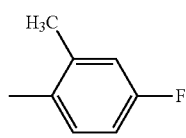 (A9)

[Chemical Formula 10]

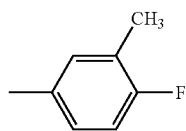 (A10)

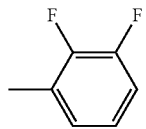 (A11)

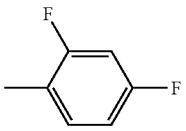 (A12)

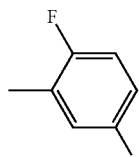 (A13)

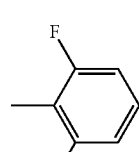 (A14)

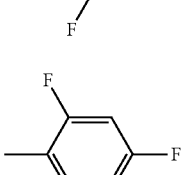 (A15)

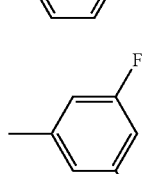 (A16)

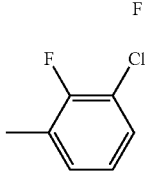 (A17)

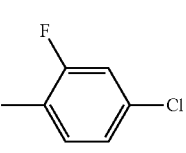

[Chemical Formula 11]

(A37) 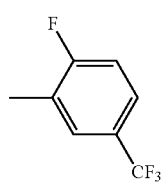
(A38) 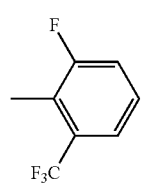
(A39) 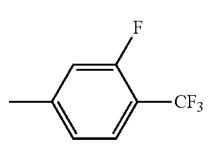
(A40) 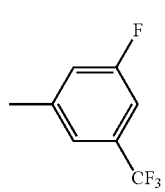
(A41) 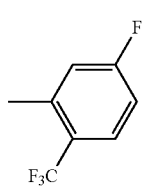
(A42) 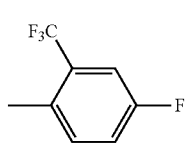
(A43) 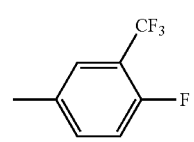
[Chemical Formula 12]
(A44) 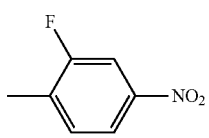
(A45) 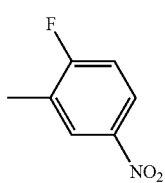
(A46) 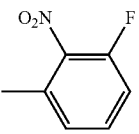
(A47) 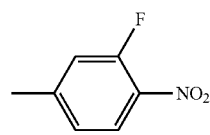
(A48) 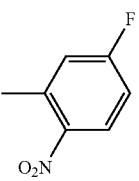
(A49) 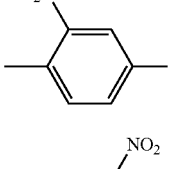
(A50) 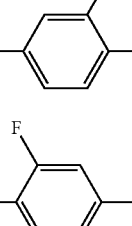
(A51) 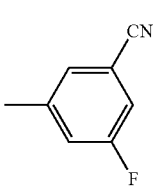
(A52) 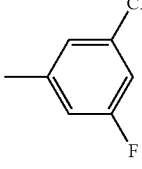
[Chemical Formula 13]
(A53) 
(A54) 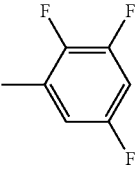
(A55) 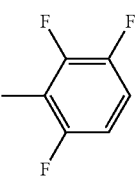

-continued
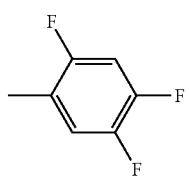 (A56)
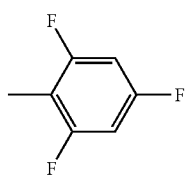 (A57)
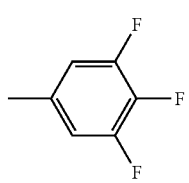 (A58)
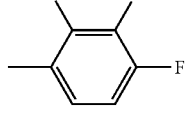 (A59)
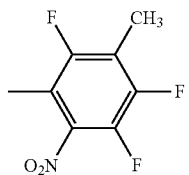 (A60)
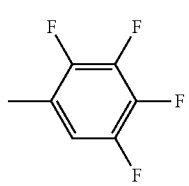 (A61)
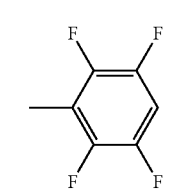 (A62)
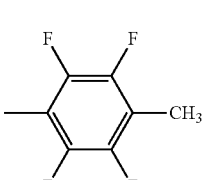 (A63)
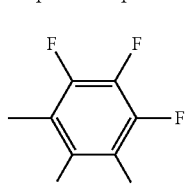 (A64)
-continued
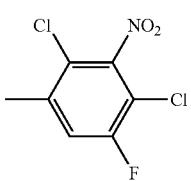 (A65)
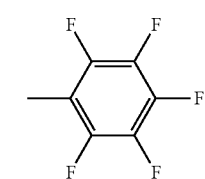 (A66)
[Chemical Formula 14]
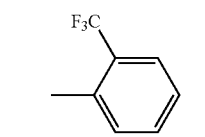 (A67)
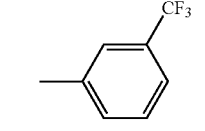 (A68)
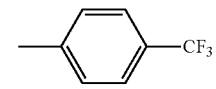 (A69)
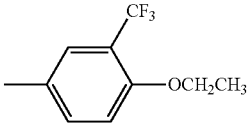 (A70)
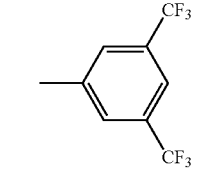 (A71)
 (A72)
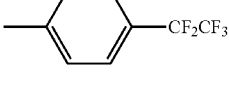 (A73)

In this invention, preferred examples of the fluorine atom-containing amide compound of formula (1) include those of formula (1').

[Chemical Formula 15]

$$Ar^2-\overset{O}{\underset{\|}{C}}-\overset{H}{\underset{|}{N}}-Ar^1-\overset{H}{\underset{|}{N}}-\overset{O}{\underset{\|}{C}}-Ar^3 \quad (1')$$

In this formula, $Ar^1$ to $Ar^3$ are the same as above, exclusive of combinations that represent fluorine atom-containing amide compounds of any of formulas (K1) to (K18) below.

[Chemical Formula 17]
(K8)
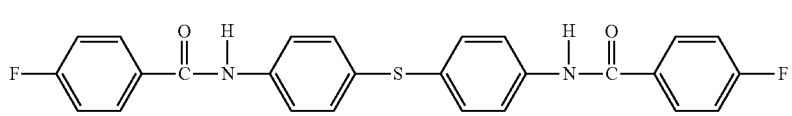
(K9)
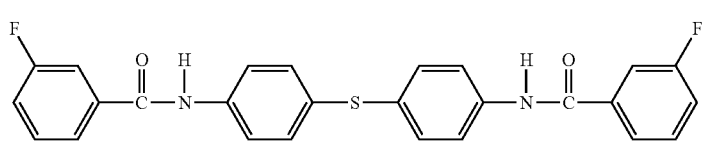
(K10)
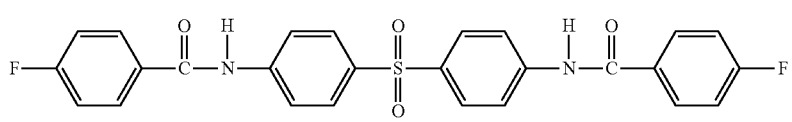
(K11)
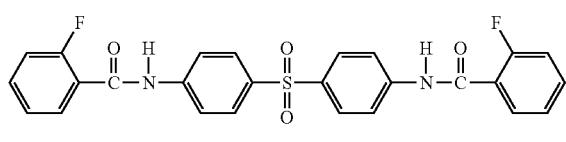
(K12)
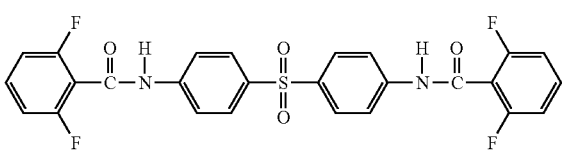
(K13)
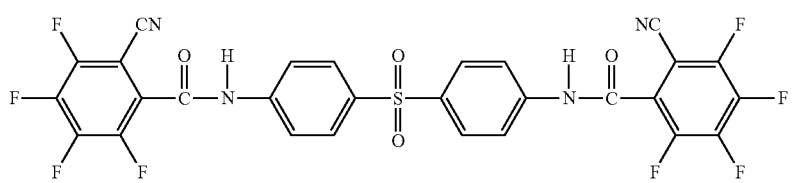
(K14)
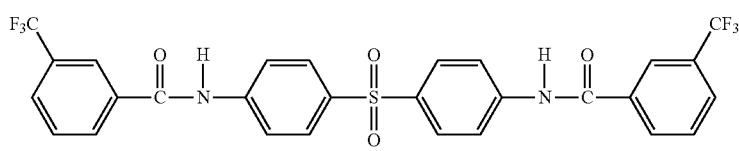
[Chemical Formula 18]
(K15)
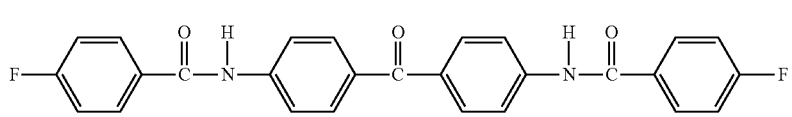
(K16)
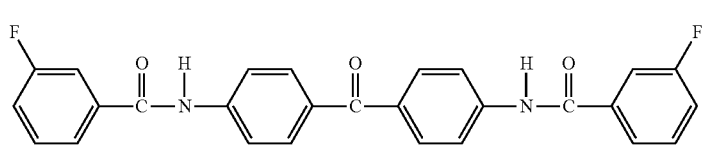
(K17)
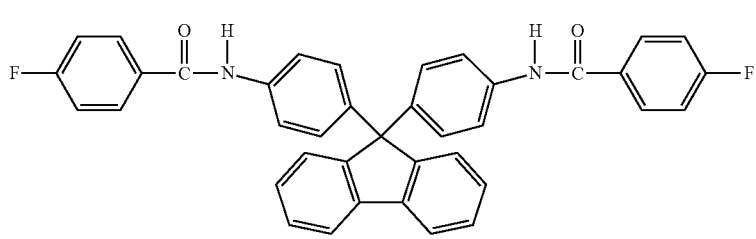

-continued (K18)

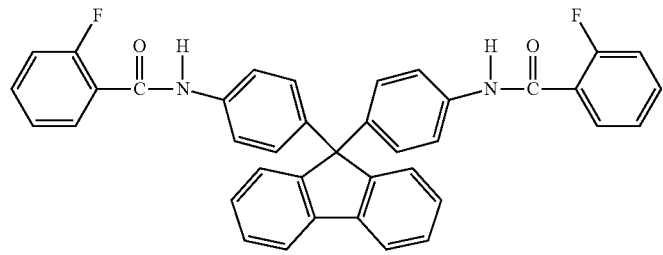

Substituents, preferred substituents and the like in formula (1') are exemplified in the same way as in formula (1).

Illustrative examples of the amide compound of formula (1) include, but are not limited to, those shown below. In the tables, $Ar^1$, n, m, $Cb^1$, $Cb^2$, $Ar^2$ and $Ar^3$ represent specific entities in formula (1) for the compounds shown on the respective lines of the table. For example, the compound of formula (E1-61) and the compound of formula (E7-61) are respectively as follows.

[Chemical Formula 19]

(E1-61)

(E7-61)

TABLE 1

| Compound | $Ar^1$ | n | $Ar^2$ | $Ar^3$ |
|---|---|---|---|---|
| (E1-1) | (1-1) | 0 | (A1) | (A1) |
| (E1-2) | (1-1) | 0 | (A2) | (A2) |
| (E1-3) | (1-1) | 0 | (A3) | (A3) |
| (E1-4) | (1-1) | 0 | (A4) | (A4) |
| (E1-5) | (1-1) | 0 | (A5) | (A5) |
| (E1-6) | (1-1) | 0 | (A6) | (A6) |
| (E1-7) | (1-1) | 0 | (A7) | (A7) |
| (E1-8) | (1-1) | 0 | (A8) | (A8) |
| (E1-9) | (1-1) | 0 | (A9) | (A9) |
| (E1-10) | (1-1) | 0 | (A10) | (A10) |
| (E1-11) | (1-1) | 0 | (A11) | (A11) |
| (E1-12) | (1-1) | 0 | (A12) | (A12) |
| (E1-13) | (1-1) | 0 | (A13) | (A13) |
| (E1-14) | (1-1) | 0 | (A14) | (A14) |
| (E1-15) | (1-1) | 0 | (A15) | (A15) |
| (E1-16) | (1-1) | 0 | (A16) | (A16) |
| (E1-17) | (1-1) | 0 | (A17) | (A17) |
| (E1-18) | (1-1) | 0 | (A18) | (A18) |
| (E1-19) | (1-1) | 0 | (A19) | (A19) |
| (E1-20) | (1-1) | 0 | (A20) | (A20) |

TABLE 1-continued

| Compound | $Ar^1$ | n | $Ar^2$ | $Ar^3$ |
|---|---|---|---|---|
| (E1-21) | (1-1) | 0 | (A21) | (A21) |
| (E1-22) | (1-1) | 0 | (A22) | (A22) |
| (E1-23) | (1-1) | 0 | (A23) | (A23) |
| (E1-24) | (1-1) | 0 | (A24) | (A24) |
| (E1-25) | (1-1) | 0 | (A25) | (A25) |
| (E1-26) | (1-1) | 0 | (A26) | (A26) |
| (E1-27) | (1-1) | 0 | (A27) | (A27) |
| (E1-28) | (1-1) | 0 | (A28) | (A28) |
| (E1-29) | (1-1) | 0 | (A29) | (A29) |
| (E1-30) | (1-1) | 0 | (A30) | (A30) |
| (E1-31) | (1-1) | 0 | (A31) | (A31) |
| (E1-32) | (1-1) | 0 | (A32) | (A32) |
| (E1-33) | (1-1) | 0 | (A33) | (A33) |
| (E1-34) | (1-1) | 0 | (A34) | (A34) |
| (E1-35) | (1-1) | 0 | (A35) | (A35) |
| (E1-36) | (1-1) | 0 | (A36) | (A36) |
| (E1-37) | (1-1) | 0 | (A37) | (A37) |
| (E1-38) | (1-1) | 0 | (A38) | (A38) |
| (E1-39) | (1-1) | 0 | (A39) | (A39) |
| (E1-40) | (1-1) | 0 | (A40) | (A40) |
| (E1-41) | (1-1) | 0 | (A41) | (A41) |
| (E1-42) | (1-1) | 0 | (A42) | (A42) |
| (E1-43) | (1-1) | 0 | (A43) | (A43) |
| (E1-44) | (1-1) | 0 | (A44) | (A44) |
| (E1-45) | (1-1) | 0 | (A45) | (A45) |
| (E1-46) | (1-1) | 0 | (A46) | (A46) |
| (E1-47) | (1-1) | 0 | (A47) | (A47) |
| (E1-48) | (1-1) | 0 | (A48) | (A48) |
| (E1-49) | (1-1) | 0 | (A49) | (A49) |
| (E1-50) | (1-1) | 0 | (A50) | (A50) |
| (E1-51) | (1-1) | 0 | (A51) | (A51) |
| (E1-52) | (1-1) | 0 | (A52) | (A52) |
| (E1-53) | (1-1) | 0 | (A53) | (A53) |
| (E1-54) | (1-1) | 0 | (A54) | (A54) |
| (E1-55) | (1-1) | 0 | (A55) | (A55) |
| (E1-56) | (1-1) | 0 | (A56) | (A56) |
| (E1-57) | (1-1) | 0 | (A57) | (A57) |
| (E1-58) | (1-1) | 0 | (A58) | (A58) |
| (E1-59) | (1-1) | 0 | (A59) | (A59) |
| (E1-60) | (1-1) | 0 | (A60) | (A60) |
| (E1-61) | (1-1) | 0 | (A61) | (A61) |
| (E1-62) | (1-1) | 0 | (A62) | (A62) |
| (E1-63) | (1-1) | 0 | (A63) | (A63) |
| (E1-64) | (1-1) | 0 | (A64) | (A64) |
| (E1-65) | (1-1) | 0 | (A65) | (A66) |
| (E1-66) | (1-1) | 0 | (A66) | (A66) |
| (E1-67) | (1-1) | 0 | (A67) | (A67) |
| (E1-68) | (1-1) | 0 | (A68) | (A68) |
| (E1-69) | (1-1) | 0 | (A69) | (A69) |
| (E1-70) | (1-1) | 0 | (A70) | (A70) |
| (E1-71) | (1-1) | 0 | (A71) | (A71) |
| (E1-72) | (1-1) | 0 | (A72) | (A72) |
| (E1-73) | (1-1) | 0 | (A73) | (A73) |
| (E1-74) | (1-1) | 0 | (A74) | (A74) |
| (E1-75) | (1-1) | 0 | (A75) | (A75) |
| (E1-76) | (1-1) | 0 | (A76) | (A76) |
| (E1-77) | (1-1) | 0 | (A77) | (A77) |

TABLE 2

| Compound | Ar¹ | n | Cb¹ | Ar² | Ar³ |
|---|---|---|---|---|---|
| (E2-1) | (1-2) | 0 | Me | (A1) | (A1) |
| (E2-2) | (1-2) | 0 | Me | (A2) | (A2) |
| (E2-3) | (1-2) | 0 | Me | (A3) | (A3) |
| (E2-4) | (1-2) | 0 | Me | (A4) | (A4) |
| (E2-5) | (1-2) | 0 | Me | (A5) | (A5) |
| (E2-6) | (1-2) | 0 | Me | (A6) | (A6) |
| (E2-7) | (1-2) | 0 | Me | (A7) | (A7) |
| (E2-8) | (1-2) | 0 | Me | (A8) | (A8) |
| (E2-9) | (1-2) | 0 | Me | (A9) | (A9) |
| (E2-10) | (1-2) | 0 | Me | (A10) | (A10) |
| (E2-11) | (1-2) | 0 | Me | (A11) | (A11) |
| (E2-12) | (1-2) | 0 | Me | (A12) | (A12) |
| (E2-13) | (1-2) | 0 | Me | (A13) | (A13) |
| (E2-14) | (1-2) | 0 | Me | (A14) | (A14) |
| (E2-15) | (1-2) | 0 | Me | (A15) | (A15) |
| (E2-16) | (1-2) | 0 | Me | (A16) | (A16) |
| (E2-17) | (1-2) | 0 | Me | (A17) | (A17) |
| (E2-18) | (1-2) | 0 | Me | (A18) | (A18) |
| (E2-19) | (1-2) | 0 | Me | (A19) | (A19) |
| (E2-20) | (1-2) | 0 | Me | (A20) | (A20) |
| (E2-21) | (1-2) | 0 | Me | (A21) | (A21) |
| (E2-22) | (1-2) | 0 | Me | (A22) | (A22) |
| (E2-23) | (1-2) | 0 | Me | (A23) | (A23) |
| (E2-24) | (1-2) | 0 | Me | (A24) | (A24) |
| (E2-25) | (1-2) | 0 | Me | (A25) | (A25) |
| (E2-26) | (1-2) | 0 | Me | (A26) | (A26) |
| (E2-27) | (1-2) | 0 | Me | (A27) | (A27) |
| (E2-28) | (1-2) | 0 | Me | (A28) | (A28) |
| (E2-29) | (1-2) | 0 | Me | (A29) | (A29) |
| (E2-30) | (1-2) | 0 | Me | (A30) | (A30) |
| (E2-31) | (1-2) | 0 | Me | (A31) | (A31) |
| (E2-32) | (1-2) | 0 | Me | (A32) | (A32) |
| (E2-33) | (1-2) | 0 | Me | (A33) | (A33) |
| (E2-34) | (1-2) | 0 | Me | (A34) | (A34) |
| (E2-35) | (1-2) | 0 | Me | (A35) | (A35) |
| (E2-36) | (1-2) | 0 | Me | (A36) | (A36) |
| (E2-37) | (1-2) | 0 | Me | (A37) | (A37) |
| (E2-38) | (1-2) | 0 | Me | (A38) | (A38) |
| (E2-39) | (1-2) | 0 | Me | (A39) | (A39) |
| (E2-40) | (1-2) | 0 | Me | (A40) | (A40) |
| (E2-41) | (1-2) | 0 | Me | (A41) | (A41) |
| (E2-42) | (1-2) | 0 | Me | (A42) | (A42) |
| (E2-43) | (1-2) | 0 | Me | (A43) | (A43) |
| (E2-44) | (1-2) | 0 | Me | (A44) | (A44) |
| (E2-45) | (1-2) | 0 | Me | (A45) | (A45) |
| (E2-46) | (1-2) | 0 | Me | (A46) | (A46) |
| (E2-47) | (1-2) | 0 | Me | (A47) | (A47) |
| (E2-48) | (1-2) | 0 | Me | (A48) | (A48) |
| (E2-49) | (1-2) | 0 | Me | (A49) | (A49) |
| (E2-50) | (1-2) | 0 | Me | (A50) | (A50) |
| (E2-51) | (1-2) | 0 | Me | (A51) | (A51) |
| (E2-52) | (1-2) | 0 | Me | (A52) | (A52) |
| (E2-53) | (1-2) | 0 | Me | (A53) | (A53) |
| (E2-54) | (1-2) | 0 | Me | (A54) | (A54) |
| (E2-55) | (1-2) | 0 | Me | (A55) | (A55) |
| (E2-56) | (1-2) | 0 | Me | (A56) | (A56) |
| (E2-57) | (1-2) | 0 | Me | (A57) | (A57) |
| (E2-58) | (1-2) | 0 | Me | (A58) | (A58) |
| (E2-59) | (1-2) | 0 | Me | (A59) | (A59) |
| (E2-60) | (1-2) | 0 | Me | (A60) | (A60) |
| (E2-61) | (1-2) | 0 | Me | (A61) | (A61) |
| (E2-62) | (1-2) | 0 | Me | (A62) | (A62) |
| (E2-63) | (1-2) | 0 | Me | (A63) | (A63) |
| (E2-64) | (1-2) | 0 | Me | (A64) | (A64) |
| (E2-65) | (1-2) | 0 | Me | (A65) | (A65) |
| (E2-66) | (1-2) | 0 | Me | (A66) | (A66) |
| (E2-67) | (1-2) | 0 | Me | (A67) | (A67) |
| (E2-68) | (1-2) | 0 | Me | (A68) | (A68) |
| (E2-69) | (1-2) | 0 | Me | (A69) | (A69) |
| (E2-70) | (1-2) | 0 | Me | (A70) | (A70) |
| (E2-71) | (1-2) | 0 | Me | (A71) | (A71) |
| (E2-72) | (1-2) | 0 | Me | (A72) | (A72) |
| (E2-73) | (1-2) | 0 | Me | (A73) | (A73) |
| (E2-74) | (1-2) | 0 | Me | (A74) | (A74) |
| (E2-75) | (1-2) | 0 | Me | (A75) | (A75) |
| (E2-76) | (1-2) | 0 | Me | (A76) | (A76) |
| (E2-77) | (1-2) | 0 | Me | (A77) | (A77) |

TABLE 3

| Compound | Ar¹ | n | Ar² | Ar³ |
|---|---|---|---|---|
| (E3-1) | (1-3) | 0 | (A1) | (A1) |
| (E3-2) | (1-3) | 0 | (A2) | (A2) |
| (E3-3) | (1-3) | 0 | (A3) | (A3) |
| (E3-4) | (1-3) | 0 | (A4) | (A4) |
| (E3-5) | (1-3) | 0 | (A5) | (A5) |
| (E3-6) | (1-3) | 0 | (A6) | (A6) |
| (E3-7) | (1-3) | 0 | (A7) | (A7) |
| (E3-8) | (1-3) | 0 | (A8) | (A8) |
| (E3-9) | (1-3) | 0 | (A9) | (A9) |
| (E3-10) | (1-3) | 0 | (A10) | (A10) |
| (E3-11) | (1-3) | 0 | (A11) | (A11) |
| (E3-12) | (1-3) | 0 | (A12) | (A12) |
| (E3-13) | (1-3) | 0 | (A13) | (A13) |
| (E3-14) | (1-3) | 0 | (A14) | (A14) |
| (E3-15) | (1-3) | 0 | (A15) | (A15) |
| (E3-16) | (1-3) | 0 | (A16) | (A16) |
| (E3-17) | (1-3) | 0 | (A17) | (A17) |
| (E3-18) | (1-3) | 0 | (A18) | (A18) |
| (E3-19) | (1-3) | 0 | (A19) | (A19) |
| (E3-20) | (1-3) | 0 | (A20) | (A20) |
| (E3-21) | (1-3) | 0 | (A21) | (A21) |
| (E3-22) | (1-3) | 0 | (A22) | (A22) |
| (E3-23) | (1-3) | 0 | (A23) | (A23) |
| (E3-24) | (1-3) | 0 | (A24) | (A24) |
| (E3-25) | (1-3) | 0 | (A25) | (A25) |
| (E3-26) | (1-3) | 0 | (A26) | (A26) |
| (E3-27) | (1-3) | 0 | (A27) | (A27) |
| (E3-28) | (1-3) | 0 | (A28) | (A28) |
| (E3-29) | (1-3) | 0 | (A29) | (A29) |
| (E3-30) | (1-3) | 0 | (A30) | (A30) |
| (E3-31) | (1-3) | 0 | (A31) | (A31) |
| (E3-32) | (1-3) | 0 | (A32) | (A32) |
| (E3-33) | (1-3) | 0 | (A33) | (A33) |
| (E3-34) | (1-3) | 0 | (A34) | (A34) |
| (E3-35) | (1-3) | 0 | (A35) | (A35) |
| (E3-36) | (1-3) | 0 | (A36) | (A36) |
| (E3-37) | (1-3) | 0 | (A37) | (A37) |
| (E3-38) | (1-3) | 0 | (A38) | (A38) |
| (E3-39) | (1-3) | 0 | (A39) | (A39) |
| (E3-40) | (1-3) | 0 | (A40) | (A40) |
| (E3-41) | (1-3) | 0 | (A41) | (A41) |
| (E3-42) | (1-3) | 0 | (A42) | (A42) |
| (E3-43) | (1-3) | 0 | (A43) | (A43) |
| (E3-44) | (1-3) | 0 | (A44) | (A44) |
| (E3-45) | (1-3) | 0 | (A45) | (A45) |
| (E3-46) | (1-3) | 0 | (A46) | (A46) |
| (E3-47) | (1-3) | 0 | (A47) | (A47) |
| (E3-48) | (1-3) | 0 | (A48) | (A48) |
| (E3-49) | (1-3) | 0 | (A49) | (A49) |
| (E3-50) | (1-3) | 0 | (A50) | (A50) |
| (E3-51) | (1-3) | 0 | (A51) | (A51) |
| (E3-52) | (1-3) | 0 | (A52) | (A52) |
| (E3-53) | (1-3) | 0 | (A53) | (A53) |
| (E3-54) | (1-3) | 0 | (A54) | (A54) |
| (E3-55) | (1-3) | 0 | (A55) | (A55) |
| (E3-56) | (1-3) | 0 | (A56) | (A56) |
| (E3-57) | (1-3) | 0 | (A57) | (A57) |
| (E3-58) | (1-3) | 0 | (A58) | (A58) |
| (E3-59) | (1-3) | 0 | (A59) | (A59) |
| (E3-60) | (1-3) | 0 | (A60) | (A60) |
| (E3-61) | (1-3) | 0 | (A61) | (A61) |
| (E3-62) | (1-3) | 0 | (A62) | (A62) |
| (E3-63) | (1-3) | 0 | (A63) | (A63) |
| (E3-64) | (1-3) | 0 | (A64) | (A64) |
| (E3-65) | (1-3) | 0 | (A65) | (A65) |
| (E3-66) | (1-3) | 0 | (A66) | (A66) |
| (E3-67) | (1-3) | 0 | (A67) | (A67) |
| (E3-68) | (1-3) | 0 | (A68) | (A68) |
| (E3-69) | (1-3) | 0 | (A69) | (A69) |
| (E3-70) | (1-3) | 0 | (A70) | (A70) |
| (E3-71) | (1-3) | 0 | (A71) | (A71) |
| (E3-72) | (1-3) | 0 | (A72) | (A72) |
| (E3-73) | (1-3) | 0 | (A73) | (A73) |
| (E3-74) | (1-3) | 0 | (A74) | (A74) |
| (E3-75) | (1-3) | 0 | (A75) | (A75) |
| (E3-76) | (1-3) | 0 | (A76) | (A76) |
| (E3-77) | (1-3) | 0 | (A77) | (A77) |

TABLE 4

| Compound | Ar¹ | n | Ar² | Ar³ |
|---|---|---|---|---|
| (E4-1) | (1-4) | 0 | (A1) | (A1) |
| (E4-2) | (1-4) | 0 | (A2) | (A2) |
| (E4-3) | (1-4) | 0 | (A3) | (A3) |
| (E4-4) | (1-4) | 0 | (A4) | (A4) |
| (E4-5) | (1-4) | 0 | (A5) | (A5) |
| (E4-6) | (1-4) | 0 | (A6) | (A6) |
| (E4-7) | (1-4) | 0 | (A7) | (A7) |
| (E4-8) | (1-4) | 0 | (A8) | (A8) |
| (E4-9) | (1-4) | 0 | (A9) | (A9) |
| (E4-10) | (1-4) | 0 | (A10) | (A10) |
| (E4-11) | (1-4) | 0 | (A11) | (A11) |
| (E4-12) | (1-4) | 0 | (A12) | (A12) |
| (E4-13) | (1-4) | 0 | (A13) | (A13) |
| (E4-14) | (1-4) | 0 | (A14) | (A14) |
| (E4-15) | (1-4) | 0 | (A15) | (A15) |
| (E4-16) | (1-4) | 0 | (A16) | (A16) |
| (E4-17) | (1-4) | 0 | (A17) | (A17) |
| (E4-18) | (1-4) | 0 | (A18) | (A18) |
| (E4-19) | (1-4) | 0 | (A19) | (A19) |
| (E4-20) | (1-4) | 0 | (A20) | (A20) |
| (E4-21) | (1-4) | 0 | (A21) | (A21) |
| (E4-22) | (1-4) | 0 | (A22) | (A22) |
| (E4-23) | (1-4) | 0 | (A23) | (A23) |
| (E4-24) | (1-4) | 0 | (A24) | (A24) |
| (E4-25) | (1-4) | 0 | (A25) | (A25) |
| (E4-26) | (1-4) | 0 | (A26) | (A26) |
| (E4-27) | (1-4) | 0 | (A27) | (A27) |
| (E4-28) | (1-4) | 0 | (A28) | (A28) |
| (E4-29) | (1-4) | 0 | (A29) | (A29) |
| (E4-30) | (1-4) | 0 | (A30) | (A30) |
| (E4-31) | (1-4) | 0 | (A31) | (A31) |
| (E4-32) | (1-4) | 0 | (A32) | (A32) |
| (E4-33) | (1-4) | 0 | (A33) | (A33) |
| (E4-34) | (1-4) | 0 | (A34) | (A34) |
| (E4-35) | (1-4) | 0 | (A35) | (A35) |
| (E4-36) | (1-4) | 0 | (A36) | (A36) |
| (E4-37) | (1-4) | 0 | (A37) | (A37) |
| (E4-38) | (1-4) | 0 | (A38) | (A38) |
| (E4-39) | (1-4) | 0 | (A39) | (A39) |
| (E4-40) | (1-4) | 0 | (A40) | (A40) |
| (E4-41) | (1-4) | 0 | (A41) | (A41) |
| (E4-42) | (1-4) | 0 | (A42) | (A42) |
| (E4-43) | (1-4) | 0 | (A43) | (A43) |
| (E4-44) | (1-4) | 0 | (A44) | (A44) |
| (E4-45) | (1-4) | 0 | (A45) | (A45) |
| (E4-46) | (1-4) | 0 | (A46) | (A46) |
| (E4-47) | (1-4) | 0 | (A47) | (A47) |
| (E4-48) | (1-4) | 0 | (A48) | (A48) |
| (E4-49) | (1-4) | 0 | (A49) | (A49) |
| (E4-50) | (1-4) | 0 | (A50) | (A50) |
| (E4-51) | (1-4) | 0 | (A51) | (A51) |
| (E4-52) | (1-4) | 0 | (A52) | (A52) |
| (E4-53) | (1-4) | 0 | (A53) | (A53) |
| (E4-54) | (1-4) | 0 | (A54) | (A54) |
| (E4-55) | (1-4) | 0 | (A55) | (A55) |
| (E4-56) | (1-4) | 0 | (A56) | (A56) |
| (E4-57) | (1-4) | 0 | (A57) | (A57) |
| (E4-58) | (1-4) | 0 | (A58) | (A58) |
| (E4-59) | (1-4) | 0 | (A59) | (A59) |
| (E4-60) | (1-4) | 0 | (A60) | (A60) |
| (E4-61) | (1-4) | 0 | (A61) | (A61) |
| (E4-62) | (1-4) | 0 | (A62) | (A62) |
| (E4-63) | (1-4) | 0 | (A63) | (A63) |
| (E4-64) | (1-4) | 0 | (A64) | (A64) |
| (E4-65) | (1-4) | 0 | (A65) | (A65) |
| (E4-66) | (1-4) | 0 | (A66) | (A66) |
| (E4-67) | (1-4) | 0 | (A67) | (A67) |
| (E4-68) | (1-4) | 0 | (A68) | (A68) |
| (E4-69) | (1-4) | 0 | (A69) | (A69) |
| (E4-70) | (1-4) | 0 | (A70) | (A70) |
| (E4-71) | (1-4) | 0 | (A71) | (A71) |
| (E4-72) | (1-4) | 0 | (A72) | (A72) |
| (E4-73) | (1-4) | 0 | (A73) | (A73) |
| (E4-74) | (1-4) | 0 | (A74) | (A74) |
| (E4-75) | (1-4) | 0 | (A75) | (A75) |
| (E4-76) | (1-4) | 0 | (A76) | (A76) |
| (E4-77) | (1-4) | 0 | (A77) | (A77) |

TABLE 5

| Compound | Ar¹ | n | Ar² | Ar³ |
|---|---|---|---|---|
| (E5-1) | (1-5) | 0 | (A1) | (A1) |
| (E5-2) | (1-5) | 0 | (A2) | (A2) |
| (E5-3) | (1-5) | 0 | (A3) | (A3) |
| (E5-4) | (1-5) | 0 | (A4) | (A4) |
| (E5-5) | (1-5) | 0 | (A5) | (A5) |
| (E5-6) | (1-5) | 0 | (A6) | (A6) |
| (E5-7) | (1-5) | 0 | (A7) | (A7) |
| (E5-8) | (1-5) | 0 | (A8) | (A8) |
| (E5-9) | (1-5) | 0 | (A9) | (A9) |
| (E5-10) | (1-5) | 0 | (A10) | (A10) |
| (E5-11) | (1-5) | 0 | (A11) | (A11) |
| (E5-12) | (1-5) | 0 | (A12) | (A12) |
| (E5-13) | (1-5) | 0 | (A13) | (A13) |
| (E5-14) | (1-5) | 0 | (A14) | (A14) |
| (E5-15) | (1-5) | 0 | (A15) | (A15) |
| (E5-16) | (1-5) | 0 | (A16) | (A16) |
| (E5-17) | (1-5) | 0 | (A17) | (A17) |
| (E5-18) | (1-5) | 0 | (A18) | (A18) |
| (E5-19) | (1-5) | 0 | (A19) | (A19) |
| (E5-20) | (1-5) | 0 | (A20) | (A20) |
| (E5-21) | (1-5) | 0 | (A21) | (A21) |
| (E5-22) | (1-5) | 0 | (A22) | (A22) |
| (E5-23) | (1-5) | 0 | (A23) | (A23) |
| (E5-24) | (1-5) | 0 | (A24) | (A24) |
| (E5-25) | (1-5) | 0 | (A25) | (A25) |
| (E5-26) | (1-5) | 0 | (A26) | (A26) |
| (E5-27) | (1-5) | 0 | (A27) | (A27) |
| (E5-28) | (1-5) | 0 | (A28) | (A28) |
| (E5-29) | (1-5) | 0 | (A29) | (A29) |
| (E5-30) | (1-5) | 0 | (A30) | (A30) |
| (E5-31) | (1-5) | 0 | (A31) | (A31) |
| (E5-32) | (1-5) | 0 | (A32) | (A32) |
| (E5-33) | (1-5) | 0 | (A33) | (A33) |
| (E5-34) | (1-5) | 0 | (A34) | (A34) |
| (E5-35) | (1-5) | 0 | (A35) | (A35) |
| (E5-36) | (1-5) | 0 | (A36) | (A36) |
| (E5-37) | (1-5) | 0 | (A37) | (A37) |
| (E5-38) | (1-5) | 0 | (A38) | (A38) |
| (E5-39) | (1-5) | 0 | (A39) | (A39) |
| (E5-40) | (1-5) | 0 | (A40) | (A40) |
| (E5-41) | (1-5) | 0 | (A41) | (A41) |
| (E5-42) | (1-5) | 0 | (A42) | (A42) |
| (E5-43) | (1-5) | 0 | (A43) | (A43) |
| (E5-44) | (1-5) | 0 | (A44) | (A44) |
| (E5-45) | (1-5) | 0 | (A45) | (A45) |
| (E5-46) | (1-5) | 0 | (A46) | (A46) |
| (E5-47) | (1-5) | 0 | (A47) | (A47) |
| (E5-48) | (1-5) | 0 | (A48) | (A48) |
| (E5-49) | (1-5) | 0 | (A49) | (A49) |
| (E5-50) | (1-5) | 0 | (A50) | (A50) |
| (E5-51) | (1-5) | 0 | (A51) | (A51) |
| (E5-52) | (1-5) | 0 | (A52) | (A52) |
| (E5-53) | (1-5) | 0 | (A53) | (A53) |
| (E5-54) | (1-5) | 0 | (A54) | (A54) |
| (E5-55) | (1-5) | 0 | (A55) | (A55) |
| (E5-56) | (1-5) | 0 | (A56) | (A56) |
| (E5-57) | (1-5) | 0 | (A57) | (A57) |
| (E5-58) | (1-5) | 0 | (A58) | (A58) |
| (E5-59) | (1-5) | 0 | (A59) | (A59) |
| (E5-60) | (1-5) | 0 | (A60) | (A60) |
| (E5-61) | (1-5) | 0 | (A61) | (A61) |
| (E5-62) | (1-5) | 0 | (A62) | (A62) |
| (E5-63) | (1-5) | 0 | (A63) | (A63) |
| (E5-64) | (1-5) | 0 | (A64) | (A64) |
| (E5-65) | (1-5) | 0 | (A65) | (A65) |
| (E5-66) | (1-5) | 0 | (A66) | (A66) |
| (E5-67) | (1-5) | 0 | (A67) | (A67) |
| (E5-68) | (1-5) | 0 | (A68) | (A68) |
| (E5-69) | (1-5) | 0 | (A69) | (A69) |
| (E5-70) | (1-5) | 0 | (A70) | (A70) |
| (E5-71) | (1-5) | 0 | (A71) | (A71) |
| (E5-72) | (1-5) | 0 | (A72) | (A72) |
| (E5-73) | (1-5) | 0 | (A73) | (A73) |
| (E5-74) | (1-5) | 0 | (A74) | (A74) |
| (E5-75) | (1-5) | 0 | (A75) | (A75) |
| (E5-76) | (1-5) | 0 | (A75) | (A76) |
| (E5-77) | (1-5) | 0 | (A77) | (A77) |

TABLE 6

| Compound | Ar¹ | n | Ar² | Ar³ |
|---|---|---|---|---|
| (E6-1) | (1-6) | 0 | (A1) | (A1) |
| (E6-2) | (1-6) | 0 | (A2) | (A2) |
| (E6-3) | (1-6) | 0 | (A3) | (A3) |
| (E6-4) | (1-6) | 0 | (A4) | (A4) |
| (E6-5) | (1-6) | 0 | (A5) | (A5) |
| (E6-6) | (1-6) | 0 | (A6) | (A6) |
| (E6-7) | (1-6) | 0 | (A7) | (A7) |
| (E6-8) | (1-6) | 0 | (A8) | (A8) |
| (E6-9) | (1-6) | 0 | (A9) | (A9) |
| (E6-10) | (1-6) | 0 | (A10) | (A10) |
| (E6-11) | (1-6) | 0 | (A11) | (A11) |
| (E6-12) | (1-6) | 0 | (A12) | (A12) |
| (E6-13) | (1-6) | 0 | (A13) | (A13) |
| (E6-14) | (1-6) | 0 | (A14) | (A14) |
| (E6-15) | (1-6) | 0 | (A15) | (A15) |
| (E6-16) | (1-6) | 0 | (A16) | (A16) |
| (E6-17) | (1-6) | 0 | (A17) | (A17) |
| (E6-18) | (1-6) | 0 | (A18) | (A18) |
| (E6-19) | (1-6) | 0 | (A19) | (A19) |
| (E6-20) | (1-6) | 0 | (A20) | (A20) |
| (E6-21) | (1-6) | 0 | (A21) | (A21) |
| (E6-22) | (1-6) | 0 | (A22) | (A22) |
| (E6-23) | (1-6) | 0 | (A23) | (A23) |
| (E6-24) | (1-6) | 0 | (A24) | (A24) |
| (E6-25) | (1-6) | 0 | (A25) | (A25) |
| (E6-26) | (1-6) | 0 | (A26) | (A26) |
| (E6-27) | (1-6) | 0 | (A27) | (A27) |
| (E6-28) | (1-6) | 0 | (A28) | (A28) |
| (E6-29) | (1-6) | 0 | (A29) | (A29) |
| (E6-30) | (1-6) | 0 | (A30) | (A30) |
| (E6-31) | (1-6) | 0 | (A31) | (A31) |
| (E6-32) | (1-6) | 0 | (A32) | (A32) |
| (E6-33) | (1-6) | 0 | (A33) | (A33) |
| (E6-34) | (1-6) | 0 | (A34) | (A34) |
| (E6-35) | (1-6) | 0 | (A35) | (A35) |
| (E6-36) | (1-6) | 0 | (A36) | (A36) |
| (E6-37) | (1-6) | 0 | (A37) | (A37) |
| (E6-38) | (1-6) | 0 | (A38) | (A38) |
| (E6-39) | (1-6) | 0 | (A39) | (A39) |
| (E6-40) | (1-6) | 0 | (A40) | (A40) |
| (E6-41) | (1-6) | 0 | (A41) | (A41) |
| (E6-42) | (1-6) | 0 | (A42) | (A42) |
| (E6-43) | (1-6) | 0 | (A43) | (A43) |
| (E6-44) | (1-6) | 0 | (A44) | (A44) |
| (E6-45) | (1-6) | 0 | (A45) | (A45) |
| (E6-46) | (1-6) | 0 | (A46) | (A46) |
| (E6-47) | (1-6) | 0 | (A47) | (A47) |
| (E6-48) | (1-6) | 0 | (A48) | (A48) |
| (E6-49) | (1-6) | 0 | (A49) | (A49) |
| (E6-50) | (1-6) | 0 | (A50) | (A50) |
| (E6-51) | (1-6) | 0 | (A51) | (A51) |
| (E6-52) | (1-6) | 0 | (A52) | (A52) |
| (E6-53) | (1-6) | 0 | (A53) | (A53) |
| (E6-54) | (1-6) | 0 | (A54) | (A54) |
| (E6-55) | (1-6) | 0 | (A55) | (A55) |
| (E6-56) | (1-6) | 0 | (A56) | (A56) |
| (E6-57) | (1-6) | 0 | (A57) | (A57) |
| (E6-58) | (1-6) | 0 | (A58) | (A58) |
| (E6-59) | (1-6) | 0 | (A59) | (A59) |
| (E6-60) | (1-6) | 0 | (A60) | (A60) |
| (E6-61) | (1-6) | 0 | (A61) | (A61) |
| (E6-62) | (1-6) | 0 | (A62) | (A62) |
| (E6-63) | (1-6) | 0 | (A63) | (A63) |
| (E6-64) | (1-6) | 0 | (A64) | (A64) |
| (E6-65) | (1-6) | 0 | (A65) | (A65) |
| (E6-66) | (1-6) | 0 | (A66) | (A66) |
| (E6-67) | (1-6) | 0 | (A67) | (A67) |
| (E6-68) | (1-6) | 0 | (A68) | (A68) |
| (E6-69) | (1-6) | 0 | (A69) | (A69) |
| (E6-70) | (1-6) | 0 | (A70) | (A70) |
| (E6-71) | (1-6) | 0 | (A71) | (A71) |
| (E6-72) | (1-6) | 0 | (A72) | (A72) |
| (E6-73) | (1-6) | 0 | (A73) | (A73) |
| (E6-74) | (1-6) | 0 | (A74) | (A74) |
| (E6-75) | (1-6) | 0 | (A75) | (A75) |
| (E6-76) | (1-6) | 0 | (A76) | (A76) |
| (E6-77) | (1-6) | 0 | (A77) | (A77) |

TABLE 7

| Compound | Ar¹ | m | Ar² | Ar³ |
|---|---|---|---|---|
| (E7-1) | (1-7) | 0 | (A1) | (A1) |
| (E7-2) | (1-7) | 0 | (A2) | (A2) |
| (E7-3) | (1-7) | 0 | (A3) | (A3) |
| (E7-4) | (1-7) | 0 | (A4) | (A4) |
| (E7-5) | (1-7) | 0 | (A5) | (A5) |
| (E7-6) | (1-7) | 0 | (A6) | (A6) |
| (E7-7) | (1-7) | 0 | (A7) | (A7) |
| (E7-8) | (1-7) | 0 | (A8) | (A8) |
| (E7-9) | (1-7) | 0 | (A9) | (A9) |
| (E7-10) | (1-7) | 0 | (A10) | (A10) |
| (E7-11) | (1-7) | 0 | (A11) | (A11) |
| (E7-12) | (1-7) | 0 | (A12) | (A12) |
| (E7-13) | (1-7) | 0 | (A13) | (A13) |
| (E7-14) | (1-7) | 0 | (A14) | (A14) |
| (E7-15) | (1-7) | 0 | (A15) | (A15) |
| (E7-16) | (1-7) | 0 | (A16) | (A16) |
| (E7-17) | (1-7) | 0 | (A17) | (A17) |
| (E7-18) | (1-7) | 0 | (A18) | (A18) |
| (E7-19) | (1-7) | 0 | (A19) | (A19) |
| (E7-20) | (1-7) | 0 | (A20) | (A20) |
| (E7-21) | (1-7) | 0 | (A21) | (A21) |
| (E7-22) | (1-7) | 0 | (A22) | (A22) |
| (E7-23) | (1-7) | 0 | (A23) | (A23) |
| (E7-24) | (1-7) | 0 | (A24) | (A24) |
| (E7-25) | (1-7) | 0 | (A25) | (A25) |
| (E7-26) | (1-7) | 0 | (A26) | (A26) |
| (E7-27) | (1-7) | 0 | (A27) | (A27) |
| (E7-28) | (1-7) | 0 | (A28) | (A28) |
| (E7-29) | (1-7) | 0 | (A29) | (A29) |
| (E7-30) | (1-7) | 0 | (A30) | (A30) |
| (E7-31) | (1-7) | 0 | (A31) | (A31) |
| (E7-32) | (1-7) | 0 | (A32) | (A32) |
| (E7-33) | (1-7) | 0 | (A33) | (A33) |
| (E7-34) | (1-7) | 0 | (A34) | (A34) |
| (E7-35) | (1-7) | 0 | (A36) | (A35) |
| (E7-36) | (1-7) | 0 | (A36) | (A36) |
| (E7-37) | (1-7) | 0 | (A37) | (A37) |
| (E7-38) | (1-7) | 0 | (A38) | (A38) |
| (E7-39) | (1-7) | 0 | (A39) | (A39) |
| (E7-40) | (1-7) | 0 | (A40) | (A40) |
| (E7-41) | (1-7) | 0 | (A41) | (A41) |
| (E7-42) | (1-7) | 0 | (A42) | (A42) |
| (E7-43) | (1-7) | 0 | (A43) | (A43) |
| (E7-44) | (1-7) | 0 | (A44) | (A44) |
| (E7-45) | (1-7) | 0 | (A45) | (A45) |
| (E7-46) | (1-7) | 0 | (A46) | (A46) |
| (E7-47) | (1-7) | 0 | (A47) | (A47) |
| (E7-48) | (1-7) | 0 | (A48) | (A48) |
| (E7-49) | (1-7) | 0 | (A49) | (A49) |
| (E7-50) | (1-7) | 0 | (A50) | (A50) |
| (E7-51) | (1-7) | 0 | (A51) | (A51) |
| (E7-52) | (1-7) | 0 | (A52) | (A52) |
| (E7-53) | (1-7) | 0 | (A53) | (A53) |
| (E7-54) | (1-7) | 0 | (A54) | (A54) |
| (E7-55) | (1-7) | 0 | (A55) | (A55) |
| (E7-56) | (1-7) | 0 | (A56) | (A56) |
| (E7-57) | (1-7) | 0 | (A57) | (A57) |
| (E7-58) | (1-7) | 0 | (A58) | (A58) |
| (E7-59) | (1-7) | 0 | (A59) | (A59) |
| (E7-60) | (1-7) | 0 | (A60) | (A60) |
| (E7-61) | (1-7) | 0 | (A61) | (A61) |
| (E7-62) | (1-7) | 0 | (A62) | (A62) |
| (E7-63) | (1-7) | 0 | (A63) | (A63) |
| (E7-64) | (1-7) | 0 | (A64) | (A64) |
| (E7-65) | (1-7) | 0 | (A65) | (A65) |
| (E7-66) | (1-7) | 0 | (A66) | (A66) |
| (E7-67) | (1-7) | 0 | (A67) | (A67) |
| (E7-68) | (1-7) | 0 | (A68) | (A68) |
| (E7-69) | (1-7) | 0 | (A69) | (A69) |
| (E7-70) | (1-7) | 0 | (A70) | (A70) |
| (E7-71) | (1-7) | 0 | (A71) | (A71) |
| (E7-72) | (1-7) | 0 | (A72) | (A72) |
| (E7-73) | (1-7) | 0 | (A73) | (A73) |
| (E7-74) | (1-7) | 0 | (A74) | (A74) |
| (E7-75) | (1-7) | 0 | (A75) | (A75) |
| (E7-76) | (1-7) | 0 | (A76) | (A76) |
| (E7-77) | (1-7) | 0 | (A77) | (A77) |

TABLE 8

| Compound | Ar¹ | m | Cb² | Ar² | Ar³ |
| --- | --- | --- | --- | --- | --- |
| (E8-1) | (1-8) | 0 | Me | (A1) | (A1) |
| (E8-2) | (1-8) | 0 | Me | (A2) | (A2) |
| (E8-3) | (1-8) | 0 | Me | (A3) | (A3) |
| (E8-4) | (1-8) | 0 | Me | (A4) | (A4) |
| (E8-5) | (1-8) | 0 | Me | (A5) | (A5) |
| (E8-6) | (1-8) | 0 | Me | (A6) | (A6) |
| (E8-7) | (1-8) | 0 | Me | (A7) | (A7) |
| (E8-8) | (1-8) | 0 | Me | (A8) | (A8) |
| (E8-9) | (1-8) | 0 | Me | (A9) | (A9) |
| (E8-10) | (1-8) | 0 | Me | (A10) | (A10) |
| (E8-11) | (1-8) | 0 | Me | (A11) | (A11) |
| (E8-12) | (1-8) | 0 | Me | (A12) | (A12) |
| (E8-13) | (1-8) | 0 | Me | (A13) | (A13) |
| (E8-14) | (1-8) | 0 | Me | (A14) | (A14) |
| (E8-15) | (1-8) | 0 | Me | (A15) | (A15) |
| (E8-16) | (1-8) | 0 | Me | (A16) | (A16) |
| (E8-17) | (1-8) | 0 | Me | (A17) | (A17) |
| (E8-18) | (1-8) | 0 | Me | (A18) | (A18) |
| (E8-19) | (1-8) | 0 | Me | (A19) | (A19) |
| (E8-20) | (1-8) | 0 | Me | (A20) | (A20) |
| (E8-21) | (1-8) | 0 | Me | (A21) | (A21) |
| (E8-22) | (1-8) | 0 | Me | (A22) | (A22) |
| (E8-23) | (1-8) | 0 | Me | (A23) | (A23) |
| (E8-24) | (1-8) | 0 | Me | (A24) | (A24) |
| (E8-25) | (1-8) | 0 | Me | (A25) | (A25) |
| (E8-26) | (1-8) | 0 | Me | (A26) | (A26) |
| (E8-27) | (1-8) | 0 | Me | (A27) | (A27) |
| (E8-28) | (1-8) | 0 | Me | (A28) | (A28) |
| (E8-29) | (1-8) | 0 | Me | (A29) | (A29) |
| (E8-30) | (1-8) | 0 | Me | (A30) | (A30) |
| (E8-31) | (1-8) | 0 | Me | (A31) | (A31) |
| (E8-32) | (1-8) | 0 | Me | (A32) | (A32) |
| (E8-33) | (1-8) | 0 | Me | (A33) | (A33) |
| (E8-34) | (1-8) | 0 | Me | (A34) | (A34) |
| (E8-35) | (1-8) | 0 | Me | (A35) | (A35) |
| (E8-36) | (1-8) | 0 | Me | (A36) | (A36) |
| (E8-37) | (1-8) | 0 | Me | (A37) | (A37) |
| (E8-38) | (1-8) | 0 | Me | (A38) | (A38) |
| (E8-39) | (1-8) | 0 | Me | (A39) | (A39) |
| (E8-40) | (1-8) | 0 | Me | (A40) | (A40) |
| (E8-41) | (1-8) | 0 | Me | (A41) | (A41) |
| (E8-42) | (1-8) | 0 | Me | (A42) | (A42) |
| (E8-43) | (1-8) | 0 | Me | (A43) | (A43) |
| (E8-44) | (1-8) | 0 | Me | (A44) | (A44) |
| (E8-45) | (1-8) | 0 | Me | (A45) | (A45) |
| (E8-46) | (1-8) | 0 | Me | (A46) | (A46) |
| (E8-47) | (1-8) | 0 | Me | (A47) | (A47) |
| (E8-48) | (1-8) | 0 | Me | (A48) | (A48) |
| (E8-49) | (1-8) | 0 | Me | (A49) | (A49) |
| (E8-50) | (1-8) | 0 | Me | (A50) | (A50) |
| (E8-51) | (1-8) | 0 | Me | (A51) | (A51) |
| (E8-52) | (1-8) | 0 | Me | (A52) | (A52) |
| (E8-53) | (1-8) | 0 | Me | (A53) | (A53) |
| (E8-54) | (1-8) | 0 | Me | (A54) | (A54) |
| (E8-55) | (1-8) | 0 | Me | (A55) | (A55) |
| (E8-56) | (1-8) | 0 | Me | (A56) | (A56) |
| (E8-57) | (1-8) | 0 | Me | (A57) | (A57) |
| (E8-58) | (1-8) | 0 | Me | (A58) | (A58) |
| (E8-59) | (1-8) | 0 | Me | (A59) | (A59) |
| (E8-60) | (1-8) | 0 | Me | (A60) | (A60) |
| (E8-61) | (1-8) | 0 | Me | (A61) | (A61) |
| (E8-62) | (1-8) | 0 | Me | (A62) | (A62) |
| (E8-63) | (1-8) | 0 | Me | (A63) | (A63) |
| (E8-64) | (1-8) | 0 | Me | (A64) | (A64) |
| (E8-65) | (1-8) | 0 | Me | (A65) | (A65) |
| (E8-66) | (1-8) | 0 | Me | (A66) | (A66) |
| (E8-67) | (1-8) | 0 | Me | (A67) | (A67) |
| (E8-68) | (1-8) | 0 | Me | (A68) | (A68) |
| (E8-69) | (1-8) | 0 | Me | (A69) | (A69) |
| (E8-70) | (1-8) | 0 | Me | (A70) | (A70) |
| (E8-71) | (1-8) | 0 | Me | (A71) | (A71) |
| (E8-72) | (1-8) | 0 | Me | (A72) | (A72) |
| (E8-73) | (1-8) | 0 | Me | (A73) | (A73) |
| (E8-74) | (1-8) | 0 | Me | (A74) | (A74) |
| (E8-75) | (1-8) | 0 | Me | (A75) | (A75) |
| (E8-76) | (1-8) | 0 | Me | (A76) | (A76) |
| (E8-77) | (1-8) | 0 | Me | (A77) | (A77) |

TABLE 9

| Compound | Ar¹ | n | Ar² | Ar³ |
| --- | --- | --- | --- | --- |
| (E9-1) | (1-9) | 0 | (A1) | (A1) |
| (E9-2) | (1-9) | 0 | (A2) | (A2) |
| (E9-3) | (1-9) | 0 | (A3) | (A3) |
| (E9-4) | (1-9) | 0 | (A4) | (A4) |
| (E9-5) | (1-9) | 0 | (A5) | (A5) |
| (E9-6) | (1-9) | 0 | (A6) | (A6) |
| (E9-7) | (1-9) | 0 | (A7) | (A7) |
| (E9-8) | (1-9) | 0 | (A8) | (A8) |
| (E9-9) | (1-9) | 0 | (A9) | (A9) |
| (E9-10) | (1-9) | 0 | (A10) | (A10) |
| (E9-11) | (1-9) | 0 | (A11) | (A11) |
| (E9-12) | (1-9) | 0 | (A12) | (A12) |
| (E9-13) | (1-9) | 0 | (A13) | (A13) |
| (E9-14) | (1-9) | 0 | (A14) | (A14) |
| (E9-15) | (1-9) | 0 | (A15) | (A15) |
| (E9-16) | (1-9) | 0 | (A16) | (A16) |
| (E9-17) | (1-9) | 0 | (A17) | (A17) |
| (E9-18) | (1-9) | 0 | (A18) | (A18) |
| (E9-19) | (1-9) | 0 | (A19) | (A19) |
| (E9-20) | (1-9) | 0 | (A20) | (A20) |
| (E9-21) | (1-9) | 0 | (A21) | (A21) |
| (E9-22) | (1-9) | 0 | (A22) | (A22) |
| (E9-23) | (1-9) | 0 | (A23) | (A23) |
| (E9-24) | (1-9) | 0 | (A24) | (A24) |
| (E9-25) | (1-9) | 0 | (A25) | (A25) |
| (E9-26) | (1-9) | 0 | (A26) | (A26) |
| (E9-27) | (1-9) | 0 | (A27) | (A27) |
| (E9-28) | (1-9) | 0 | (A28) | (A28) |
| (E9-29) | (1-9) | 0 | (A29) | (A29) |
| (E9-30) | (1-9) | 0 | (A30) | (A30) |
| (E9-31) | (1-9) | 0 | (A31) | (A31) |
| (E9-32) | (1-9) | 0 | (A32) | (A32) |
| (E9-33) | (1-9) | 0 | (A33) | (A33) |
| (E9-34) | (1-9) | 0 | (A34) | (A34) |
| (E9-35) | (1-9) | 0 | (A35) | (A35) |
| (E9-36) | (1-9) | 0 | (A36) | (A36) |
| (E9-37) | (1-9) | 0 | (A37) | (A37) |
| (E9-38) | (1-9) | 0 | (A38) | (A38) |
| (E9-39) | (1-9) | 0 | (A39) | (A39) |
| (E9-40) | (1-9) | 0 | (A40) | (A40) |
| (E9-41) | (1-9) | 0 | (A41) | (A41) |
| (E9-42) | (1-9) | 0 | (A42) | (A42) |
| (E9-43) | (1-9) | 0 | (A43) | (A43) |
| (E9-44) | (1-9) | 0 | (A44) | (A44) |
| (E9-45) | (1-9) | 0 | (A45) | (A45) |
| (E9-46) | (1-9) | 0 | (A46) | (A46) |
| (E9-47) | (1-9) | 0 | (A47) | (A47) |
| (E9-48) | (1-9) | 0 | (A48) | (A48) |
| (E9-49) | (1-9) | 0 | (A49) | (A49) |
| (E9-50) | (1-9) | 0 | (A50) | (A50) |
| (E9-51) | (1-9) | 0 | (A51) | (A51) |
| (E9-52) | (1-9) | 0 | (A52) | (A52) |
| (E9-53) | (1-9) | 0 | (A53) | (A53) |
| (E9-54) | (1-9) | 0 | (A54) | (A54) |
| (E9-55) | (1-9) | 0 | (A55) | (A55) |
| (E9-56) | (1-9) | 0 | (A56) | (A56) |
| (E9-57) | (1-9) | 0 | (A57) | (A57) |
| (E9-58) | (1-9) | 0 | (A58) | (A58) |
| (E9-59) | (1-9) | 0 | (A59) | (A59) |
| (E9-60) | (1-9) | 0 | (A60) | (A60) |
| (E9-61) | (1-9) | 0 | (A61) | (A61) |
| (E9-62) | (1-9) | 0 | (A62) | (A62) |
| (E9-63) | (1-9) | 0 | (A63) | (A63) |
| (E9-64) | (1-9) | 0 | (A64) | (A64) |
| (E9-65) | (1-9) | 0 | (A65) | (A65) |
| (E9-66) | (1-9) | 0 | (A66) | (A66) |
| (E9-67) | (1-9) | 0 | (A67) | (A67) |
| (E9-68) | (1-9) | 0 | (A68) | (A68) |
| (E9-69) | (1-9) | 0 | (A69) | (A69) |
| (E9-70) | (1-9) | 0 | (A70) | (A70) |
| (E9-71) | (1-9) | 0 | (A71) | (A71) |
| (E9-72) | (1-9) | 0 | (A72) | (A72) |
| (E9-73) | (1-9) | 0 | (A73) | (A73) |
| (E9-74) | (1-9) | 0 | (A74) | (A74) |
| (E9-75) | (1-9) | 0 | (A75) | (A75) |
| (E9-76) | (1-9) | 0 | (A76) | (A76) |
| (E9-77) | (1-9) | 0 | (A77) | (A77) |

[Method of Synthesizing Fluorine Atom-Containing Amide Compound]

The fluorine atom-containing amide compound of the invention can be synthesized by, as shown in Scheme A below, reacting an amine compound of formula (2) with a fluorine atom-containing acid halide of formula (3A) and a fluorine atom-containing acid halide of formula (3B).

Scheme A

[Chemical Formula 20]

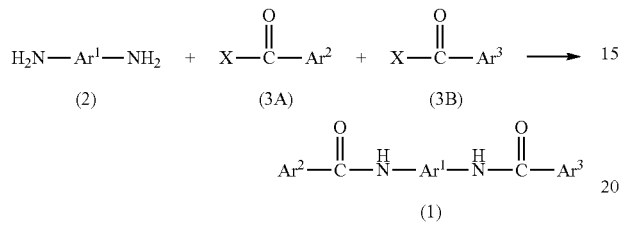

Here, $Ar^1$, $Ar^2$ and $Ar^3$ are the same as above. X is a halogen atom such as a fluorine, chlorine, bromine or iodine atom, with a chlorine or bromine atom being preferred.

Examples of the amine compound of formula (2) include those of formulas (2-1) to (2-9) below.

[Chemical Formula 21]

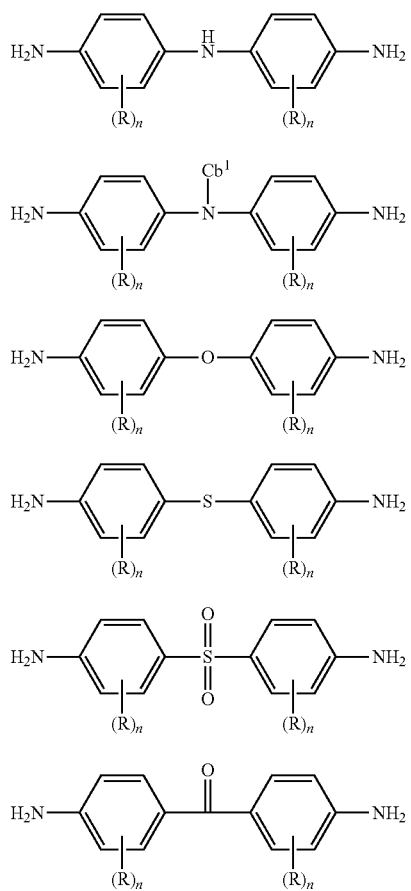

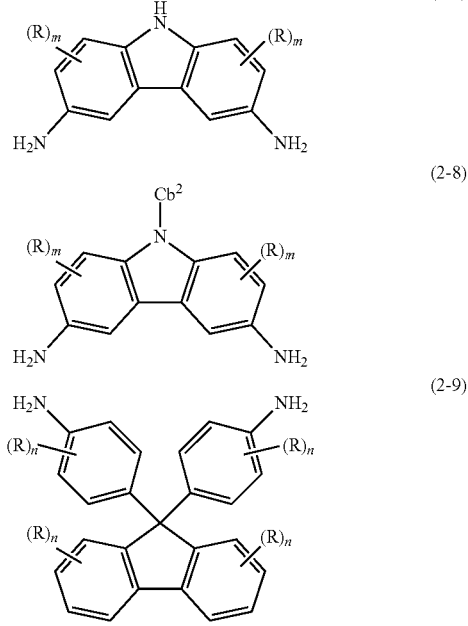

Here, R, $Cb^1$, $Cb^2$, m and n are the same as above.

Examples of the fluorine atom-containing acid halides of formulas (3A) and (3B) include, but are not limited to, 2-fluorobenzoyl chloride, 3-fluorobenzoyl chloride, 4-fluorobenzoyl chloride, 2-fluoro-4-methylbenzoyl chloride, 2-fluoro-5-methylbenzoyl chloride, 3-fluoro-4-methylbenzoyl chloride, 3-fluoro-6-methylbenzoyl chloride, 4-fluoro-2-methylbenzoyl chloride, 4-fluoro-3-methylbenzoyl chloride, 2,3-difluorobenzoyl chloride, 2,4-difluorobenzoyl chloride, 2,5-difluorobenzoyl chloride, 2,6-difluorobenzoyl chloride, 3,4-difluorobenzoyl chloride, 3,5-difluorobenzoyl chloride, 3-chloro-2-fluorobenzoyl chloride, 4-chloro-2-fluorobenzoyl chloride, 5-chloro-2-fluorobenzoyl chloride, 2-chloro-6-fluorobenzoyl chloride, 2-chloro-3-fluorobenzoyl chloride, 2-chloro-4-fluorobenzoyl chloride, 2-chloro-5-fluorobenzoyl chloride, 3-chloro-4-fluorobenzoyl chloride, 3-chloro-5-fluorobenzoyl chloride, 3-bromo-2-fluorobenzoyl chloride, 4-bromo-2-fluorobenzoyl chloride, 5-bromo-2-fluorobenzoyl chloride, 2-bromo-6-fluorobenzoyl chloride, 2-bromo-3-fluorobenzoyl chloride, 2-bromo-4-fluorobenzoyl chloride, 2-bromo-5-fluorobenzoyl chloride, 3-bromo-4-fluorobenzoyl chloride, 3-bromo-5-fluorobenzoyl chloride, 2-fluoro-5-iodobenzoyl chloride, 2-fluoro-6-iodobenzoyl chloride, 2-fluoro-3-(trifluoromethyl)benzoyl chloride, 2-fluoro-5-(trifluoromethyl)benzoyl chloride, 2-fluoro-6-(trifluoromethyl)benzoyl chloride, 3-fluoro-4-(trifluoromethyl)benzoyl chloride, 3-fluoro-5-(trifluoromethyl)benzoyl chloride, 3-fluoro-6-(trifluoromethyl)benzoyl chloride, 4-fluoro-2-(trifluoromethyl)benzoyl chloride, 4-fluoro-3-(trifluoromethyl)benzoyl chloride, 2-fluoro-4-nitrobenzoyl chloride, 2-fluoro-5-nitrobenzoyl chloride, 3-fluoro-2-nitrobenzoyl chloride, 3-fluoro-4-nitrobenzoyl chloride, 3-fluoro-6-nitrobenzoyl chloride, 4-fluoro-2-nitrobenzoyl chloride, 4-fluoro-3-nitrobenzoyl chloride, 4-cyano-2-fluorobenzoyl chloride, 3-cyano-5-fluorobenzoyl chloride, 2,3,4-trifluorobenzoyl chloride, 2,3,5-trifluorobenzoyl chloride, 2,3,6-trifluorobenzoyl chloride, 2,4,5-trifluorobenzoyl chloride, 2,4,6-trifluorobenzoyl chloride, 3,4,5-trifluorobenzoyl chloride, 4-chloro-2,4-difluorobenzoyl chloride, 2,4-dichloro-5-fluoro-4-nitrobenzoyl chloride, 2,4,5-trifluoro-3-methyl-6-nitrobenzoyl chloride, 2,3,4,5-tetrafluorobenzoyl chloride, 2,3,5,6-tetrafluorobenzoyl chloride, 2,3,5,6-tetrafluoro-4-methylbenzoyl chloride, 2,3,4,5-tetrafluoro-6-nitrobenzoyl chloride, 2,3,4,5,6-pentafluorobenzoyl chloride, 2-(trifluoromethyl)benzoyl chloride, 3-(trifluoromethyl)benzoyl chloride, 4-(trifluoromethyl)benzoyl chloride, 3-trifluoromethyl-4-ethoxybenzoyl chloride, 3,5-bis(trifluoromethyl)benzoyl chloride, 2,4,6-tris(trifluoromethyl)benzoyl chloride, 4-(pentafluoroethyl)benzoyl chloride, 4-(3-tetrafluoropropyl)benzoyl chloride, 2,3,5,6-tetrafluoro-4-(trifluoromethyl)benzoyl chloride, 2,3,5,6-tetrafluoro-4-(trifluorovinyl)benzoyl chloride and 2,3,5,6-tetrafluoro-4-(pentafluoroallyl)benzoyl chloride.

A base may be used in the reaction shown in Scheme A. Examples of the base include alkoxides such as sodium t-butoxide (t-BuONa) and potassium t-butoxide; fluorides such as lithium fluoride, potassium fluoride and cesium fluoride; carbonates such as sodium carbonate, potassium carbonate, sodium bicarbonate and potassium bicarbonate; and amines such as trimethylamine, triethylamine, diisopropylethylamine, tetramethylethylenediamine, pyridine, morpholine, N-methylmorpholine, quinuclidine, 1,4-diazabicyclo[2.2.2]octane and 4-dimethylaminopyridine, although the base is not particularly limited, so long as it is one that may be used in this type of reaction. From the standpoint of ease of handling, bases such as triethylamine, pyridine and diisopropylethylamine are especially preferred.

The reaction solvent is preferably an aprotic organic solvent, examples of which include N,N-dimethylformamide, N,N-dimethylacetamide, N-methylpyrrolidone, 1,3-dimethyl-2-imidazolidinone, dimethylsulfoxide, tetrahydrofuran and dioxane. From the standpoint of the ease of removing the reaction solvent following the reaction, N,N-dimethylformamide, N,N-dimethylacetamide, tetrahydrofuran, dioxane, toluene, xylene and mesitylene are preferred.

The charging ratio of the amine compound of formula (2), the fluorine atom-containing acid halide of formula (3A) and the fluorine atom-containing acid halide of formula (3B) is from about 1 to about 3 equivalents of each fluorine atom-containing acid halide with respect to the amine compound of formula (2).

The reaction temperature is suitably set within the range of the solvent melting point to the solvent boiling point while taking into consideration the types and amounts of the starting compounds and catalysts used, and is typically from about 0° C. to about 200° C., and preferably from 0° C. to 50° C. The reaction time differs according to the starting compounds used, the reaction temperature and other factors, and therefore cannot be strictly specified, but is generally from about 1 hour to about 24 hours.

Following reaction completion, the target fluorine atom-containing amide compound can be obtained by work-up in the usual manner.

A commercial product may be used as the amine compound of formula (2), or the amine compound may be synthesized by a known method. The fluorine atom-containing acid halide of formula (3A) and the fluorine atom-containing acid halide of formula (3B) can be obtained by reacting the respective corresponding fluorine atom-containing carboxylic acids with an electrophilic halide such as thionyl chloride, oxalyl chloride, phosphoryl chloride, sulfuryl chloride, phosphorus trichloride or phosphorus pentachloride. Also, the corresponding fluorine atom-containing carboxylic acid that is used may be a commercial product or may be synthesized by a known method (e.g., the method described in JP-A H09-67303, JP-A 1109-67304 and JP-A 2002-284733.

[Charge-Transporting Substance]

The charge-transporting varnish of the invention includes a charge-transporting substance. The charge-transporting substance is exemplified by charge-transporting oligomers such as aniline derivatives, thiophene derivatives and pyrrole derivatives. The molecular weight of the charge-transporting oligomer is generally from 200 to 8,000. However, from the standpoint of preparing a varnish that gives thin films having a high charge transportability, the molecular weight is preferably at least 300, more preferably at least 400, and even more preferably at least 500. From the standpoint of preparing a uniform varnish that gives a thin film having a high flatness, the molecular weight is preferably 6,000 or less, more preferably 5,000 or less, even more preferably 4,000 or less, and still more preferably 3,000 or less.

Of the above charge-transporting oligomers, taking into account the balance between the solubility in organic solvents and the charge transportability of the resulting thin film, aniline derivatives are preferred. Examples of aniline derivatives include the oligoaniline derivatives mentioned in JP-A 2002-151272, the oligoaniline compounds mentioned in WO 2004/105446, the oligoaniline compounds mentioned in WO 2008/032617, the oligoaniline compounds mentioned in WO 2008/032616 and the aryldiamine compounds mentioned in WO 2013/042623.

Aniline derivatives of formula (4) below can also be advantageously used.

[Chemical Formula 22]

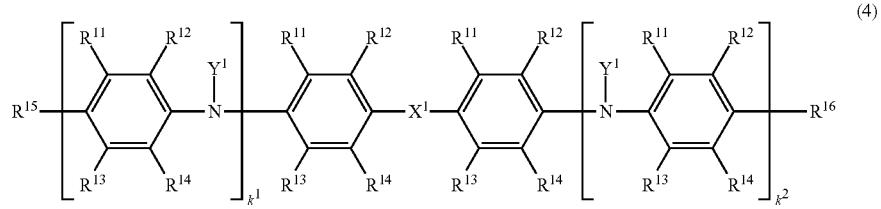

(4)

In formula (4), $X^1$ represents —$NY^1$—, —O—, —S—, —$(CR^{17}R^{18})_L$— or a single bond. When $k^1$ or $k^2$ is 0, $X^1$ represents —$NY^1$—.

Each $Y^1$ is independently a hydrogen atom, an alkyl group of 1 to 20 carbon atoms, alkenyl group of 2 to 20 carbon atoms or alkynyl group of 2 to 20 carbon atoms which may be substituted with $Z^{11}$, or an aryl group of 6 to 20 carbon atoms or heteroaryl group of 2 to 20 carbon atoms which may be substituted with $Z^{12}$.

The alkyl group of 1 to 20 carbon atoms and aryl group of 6 to 20 carbon atoms are exemplified in the same way as above.

The alkenyl group of 2 to 20 carbon atoms may be linear, branched or cyclic. Examples include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl and n-1-eicosenyl groups.

The alkynyl group of 2 to 20 carbon atoms may be linear, branched or cyclic. Examples include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecenyl and n-1-eicosynyl groups.

Examples of the heteroaryl group of 2 to 20 carbon atoms include 2-thienyl, 3-thienyl, 2-furanyl, 3-furanyl, 2-oxazolyl, 4-oxazolyl, 5-oxazolyl, 3-isooxazolyl, 4-isooxazolyl, 5-isooxazolyl, 2-thiazolyl, 4-thiazolyl, 5-thiazolyl, 3-isothiazolyl, 4-isothiazolyl, 5-isothiazolyl, 2-imidazolyl, 4-imidazolyl, 2-pyridyl, 3-pyridyl and 4-pyridyl groups.

$R^{17}$ and $R^{18}$ are each independently a hydrogen atom, a chlorine atom, a bromine atom, an iodine atom, a nitro group, a cyano group, an amino group, an aldehyde group, a hydroxyl group, a thiol group, a sulfonic acid group, a carboxyl group, an alkyl group of 1 to 20 carbon atoms, alkenyl group of 2 to 20 carbon atoms or alkynyl group of 2 to 20 carbon atoms which may be substituted with $Z^{11}$, an aryl group of 6 to 20 carbon atoms or heteroaryl group of 2 to 20 carbon atoms which may be substituted with $Z^{12}$, or —NHY$^2$, —NY$^3$Y$^4$, —C(O)Y$^5$, —OY$^6$, —SY$^7$, —SO$_3$Y$^8$, —C(O)OY$^9$, —OC(O)Y$^{10}$, —C(O)NHY$^{11}$ or —C(O)NY$^{12}$Y$^{13}$.

$Y^2$ to $Y^{13}$ are each independently an alkyl group of 1 to 20 carbon atoms, alkenyl group of 2 to 20 carbon atoms or alkynyl group of 2 to 20 carbon atoms which may be substituted with $Z^{11}$, or an aryl group of 6 to 20 carbon atoms or heteroaryl group of 2 to 20 carbon atoms which may be substituted with $Z^{12}$.

$Z^{11}$ is a chlorine atom, a bromine atom, an iodine atom, a nitro group, a cyano group, an amino group, an aldehyde group, a hydroxyl group, a thiol group, a sulfonic acid group, a carboxyl group, or an aryl group of 6 to 20 carbon atoms or heteroaryl group of 2 to 20 carbon atoms which may be substituted with $Z^{13}$.

$Z^{12}$ is a chlorine atom, a bromine atom, an iodine atom, a nitro group, a cyano group, an amino group, an aldehyde group, a hydroxyl group, a thiol group, a sulfonic acid group, a carboxyl group, or an alkyl group of 1 to 20 carbon atoms, alkenyl group of 2 to 20 carbon atoms or alkynyl group of 2 to 20 carbon atoms which may be substituted with $Z^{13}$.

$Z^{13}$ is a chlorine atom, a bromine atom, an iodine atom, a nitro group, a cyano group, an amino group, an aldehyde group, a hydroxyl group, a thiol group, a sulfonic acid group, or a carboxyl group.

The alkyl, alkenyl, alkynyl, aryl and heteroaryl groups of $R^{17}$, $R^{18}$ and $Y^2$ to $Y^{13}$ are exemplified in the same way as above.

Of these, $R^{17}$ and $R^{18}$ are preferably hydrogen atoms or alkyl groups of 1 to 20 carbon atoms which may be substituted with $Z^{11}$, more preferably hydrogen atoms or methyl groups which may be substituted with $Z^{11}$, and most preferably both hydrogen atoms.

L is the number of divalent groups represented by —(CR$^{17}$R$^{18}$)—, this number being an integer of from 1 to 20, preferably from 1 to 10, more preferably from 1 to 5, even more preferably 1 or 2, and most preferably 1. When L is 2 or more, the plurality of $R^{17}$ groups may be mutually the same or different and the plurality of $R^{18}$ groups may likewise be mutually the same or different.

In particular, $X^1$ is preferably —NY$^1$— or a single bond. $Y^1$ is preferably a hydrogen atom or an alkyl group of 1 to 20 carbon atoms which may be substituted with $Z^{11}$, more preferably a hydrogen atom or a methyl group which may be substituted with $Z^{11}$, and most preferably a hydrogen atom.

In formula (4), $R^{11}$ to $R^{16}$ are each independently a hydrogen atom, a chlorine atom, a bromine atom, an iodine atom, a nitro group, a cyano group, an amino group, an aldehyde group, a hydroxyl group, a thiol group, a sulfonic acid group, a carboxyl group, an alkyl group of 1 to 20 carbon atoms, alkenyl group of 2 to 20 carbon atoms or alkynyl group of 2 to 20 carbon atoms which may be substituted with $Z^{11}$, an aryl group of 6 to 20 carbon atoms or heteroaryl group of 2 to 20 carbon atoms which may be substituted with $Z^{12}$, or —NHY$^2$, —NY$^3$Y$^4$, —C(O)Y$^5$, —OY$^6$, —SY$^7$, —SO$_3$Y$^8$, —C(O)OY$^9$, —OC(O)Y$^{10}$, —C(O)NHY$^{11}$ or —C(O)NY$^{12}$Y$^{13}$ (wherein $Y^2$ to $Y^{13}$ are as defined above). These alkyl, alkenyl, alkynyl, aryl and heteroaryl groups are exemplified in the same way as above.

In particular, in formula (4), $R^{11}$ to $R^{14}$ are preferably hydrogen atoms, halogen atoms, alkyl groups of 1 to 10 carbon atoms which may be substituted with $Z^{11}$, or aryl groups of 6 to 14 carbon atoms which may be substituted with $Z^{12}$; more preferably hydrogen atoms or alkyl groups of 1 to 10 carbon atoms; and most preferably all hydrogen atoms.

$R^{15}$ and $R^{16}$ are preferably hydrogen atoms, chlorine atoms, bromine atoms, iodine atoms, alkyl groups of 1 to 10 carbon atoms which may be substituted with $Z^{11}$, aryl groups of 6 to 14 carbon atoms which may be substituted with $Z^{12}$, or diphenylamino groups which may be substituted with $Z^{12}$ (—NY$^3$Y$^4$ groups wherein $Y^3$ and $Y^4$ are phenyl groups which may be substituted with $Z^{12}$); more preferably hydrogen atoms or diphenylamino groups; and even more preferably both hydrogen atoms or both diphenylamino groups.

Of these, combinations wherein $R^{11}$ to $R^{14}$ are hydrogen atoms or alkyl groups of 1 to 10 carbon atoms, $R^{15}$ and $R^{16}$ are hydrogen atoms or diphenylamino groups, $X^1$ is —NY$^1$— or a single bond, and $Y^1$ is a hydrogen atom or a methyl group are preferred; and combinations wherein $R^{11}$ to $R^{14}$ are hydrogen atoms, $R^{15}$ and $R^{16}$ are both hydrogen atoms or both diphenylamino groups, and $X^1$ is —NH— or a single bond are more preferred.

In formula (4), $k^1$ and $k^2$ are each independently integers of 0 or more and satisfy the condition $1 \leq k^1 + k^2 \leq 20$. However, taking into account the balance between the charge transportability of the resulting thin film and the solubility of the aniline derivative, they preferably satisfy the condition $2 \leq k^1 + k^2 \leq 8$, more preferably satisfy the condition $2 \leq k^1 + k^2 \leq 6$, and even more preferably satisfy the condition $2 \leq k^1 + k^2 \leq 4$.

In particular, in $Y^1$ to $Y^{13}$ and $R^{11}$ to $R^{18}$, $Z^{11}$ is preferably a chlorine atom, a bromine atom, an iodine atom or an aryl group of 6 to 20 carbon atoms which may be substituted with $Z^{13}$, more preferably a chlorine atom, a bromine atom, an iodine atom or a phenyl group which may be substituted with $Z^{13}$, and most preferably does not exist (i.e., is non-substituting).

$Z^{12}$ is preferably a chlorine atom, a bromine atom, an iodine atom or an alkyl group of 1 to 20 carbon atoms which may be substituted with $Z^{13}$, more preferably a chlorine atom, a bromine atom, an iodine atom or an alkyl group of 1 to 4 carbon atoms which may be substituted with $Z^{13}$, and most preferably does not exist (i.e., is non-substituting).

$Z^{13}$ is preferably a chlorine atom, a bromine atom or an iodine atom, and most preferably does not exist (i.e., is non-substituting).

In $Y^1$ to $Y^{13}$ and $R^{11}$ to $R^{18}$, the number of carbon atoms on the alkyl, alkenyl and alkynyl groups is preferably 10 or less, more preferably 6 or less, and even more preferably 4 or less. The number of carbon atoms on the aryl and heteroaryl groups is preferably 14 or less, more preferably 10 or less, and even more preferably 6 or less.

Examples of methods for synthesizing the aniline derivative include, but are not particularly limited to, the methods described in *Bulletin of Chemical Society of Japan*, 67, pp. 1749-1752 (1994); *Synthetic Metals*, 84, pp. 119-120 (1997); *Thin Solid Films*, 520 (24), pp. 7157-7163 (2012); WO 2008/032617, WO 2008/032616, WO 2008/129947 and WO 2013/084664.

Illustrative examples of the aniline derivative of formula (4) include, but are not limited to, those of the following formulas. In the formulas below, DPA stands for a diphenylamino group, Ph stands for a phenyl group, and TPA stands for a p-(diphenylamino)phenyl group.

[Chemical Formula 23]

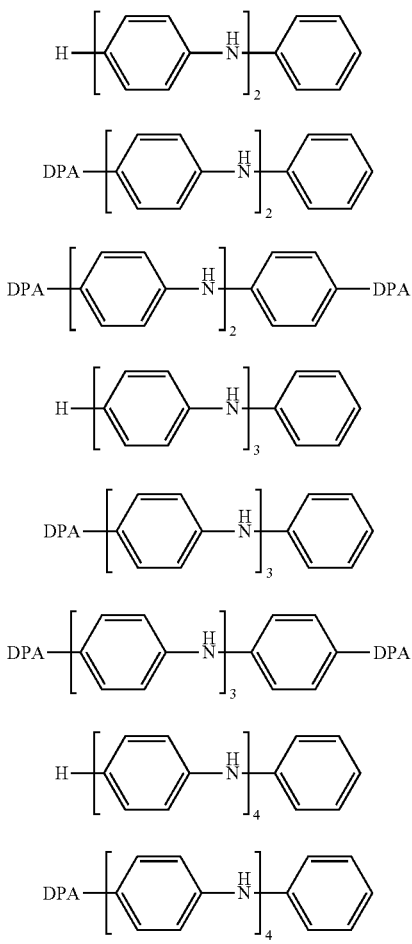

[Chemical Formula 24]

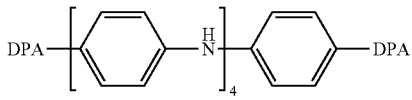

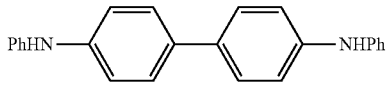

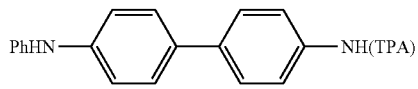

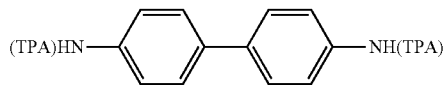

[Organic Solvent]

A high-solvency solvent capable of dissolving well the fluorine atom-containing amide compound, charge-transporting substance and dopant may be used as the organic solvent when preparing the charge-transporting varnish of the invention.

Examples of such high-solvency solvents include, but are not limited to, organic solvents such as cyclohexanone, N,N-dimethylformamide, N,N-dimethylacetamide, N,N-dimethylisobutyramide, N-methylpyrrolidone and 1,3-dimethyl-2-imidazolidinone. These solvents may be used singly or two or more may be used in admixture. The amount of use thereof may be set to from 5 to 100 wt % of the total solvent used in the varnish.

It is preferable for both the charge-transporting substance and the dopant to be either completely dissolved or in a uniformly dispersed state in this solvent, and more preferable for them to be completely dissolved in the solvent.

In the present invention, at least one type of high-viscosity organic solvent having a viscosity at 25° C. of from 10 to 200 mPa·s, especially 35 to 150 mPa·s, and a boiling point at standard pressure (atmospheric pressure) of from 50 to 300° C., especially from 150 to 250° C., may be included in the varnish. By adding such a solvent, adjusting the viscosity of the varnish is easy, making it possible to prepare a varnish which reproducibly gives thin films of high flatness and which is suitable for the method of application to be used.

Examples of high-viscosity organic solvents include, but are not limited to, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol and hexylene glycol.

The addition ratio of the high-viscosity organic solvent with respect to the overall solvent used in the varnish of the invention is preferably in a range within which the deposition of solids does not occur. An addition ratio of from 5 to 90 wt % is preferred, so long as solids do not deposit out.

In addition, another solvent may also be admixed in a ratio with respect to the overall solvent used in the varnish of from 1 to 90 wt %, and preferably from 1 to 50 wt %, for such purposes as to increase the wettability on a substrate, adjust the surface tension of the solvent, adjust the polarity, and adjust the boiling point.

Examples of such solvents include, but are not limited to, propylene glycol monomethyl ether, ethylene glycol monobutyl ether, diethylene glycol diethyl ether, diethylene glycol monomethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate and n-hexyl acetate. These solvents may be used singly or two or more may be used in admixture.

[Dopant]

Depending on the intended use of the thin film obtained therefrom, the charge-transporting varnish of the invention may include a dopant for the purpose of, e.g., increasing the charge transporting performance. The dopant is not particularly limited, so long as it is one that dissolves in at least one of the solvents used in the varnish. Both inorganic dopants and organic dopants may be used. The inorganic and organic dopants may be of one type used alone or two or more may be used in combination.

When a dopant is included in the charge-transporting varnish of the invention, the content thereof, expressed as a molar ratio with respect to the charge-transporting substance, is preferably from about 0.01 to about 20.0, and more preferably from about 0.4 to about 5.0.

Specific examples of inorganic dopants include inorganic acids such as hydrogen chloride, sulfuric acid, nitric acid and phosphoric acid; metal halides such as aluminum(III) chloride ($AlCl_3$), titanium(IV) tetrachloride ($TiCl_4$), boron tribromide ($BBr_3$), a boron trifluoride-ether complex ($BF3.OEt2$), iron(III) chloride ($FeCl_3$), copper(II) chloride ($CuCl_2$), antimony(V) pentachloride ($SbCl_5$), antimony(V) pentafluoride ($SbF_5$), arsenic(V) pentafluoride ($AsF_5$), phosphorus pentafluoride ($PF_5$) and tris(4-bromophenyl)aluminum hexachloroantimonate (TBPAH); halogens such as $Cl_2$, $Br_2$, $I_2$, ICl, $ICl_3$, IBr and $IF_4$; and heteropolyacids such as phosphomolybdic acid and phosphotungstic acid. Of these, heteropolyacids such as phosphomolybdic acid and phosphotungstic acid are preferred.

Specific examples of organic dopants include the following arylsulfone compounds: benzenesulfonic acid, tosylic acid, p-styrenesulfonic acid, 2-naphthalenesulfonic acid, 4-hydroxybenzenesulfonic acid, 5-sulfosalicylic acid, p-dodecylbenzenesulfonic acid, dihexylbenzenesulfonic acid, 2,5-dihexylbenzenesulfonic acid, dibutylnaphthalenesulfonic acid, 6,7-dibutyl-2-naphthalenesulfonic acid, dodecylnaphthalenesulfonic acid, 3-dodecyl-2-naphthalenesulfonic acid, hexylnaphthalenesulfonic acid, 4-hexyl-1-naphthalenesulfonic acid, octylnaphthalenesulfonic acid, 2-octyl-1-naphthalenesulfonic acid, hexylnaphthalenesulfonic acid, 7-hexyl-1-naphthalenesulfonic acid, 6-hexyl-2-naphthalenesulfonic acid, dinonylnaphthalenesulfonic acid, 2,7-dinonyl-4-naphthalenesulfonic acid, dinonylnaphthalenedisulfonic acid, 2,7-dinonyl-4,5-naphthalenedisulfonic acid, the 1,4-benzodioxanedisulfonic acid compounds mentioned in WO 2005/000832, the arylsulfonic acid compounds mentioned in WO 2006/025342, the arylsulfonic acid compounds mentioned in WO 2009/096352, and polystyrenesulfonic acid.

Arylsulfonic acid compounds of formula (5) or (6) below may also be advantageously used as dopants.

[Chemical Formula 25]

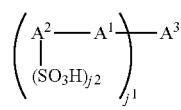

(5)

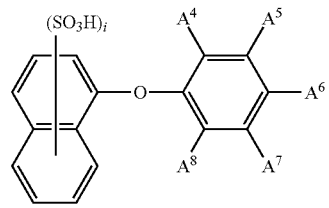

(6)

In formula (5), $A^1$ is —O— or —S—, and is preferably —O—. $A^2$ is preferably a naphthalene ring or an anthracene ring, with a naphthalene ring being preferred. $A^3$ is a divalent to tetravalent perfluorobiphenyl group, and the subscript $j^1$, which represents the number of bonds between $A^1$ and $A^3$, is an integer that satisfies the condition $2 \leq j^1 \leq 4$. It is preferable for $A^3$ to be a divalent perfluorobiphenyl group and for $j^1$ to be 2. The subscript $j^2$, which represents the number of sulfonic acid groups bonded to $A^2$, is an integer that satisfies the condition $1 \leq j^2 \leq 4$, and is preferably 2.

In formula (6), $A^4$ to $A^8$ are each independently a hydrogen atom, a halogen atom, a cyano group, an alkyl group of 1 to 20 carbon atoms, a halogenated alkyl group of 1 to 20 carbon atoms or a halogenated alkenyl group of 2 to 20 carbon atoms, with at least three of $A^4$ to $A^8$ being halogen atoms. The subscript i, which represents the number of sulfonic acid groups bonded to the naphthalene ring, is an integer that satisfies the condition $2 \leq i \leq 4$, and is preferably from 2 to 4, and more preferably 2.

Examples of halogenated alkyl groups of 1 to 20 carbon atoms include trifluoromethyl, 2,2,2-trifluoethyl, perfluoroethyl, 3,3,3-trifluoropropyl, 2,2,3,3,3-pentafluoropropyl, perfluoropropyl, 4,4,4-trifluorobutyl, 3,3,4,4,4-pentafluorobutyl, 2,2,3,3,4,4,4-heptafluorobutyl and perfluorobutyl groups.

Examples of halogenated alkenyl groups of 2 to 20 carbon atoms include perfluorovinyl, 1-perfluoropropenyl, perfluoroallyl and perfluorobutenyl groups.

The halogen atom and the alkyl group of 1 to 20 carbon atoms are exemplified in the same way as above, with the halogen atom preferably being a fluorine atom.

Of these, $A^4$ to $A^8$ are preferably hydrogen atoms, halogen atoms, cyano groups, alkyl groups of 1 to 10 carbon atoms, halogenated alkyl groups of 1 to 10 carbon atoms or halogenated alkenyl groups of 2 to 10 carbon atoms, with at least three of $A^4$ to $A^8$ being fluorine atoms; more preferably hydrogen atoms, fluorine atoms, cyano groups, alkyl groups of 1 to 5 carbon atoms, fluorinated alkyl groups of 1 to 5 carbon atoms or fluorinated alkenyl groups of 2 to 5 carbon atoms, with at least three of $A^4$ to $A^8$ being fluorine atoms; and even more preferably hydrogen atoms, fluorine atoms, cyano groups, perfluoroalkyl groups of 1 to 5 carbon atoms or perfluoroalkenyl groups of 1 to 5 carbon atoms, with $A^4$, $A^5$ and $A^8$ being fluorine atoms.

Here, "perfluoroalkyl group" refers to a group in which all hydrogen atoms on an alkyl group are substituted with fluorine atoms, and "perfluoroalkenyl group" refers to a group in which all hydrogen atoms on an alkenyl group are substituted with fluorine atoms.

Arylsulfonic acid compounds of formula (7) below can also be suitably used as dopants.

[Chemical Formula 26]

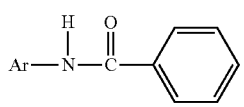

(7)

In the formula, Ar is a group of formula (8) or (9)

[Chemical Formula 27]

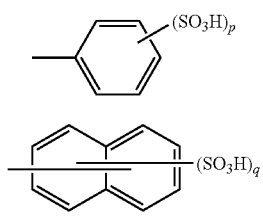

(8)

(9)

(wherein p is an integer from 1 to 5, and q is an integer from 1 to 7).

The arylsulfonic acid compound of formula (7) can be obtained by reacting an amine compound of formula (10) with an acid halide of formula (11) to form an arylsulfonic acid salt of formula (7'), and then subjecting this salt to ion exchange treatment.

[Chemical Formula 28]

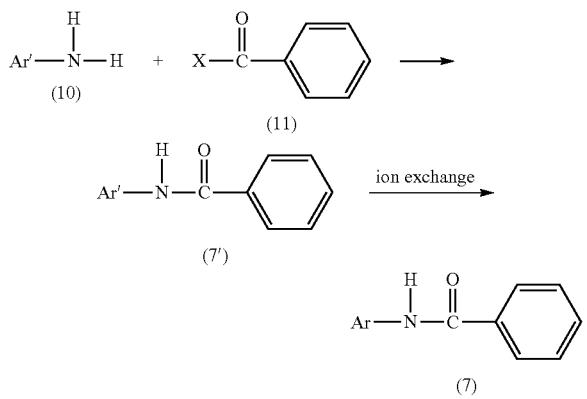

In these formulas, Ar and X are the same as above, and Ar' represents a group of formula (8') or (9')

[Chemical Formula 29]

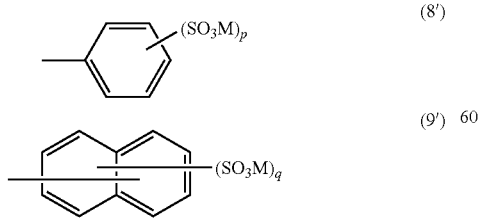

(8')

(9')

(wherein p and q are the same as above, and M is an alkali metal atom such as sodium or potassium).

Examples of the amine compound of formula (10) include, but are not limited to, disodium aniline-2,4-disulfonate, disodium aniline-2,5-disulfonate, disodium 8-aminonaphthalene-1,5-disulfonate, disodium 2-aminonaphthalene-1,5-disulfonate, disodium 2-aminonaphthalene-3,6-disulfonate, disodium 7-aminonaphthalene-1,5-disulfonate, disodium 7-aminonaphthalene-2,4-disulfonate and disodium 7-aminonaphthalene-1,3-disulfonate. A hydrate may be used as the amine compound of formula (10).

Examples of the acid halide of formula (11) include benzoyl chloride and benzoyl bromide.

The reaction solvent is preferably an aprotic polar organic solvent, examples of which include N,N-dimethylformamide, N,N-dimethylacetamide, N-methylpyrrolidone, 1,3-dimethyl-2-imidazolidinone, dimethylsulfoxide, tetrahydrofuran and dioxane. From the standpoint of the ease of removing the reaction solvent following the reaction, N,N-dimethylformamide, N,N-dimethylacetamide, tetrahydrofuran and dioxane are preferred.

The reaction temperature may be generally from −50° C. to the boiling point of the solvent used, although the range of 0° C. to 140° C. is preferred. The reaction time is generally from 0.1 to 100 hours.

After reaction completion, the arylsulfonic acid salt of formula (7') is recovered by filtration, removal of the reaction solvent by distillation or the like, following which the arylsulfonic acid compound of formula (7) can be prepared by protonation of the sulfonic acid salt with a cation-exchange resin.

The acid halide of formula (11) can be obtained by reacting benzoic acid with, for example, an electrophilic halide such as thionyl chloride, oxalyl chloride, phosphoryl chloride, sulfuryl chloride, phosphorus trichloride or phosphorus pentachloride.

Examples of preferred dopants include, but are not limited to, phosphomolybdic acid, phosphotungstic acid and the compounds shown below.

[Chemical Formula 30]

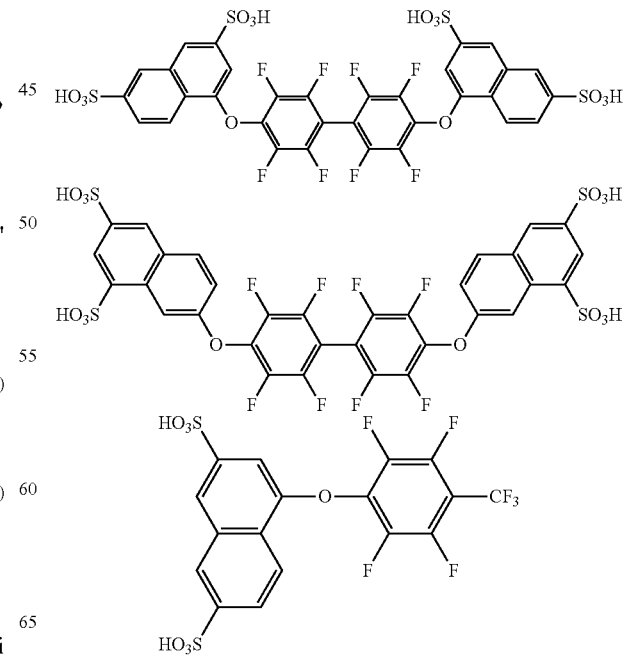

-continued

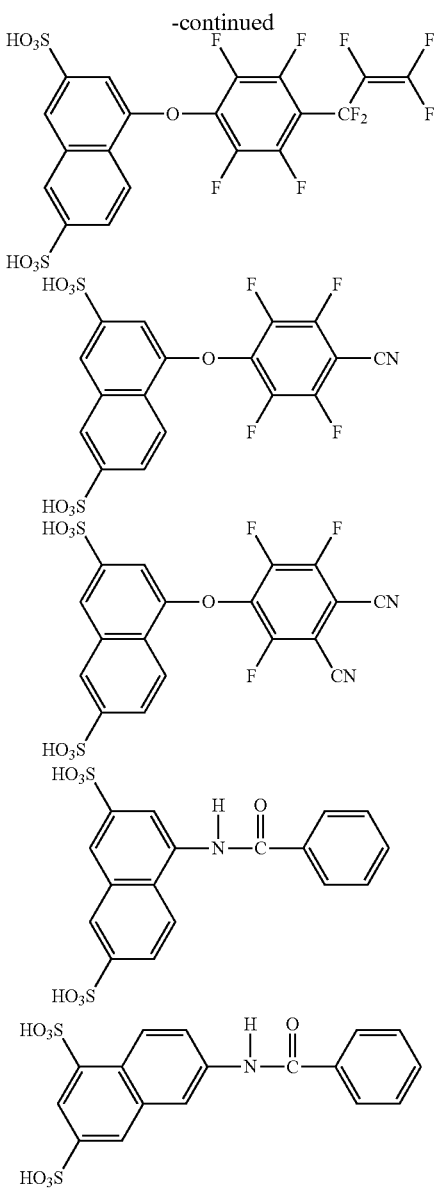

The method of preparing the charge-transporting varnish is exemplified by, but not particularly limited to, a method in which the fluorine atom-containing amide compound of the invention, a charge-transporting substance, a dopant and the like are dissolved in a high-solvency solvent, and a high-viscosity organic solvent is added thereto; and a method in which a high-solvency solvent and a high-viscosity organic solvent are mixed together, and the fluorine atom-containing amide compound of the invention, a charge-transporting substance, a dopant and the like are dissolved therein.

In this invention, from the standpoint of reproducibly obtaining thin films of a higher flatness, it is desirable for the charge-transporting varnish, following dissolution of the fluorine atom-containing amide compound of the invention, charge-transporting substance, dopant and the like in an organic solvent, to be filtered using a submicron order filter or the like.

From the standpoint of ensuring a sufficient film thickness while suppressing precipitation of the charge-transporting substance, the solids concentration in the varnish of the invention is generally from about 0.1 to about 20 wt %, and preferably from 0.5 to 10 wt %. The content of the fluorine atom-containing amide compound in the varnish of the invention is generally from about 0.01 to about 100 wt %, and preferably from about 0.1 to about 50 wt %, of the solids. As used herein, "solids" refers to the ingredients that remain after the solvents are removed from the ingredients included in the varnish. The varnish at 25° C. of the invention has a viscosity of generally from 1 to 50 mPa·s.

[Charge-Transporting Thin Film]

A charge-transporting thin film can be formed on a substrate by coating the charge-transporting varnish of the invention onto the substrate and baking.

Examples of the varnish coating method include, but are not limited to, dipping, spin coating, transfer printing, roll coating, brush coating, inkjet printing, spraying and slit coating. It is preferable for the viscosity and surface tension of the varnish to be adjusted according to the coating method.

When using the varnish of the invention, the baking atmosphere is not particularly limited. A thin film having a uniform film surface and charge transportability can be obtained not only in an open-air atmosphere, but even in an inert gas such as nitrogen or in a vacuum. However, from the standpoint of reproducibly obtaining a thin film having a high charge transportability, an open-air atmosphere is preferred.

The baking temperature is suitably set in the range of about 100 to about 260° C. while taking into account such factors as the intended use of the resulting thin film and the degree of charge transportability to be imparted to the thin film. When the thin film thus obtained is to be used as a hole-injecting layer in an organic EL device, the baking temperature is preferably from about 140° C. to about 250° C., and more preferably from about 145° C. to about 240° C.

The baking time varies depending on the baking temperature and therefore cannot be strictly specified, although the baking time is generally from about one minute to about one hour.

During baking, a temperature change in two or more steps may be applied for such purposes as to achieve even more uniform film formability or to cause the reaction to proceed on the substrate. Heating may be carried out using a suitable apparatus such as a hot plate or an oven.

The thickness of the charge-transporting thin film is not particularly limited. However, when the thin film is to be used as a hole-injecting layer in an organic EL device, a film thickness of from 5 to 200 nm is preferred. Methods for changing the film thickness include, for example, changing the solids concentration in the varnish and changing the amount of solution on the substrate during coating.

The charge-transporting thin film of the invention can be suitably used as a hole-injecting layer in an organic EL device, although use as a charge-transporting functional layer such as a hole-injecting-and-transporting layer is also possible.

[Organic EL Element]

The organic EL device of the invention has a pair of electrodes and, between these electrodes, the above-described charge-transporting thin-film of the invention.

Typical organic EL device configurations include, but are not limited to, those of (a) to (f) below. In these configurations, where necessary, an electron-blocking layer or the like may be provided between the light-emitting layer and the anode, and a hole-blocking layer or the like may be provided between the light-emitting layer and the cathode. Alternatively, the hole-injecting layer, hole-transporting layer or hole-injecting-and-transporting layer may also have the function of, for example, an electron-blocking layer; and the electron-injecting layer, electron-transporting layer or electron-injecting-and-transporting layer may also have the function of, for example, a hole-blocking layer.

(a) anode/hole-injecting layer/hole-transporting layer/light-emitting layer/electron-transporting layer/electron-injecting layer/cathode
(b) anode/hole-injecting layer/hole-transporting layer/light-emitting layer/electron-injecting-and-transporting layer/cathode
(c) anode/hole-injecting-and-transporting layer/light-emitting layer/electron-transporting layer/electron-injecting layer/cathode
(d) anode/hole-injecting-and-transporting layer/light-emitting layer/electron-injecting-and-transporting layer/cathode
(e) anode/hole-injecting layer/hole-transporting layer/light-emitting layer/cathode
(f) anode/hole-injecting-and-transporting layer/light-emitting layer/cathode As used herein, "hole-injecting layer," "hole-transporting layer" and "hole-injecting-and-transporting layer" refer to layers which are formed between the light-emitting layer and the anode, and which have the function of transporting holes from the anode to the light-emitting layer. When only one layer of hole-transporting material is provided between the light-emitting layer and the anode, this is a "hole-injecting-and-transporting layer"; when two or more layers of hole-transporting material are provided between the light-emitting layer and the anode, the layer that is closer to the anode is a "hole-injecting layer" and the other layer is a "hole-transporting layer." In particular, a thin-film having not only an ability to receive holes from the anode but also an excellent ability to inject holes into the hole-transporting layer or the light-emitting layer may be used as, respectively, the hole-injecting layer or the hole-injecting-and-transporting layer.

In addition, "electron-injecting layer," "electron-transporting layer" and "electron-injecting-and-transporting layer" refer to layers which are formed between the light-emitting layer and the cathode, and which have the function of transporting electrons from the cathode to the light-emitting layer. When only one layer of electron-transporting material is provided between the light-emitting layer and the cathode, this is an "electron-injecting-and-transporting layer"; when two or more layers of electron-transporting material are provided between the light-emitting layer and the cathode, the layer that is closer to the cathode is an "electron-injecting layer" and the other layer is an "electron-transporting layer."

The "light-emitting layer" is an organic layer having a light-emitting function. When a doping system is used, this layer includes a host material and a dopant material. The function of the host material is primarily to promote the recombination of electrons and holes, and to confine the resulting excitons within the light-emitting layer. The function of the dopant material is to cause the excitons obtained by recombination to efficiently luminesce. In the case of a phosphorescent device, the host material functions primarily to confine within the light-emitting layer the excitons generated by the dopant.

The materials and method employed to fabricate an organic EL device using the charge-transporting varnish of the invention are exemplified by, but not limited to, those described below.

The electrode substrate to be used is preferably cleaned beforehand by liquid washing with, for example, a cleaning agent, alcohol or pure water. When the substrate is an anode substrate, it is preferably subjected to surface treatment such as UV/ozone treatment or oxygen-plasma treatment just prior to use. However, surface treatment need not be carried out if the anode material is composed primarily of organic substances.

An example of a method of fabricating an inventive organic EL device in which a thin-film obtained from the charge-transporting varnish of the invention serves as a hole-injecting layer is described below.

As described above, a hole-injecting layer is formed on an electrode by applying the charge-transporting varnish of the invention onto an anode substrate and baking. A hole-transporting layer, a light-emitting layer, an electron-transporting layer, an electron-injecting layer and a cathode are then provided in this order on the hole-injecting layer. The hole-transporting layer, light-emitting layer, electron-transporting layer and electron-injecting layer may each be formed by a vapor deposition process or a coating process (wet process), depending on the properties of the material to be used.

Illustrative examples of anode materials include transparent electrodes such as indium-tin oxide (ITO) and indium-zinc oxide (IZO), and metal anodes made of a metal such as aluminum or an alloy of such a metal. An anode material on which planarizing treatment has been carried out is preferred. Use can also be made of polythiophene derivatives and polyaniline derivatives having high charge transportability.

Examples of other metals making up the metal anode include, but are not limited to, scandium, titanium, vanadium, chromium, manganese, iron, cobalt, nickel, copper, zinc, gallium, yttrium, zirconium, niobium, molybdenum, ruthenium, rhodium, palladium, cadmium, indium, scandium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof.

Specific examples of hole-transporting layer-forming materials include the following hole-transporting low-molecular-weight materials: triarylamines such as (triphenylamine) dimer derivatives, [(triphenylamine) dimer] spirodimer, N,N'-bis(naphthalen-1-yl)-N,N'-bis(phenyl)benzidine (α-NPD), N,N'-bis(naphthalen-2-yl)-N,N'-bis(phenyl)benzidine, N,N'-bis(3-methylphenyl)-N,N'-bis(phenyl) benzidine, N,N'-bis(3-methylphenyl)-N,N'-bis(phenyl)-9,9-spirobifluorene, N,N'-bis(naphthalen-1-yl)-N,N'-bis(phenyl)-9,9-spirobifluorene, N,N'-bis(3-methylphenyl)-N,N'-bis(phenyl)-9,9-dimethylfluorene, N,N'-bis(naphthalen-1-yl)-N,N'-bis(phenyl)-9,9-dimethylfluorene, N,N'-bis(3-methylphenyl)-N,N'-bis(phenyl)-9,9-diphenylfluorene, N,N'-bis(naphthalen-1-yl)-N,N'-bis(phenyl)-9,9-diphenylfluorene, N,N'-bis(naphthalen-1-yl)-N,N'-bis(phenyl)-2,2'-dimethylbenzidine, 2,2',7,7'-tetrakis(N,N-diphenylamino)-9,9-spirobifluorene, 9,9-bis[4-(N,N-bisbiphenyl-4-ylamino) phenyl]-9H-fluorene, 9,9-bis[4-(N,N-bisnaphthalen-2-ylamino)phenyl]-9H-fluorene, 9,9-bis[4-(N-naphthalen-1-yl-N-phenylamino)phenyl]-9H-fluorene, 2,2',7,7'-tetrakis[N-naphthalenyl(phenyl)amino]-9,9-spirobifluorene, N,N'-bis(phenanthren-9-yl)-N,N'-bis(phenyl)benzidine, 2,2'-bis[N,N-bis(biphenyl-4-yl)amino]-9,9-spirobifluorene, 2,2'-bis(N,N-diphenylamino)-9,9-spirobifluorene, di[4-(N,N-di(p-tolyl)amino)phenyl]cyclohexane, 2,2',7,7'-tetra(N,N-di(p-tolyl))amino-9,9-spirobifluorene, N,N,N',N'- tetranaphthalen-2-ylbenzidine, N,N,N',N'-tetra(3-methylphenyl)-3,3'-dimethylbenzidine, N,N'-di(naphthalenyl)-N,N'-di(naphthalen-2-yl)benzidine, N,N,N',N'-tetra(naphthalenyl)benzidine, N,N'-di(naphthalen-2-yl)-N,N'-diphenylbenzidine-1-4-diamine, $N^1,N^4$-diphenyl-$N^1$, $N^4$-di(m-tolyl)benzene-1,4-diamine, $N^2,N^2,N^6,N^6$-tetraphenylnaphthalene-2,6-diamine, tris(4-(quinolin-8-yl)phenyl)amine, 2,2'-bis(3-(N,N-di(p-tolyl)amino)phenyl)biphenyl, 4,4',4''-tris[3-methylphenyl(phenyl)amino triphenylamine (m-MTDATA) and 4,4',4''-tris[1-naphthyl(phenyl)amino]triphenylamine (1-TNATA); and oligothiophenes such as 5,5''-bis-{4-[bis(4-methylphenyl)amino]phenyl}-2,2':5',2''-terthiophene (BMA-3T).

Specific examples of light-emitting layer-forming materials include tris(8-quinolinolate) aluminum(III) ($Alq_3$), bis(8-quinolinolate) zinc(II) ($Zna_2$), bis(2-methyl-8-quinolinolate)-4-(p-phenylphenolate) aluminum(III) (BAlq), 4,4'-bis(2,2-diphenylvinyl)biphenyl, 9,10-di(naphthalen-2-yl)anthracene, 2-t-butyl-9,10-di(naphthalen-2-yl)anthracene, 2,7-bis[9,9-di(4-methylphenyl)fluoren-2-yl]-9,9-di(4-methylphenyl)fluorene, 2-methyl-9,10-bis(naphthalen-2-yl)anthracene, 2-(9,9-spirobifluoren-2-yl)-9,9-spirobifluorene, 2,7-bis(9,9-spirobifluoren-2-yl)-9,9-spirobifluorene, 2-[9,9-di(4-methylphenyl)fluoren-2-yl]-9,9-di(4-methylphenyl)fluorene, 2,2'-dipyrenyl-9,9-spirobifluorene, 1,3,5-tris(pyren-1-yl)benzene, 9,9-bis[4-(pyrenyl)phenyl]-9H-fluorene, 2,2'-bi(9,10-diphenylanthracene), 2,7-dipyrenyl-9,9-spirobifluorene, 1,4-di(pyren-1-yl)benzene, 1,3-di(pyren-1-yl)benzene, 6,13-di(biphenyl-4-yl)pentacene, 3,9-di(naphthalen-2-yl)perylene, 3,10-di(naphthalen-2-yl)perylene, tris[4-(pyrenyl)phenyl]amine, 10,10'-di(biphenyl-4-yl)-9,9'-bianthracene, N,N'-di(naphthalen-1-yl)-N,N'-diphenyl[1,1':4',1'':4'',1'''-quaterphenyl]-4,4'''-diamine, 4,4'-di[10-(naphthalen-1-yl)anthracen-9-yl]biphenyl, dibenzo{[f,f]-4,4',7,7'-tetraphenyl}diindeno[1,2,3-cd:1',2',3'-1m]perylene, 1-(7-(9,9'-bianthracen-10-yl)-9,9-dimethyl-9H-fluoren-2-yl)pyrene, 1-(7-(9,9'-bianthracen-10-yl)-9,9-dihexyl-9H-fluoren-2-yl)pyrene, 1,3-bis(carbazol-9-yl)benzene, 1,3,5-tris(carbazol-9-yl)benzene, 4,4',4''-tris(carbazol-9-yl)triphenylamine, 4,4'-bis(carbazol-9-yl)biphenyl (CBP), 4,4'-bis(carbazol-9-yl)-2,2'-dimethylbiphenyl, 2,7-bis(carbazol-9-yl)-9,9-dimethylfluorene, 2,2',7,7'-tetrakis(carbazol-9-yl)-9,9-spirobifluorene, 2,7-bis(carbazol-9-yl)-9,9-di(p-tolyl)fluorene, 9,9-bis[4-(carbazol-9-yl)phenyl]fluorene, 2,7-bis(carbazol-9-yl)-9,9-spirobifluorene, 1,4-bis(triphenylsilyl)benzene, 1,3-bis(triphenylsilyl)benzene, bis(4-N,N-diethylamino-2-methylphenyl)-4-methylphenylmethane, 2,7-bis(carbazol-9-yl)-9,9-dioctylfluorene, 4,4''-di(triphenylsilyl)-p-terphenyl, 4,4'-di(triphenylsilyl)biphenyl, 9-(4-t-butylphenyl)-3,6-bis(triphenylsilyl)-9H-carbazole, 9-(4-t-butylphenyl)-3,6-ditrityl-9H-carbazole, 9-(4-t-butylphenyl)-3,6-bis(9-(4-methoxyphenyl)-9H-fluoren-9-yl)-9H-carbazole, 2,6-bis(3-(9H-carbazol-9-yl)phenyl)pyridine, triphenyl(4-(9-phenyl-9H-fluoren-9-yl)phenyl)silane, 9,9-dimethyl-N,N-diphenyl-7-(4-(1-phenyl-1H-benzo[d]imidazol-2-yl)phenyl-9H-fluoren-2-amine, 3,5-bis(3-(9H-carbazol-9-yl)phenyl)pyridine, 9,9-spirobifluoren-2-yldiphenylphosphine oxide, 9,9'-(5-triphenylsilyl)-1,3-phenylene)bis(9H-carbazole), 3-(2,7-bis(diphenylphosphoryl)-9-phenyl-9H-fluoren-9-yl)-9-phenyl-9H-carbazole, 4,4,8,8,12,12-hexa(p-tolyl)-4H-8H-12H-12C-azadibenzo[cd,mn]pyrene, 4,7-di(9H-carbazol-9-yl)-1,10-phenanthroline, 2,2'-bis(4-(carbazol-9-yl)phenyl)biphenyl, 2,8-bis(diphenylphosphoryl)dibenzo[b,d]thiophene, bis(2-methylphenyl)diphenylsilane, bis[3,5-di(9H-carbazol-9-yl)phenyl]diphenylsilane, 3,6-bis(carbazol-9-yl)-9-(2-ethylhexyl)-9H-carbazole, 3-(diphenylphosphoryl)-9-(4-(diphenylphosphoryl)phenyl)-9H-carbazole and 3,6-bis[(3,5-diphenyl)phenyl]-9-phenyl-carbazole. A light-emitting layer may be formed by co-vapor deposition of any of these materials with a light-emitting dopant.

Specific examples of light-emitting dopants include 3-(2-benzothiazolyl)-7-(diethylamino)coumarin, 2,3,6,7-tetrahydro-1,1,7,7-tetramethyl-1H,5H,11H-10-(2-benzothiazolyl)quinolidino-[9,9a,1gh]coumarin, quinacridone, N,N'-dimethylquinacridone, tris(2-phenylpyridine) iridium(III) ($Ir(ppy)_3$), bis(2-phenylpyridine)(acetylacetonate) iridium (III) ($Ir(ppy)_2(acac)$), tris[2-(p-tolyl)pyridine) iridium(III) ($Ir(mppy)_3$), 9,10-bis[N,N-di(p-tolyl)amino]anthracene, 9,10-bis[phenyl(m-tolyl)amino]anthracene, bis[2-(2-hydroxyphenyl)benzothiazolate]zinc(II), $N^{10},N^{10},N^{10},N^{10}$-tetra(p-tolyl)-9,9'-bianthracene-10,10'-diamine, $N^{10},N^{10}$, $N^{10},N^{10}$-tetraphenyl-9,9'-bianthracene-10,10'-diamine, $N^{10}$, $N^{10}$-diphenyl-$N^{10},N^{10}$-dinaphthalenyl-9,9'-bianthracene-10,10'-diamine, 4,4'-bis(9-ethyl-3-carbazovinylene)-1,1'-biphenyl, perylene, 2,5,8,11-tetra-t-butylperylene, 1,4-bis[2-(3-N-ethylcarbazolyl)vinyl]benzene, 4,4'-bis[4-(di-p-tolylamino)styryl]biphenyl, 4-(di-p-tolylamino)-4'-[(di-p-tolylamino)styryl]stilbene, bis[3,5-difluoro-2-(2-pyridyl)phenyl-(2-carboxypyridyl)]iridium(III), 4,4'-bis[4-(diphenylamino)styryl]biphenyl, bis(2,4-difluorophenylpyridinato)tetrakis(1-pyrazolyl)borate iridium(III), N,N'-bis(naphthalen-2-yl)-N,N'-bis(phenyl)tris(9,9-dimethylfluorenylene), 2,7-bis{2-[phenyl(m-tolyl)amino]-9,9-dimethylfluoren-7-yl}-9,9-dimethylfluorene, N-(4-((E)-2-(6((E)-4-(diphenylamino)styrylnaphthalen-2-yl)vinyl)phenyl)-N-phenylbenzenamine, fac-iridium(III) tris(1-phenyl-3-methylbenzimidazolin-2-ylidene-$C,C^2$), mer-iridium(III) tris(1-phenyl-3-methylbenzimidazolin-2-ylidene-$C,C^2$), 2,7-bis[4-(diphenylamino)styryl]-9,9-spirobifluorene, 6-methyl-2-(4-(9-(4-(6-methylbenzo[d]thiazol-2-yl)phenyl)anthracen-10-yl)phenyl)-benzo[d]thiazole, 1,4-di[4-(N,N-diphenyl)amino]styrylbenzene, 1,4-bis(4-(9H-carbazol-9-yl)styryl)benzene, (E)-6-(4-(diphenylamino)styryl)-N,N-diphenylnaphthalen-2-amine, bis(2,4-difluorophenylpyridinato)(5-(pyridin-2-yl)-1H-tetrazolate) iridium(III), bis(3-trifluoromethyl-5-(2-pyridyl)pyrazole)((2,4-difluorobenzyl)diphenylphosphinate) iridium(III), bis(3-trifluoromethyl-5-(2-pyridyl)pyrazolate)(benzyldiphenylphosphinate) iridium(III), bis(1-(2,4-difluorobenzyl)-3-methylbenzimidazolium)(3-(trifluoromethyl)-5-(2-pyridyl)-1,2,4-triazolate) iridium(III), bis(3-trifluoromethyl-5-(2-pyridyppyrazolate)(4',6'-difluorophenylpyridinate) iridium (III), bis(4',6'-difluorophenylpyridinato)(3,5-bis(trifluoromethyl)-2-(2'-pyridyl)pyrrolate) iridium(III), bis(4',6'-difluorophenylpyridinato)(3-(trifluoromethyl)-5-(2-pyridyl)-1,2,4-triazolate) iridium (III), (Z)-6-mesityl-N-(6-mesitylquinolin-2(1H)-ylidene)quinoline-2-amine-$BF_2$, (E)-2-(2-(4-(dimethylamino)styryl)-6-methyl-4H-pyran-4-ylidene)malononitrile, 4-(dicyanomethylene)-2-methyl-6-julolidyl-9-enyl-4-H-pyran, 4-(dicyanomethylene)-2-methyl-6-(1,1,7,7-tetramethyljulolidyl-9-enyl)-4H-pyran, 4-(dicyanomethylene)-2-t-butyl-6-(1,1,7,7-tetramethyljulolidin-4-ylvinyl)-4H-pyran, tris(dibenzoylmethane)phenanthroline europium(III), 5,6,11,12-tetraphenylnaphthacene, bis(2-benzo[b]thiophen-2-yl-pyridine)(acetylacetonate) iridium(III), tris(1-phenylisoquinoline) iridium(III), bis(1-phenylisoquinoline)(acetylacetonate) iridium(III), bis[1-(9,9-dimethyl-9H-fluoren-2-yl)isoquinoline](acetylacetonate) iridium(III), bis[2-(9,9-dimethyl-9H-fluoren-2-yl)quinoline](acetylacetonate) iridium(III), tris[4,4'-di-t-butyl-(2,2')-bipyridine] ruthenium(III)-bis(hexafluorophosphate), tris(2- phenylquinoline) iridium(III), bis(2-phenylquinoline) (acetylacetonate) iridium(III), 2,8-di-t-butyl-5,11-bis(4-t-butylphenyl)-6,12-diphenyltetracene, bis(2-phenylbenzothiazolate)(acetylacetonate) iridium(III), platinum 5,10,15,20-tetraphenyltetrabenzoporphyrin, osmium(II) bis(3-trifluoromethyl-5-(2-pyridine)pyrazolate)dimethylphenylphosphine, osmium(II) bis(3-trifluoromethyl)-5-(4-t-butylpyridyl)-1,2,4-triazolate)diphenylmethylphosphine, osmium(II) bis(3-(trifluoromethyl)-5-(2-pyridyl)-1,2,4-triazole)dimethylphenylphosphine, osmium (II) bis(3-(trifluoromethyl)-5-(4-t-butylpyridyl)-1,2,4-triazolate)dimethylphenyl-phosphine, bis[2-(4-n-hexylphenyl)quinoline](acetylacetonate) iridium(III), tris[2-(4-n-hexylphenyequinoline] iridium(III), tris[2-phenyl-4-methylquinoline] iridium(III), bis(2-phenylquinoline)(2-(3-methylphenyl)pyridinate) iridium(III), bis(2-(9,9-diethylfluoren-2-yl)-1-phenyl-1H-benzo[d]imidazolato) (acetylacetonate) iridium(III), bis(2-phenylpyridine)(3-(pyridin-2-yl)-2H-chromen-9-onate) iridium(III), bis(2-phenylquinoline)(2,2,6,6-tetramethylheptane-3,5-dionate) iridium(III), bis(phenylisoquinoline)(2,2,6,6-tetramethylheptane-3,5-dionate) iridium(III), iridium(III) bis(4-phenylthieno[3,2-c]pyridinato-N,$C^2$)acetylacetonate, (E)-2-(2-t-butyl-6-(2-(2,6,6-trimethyl-2,4,5,6-tetrahydro-1H-pyrrolo[3,2,1-ij]quinolin-8-yl)vinyl)-4H-pyran-4-ylidene) malononitrile, bis(3-trifluoromethyl-5-(1-isoquinolyl) pyrazolate)(methyldiphenylphosphine) ruthenium, bis[(4-n-hexylphenyl)isoquinoline](acetylacetonate) iridium(III), platinum(II) octaethylporphin, bis(2-methyldibenzo[f,h]quinoxaline)(acetylacetonate) iridium(III) and tris[(4-n-hexylphenyl)isoquinoline] iridium(III).

Specific examples of electron-transporting layer-forming materials include lithium 8-hydroxyquinolinate, 2,2',2"-(1,3,5-benzinetriyl)-tris(1-phenyl-1-H-benzimidazole), 2-(4-biphenyl)-5-(4-t-butylphenyl)-1,3,4-oxadiazole, 2,9-dimethyl-4,7-diphenyl-1,10-phenanthroline, 4,7-diphenyl-1,10-phenanthroline, bis(2-methyl-8-quinolinolate)-4-(phenylphenolato)aluminum, 1,3-bis[2-(2,2'-bipyridin-6-yl)-1,3,4-oxadiazo-5-yl]benzene, 6,6'-bis[5-(biphenyl-4-yl)-1,3,4-oxadiazo-2-yl]-2,2'-bipyridine, 3-(4-biphenyl)-4-phenyl-5-t-butylphenyl-1,2,4-triazole, 4-(naphthalen-1-yl)-3,5-diphenyl-4H-1,2,4-triazole, 2,9-bis(naphthalen-2-yl)-4,7-diphenyl-1,10-phenanthroline, 2,7-bis[2-(2,2'-bipyridin-6-yl)-1,3,4-oxadiazo-5-yl]-9,9-dimethylfluorene, 1,3-bis[2-(4-t-butylphenyl)-1,3,4-oxadiazo-5-yl]benzene, tris(2,4,6-trimethyl-3-(pyridin-3-yl)phenyl)borane, 1-methyl-2-(4-(naphthalen-2-yl)phenyl)-1H-imidazo[4,5f][1,10] phenanthroline, 2-(naphthalen-2-yl)-4,7-diphenyl-1,10-phenanthroline, phenyldipyrenylphosphine oxide, 3,3',5,5'-tetra[(m-pyridyl)phen-3-yl]biphenyl, 1,3,5-tris[(3-pyridyl)phen-3-yl]benzene, 4,4'-bis(4,6-diphenyl-1,3,5-triazin-2-yl)biphenyl, 1,3-bis[3,5-di(pyridin-3-yl)phenyl]benzene, bis(10-hydroxybenzo[h]quinolinato)beryllium, diphenylbis(4-(pyridin-3-yl)phenyl)silane and 3,5-di(pyren-1-yl)pyridine.

Examples of electron-injecting layer-forming materials include lithium oxide ($Li_2O$), magnesium oxide (MgO), alumina ($Al_2O_3$), lithium fluoride (LiF), sodium fluoride (NaF), magnesium fluoride ($MgF_2$), cesium fluoride (CsF), strontium fluoride ($SrF_2$), molybdenum trioxide ($MoO_3$), aluminum, lithium acetylacetonate Li(acac), lithium acetate and lithium benzoate.

Examples of cathode materials include aluminum, magnesium-silver alloys, aluminum-lithium alloys, lithium, sodium, potassium and cesium.

In cases where the thin film obtained from the charge-transporting varnish of the invention is a hole-injecting layer, another example of a method of fabricating the organic EL device of the invention is as follows.

An organic EL device having a charge-transporting thin film formed using the charge-transporting varnish of the invention can be produced by, in the fabrication of an organic EL device as described above, successively forming a hole-transporting layer and a light-emitting layer instead of carrying out vacuum evaporation operations for a hole-transporting layer, a light-emitting layer, an electron-transporting layer and an electron-injecting layer. Specifically, the charge-transporting varnish of the invention is applied onto an anode substrate, and a hole-injecting layer is formed by the above-described method. A hole-transporting layer and a light-emitting layer are then successively formed thereon, following which a cathode material is vapor-deposited on top, thereby giving an organic EL device.

The cathode and anode materials used here may be similar to those described above, and similar cleaning treatment and surface treatment may be carried out.

The method of forming the hole-transporting layer and the light-emitting layer is exemplified by a film-forming method that entails adding a solvent to a hole-transporting polymer material or a light-emitting polymer material, or to a material obtained by adding a dopant to these, thereby dissolving or uniformly dispersing the material, and then applying the resulting solution or dispersion onto, respectively, the hole-injecting layer or the hole-transporting layer and subsequently baking the applied layer.

Examples of hole-transporting polymer materials include poly[(9,9-dihexylfluorenyl-2,7-diyl)-co-(N,N'-bis{p-butylphenyl}-1,4-diaminophenylene)], poly[(9,9-dioctylfluorenyl-2,7-diyl)-co-(N,N'-bis{p-butylphenyl}-1,1-biphenylene-4,4-diamine)], poly[(9,9-bis{1'-penten-5'-yl}fluorenyl-2,7-diyl)-co-(N,N'-bis{p-butylphenyl}-1,4-diaminophenylene)], poly[N,N'-bis(4-butylphenyl)-N,N'-bis(phenyl)benzidine] end-capped with polysilsesquioxane and poly[(9,9-dioctylfluorenyl-2,7-diyl)-co-(4,4'-(N-(p-butylphenyl))diphenylamine)].

Examples of light-emitting polymer materials include polyfluorene derivatives such as poly(9,9-dialkylfluorene) (PDAF), poly(phenylene vinylene) derivatives such as poly (2-methoxy-5-(2'-ethylhexoxy)-1,4-phenylene vinylene) (MEH-PPV), polythiophene derivatives such as poly(3-alkylthiophene) (PAT), and polyvinylcarbazole (PVCz).

Examples of the solvent include toluene, xylene and chloroform. Examples of the method of dissolution or uniform dispersion include stirring, stirring under applied heat, and ultrasonic dispersion.

Examples of the coating method include, but are not particularly limited to, inkjet printing, spraying, dipping, spin coating, transfer printing, roll coating and brush coating. Coating is preferably carried out in an inert gas atmosphere such as nitrogen or argon.

Examples of the baking method include methods that involve heating in an oven or on a hot plate, either within an inert gas atmosphere or in a vacuum.

An example is described below of a method of fabricating the organic EL device of the invention in a case where the thin film obtained from the charge-transporting varnish of the invention is a hole-injecting-and-transporting layer.

A hole-injecting-and-transporting layer is formed on an anode substrate, and a light-emitting layer, an electron-transporting layer, an electron-injecting layer and a cathode are provided in this order on the hole-injecting-and-transporting layer. Methods of forming the light-emitting layer, electron-transporting layer and electron-injecting layer, and specific examples of each, are exemplified in the same way as above.

The anode material, the materials which form the light-emitting layer, the light-emitting dopant, the electron-transporting layer and the electron-blocking layer, and the cathode material are exemplified in the same way as above.

A hole-blocking layer, an electron-blocking layer or the like may be optionally provided between the electrodes and any of the above layers. By way of illustration, an example of a material that forms an electron-blocking layer is tris (phenylpyrazole)iridium.

The materials which make up the layers that form the anode, the cathode and the layers formed therebetween differ according to whether a device having a bottom emission structure or a top emission structure is to be fabricated, and so are suitably selected while taking this into account.

Generally, in an element having a bottom emission structure, a transparent anode is used on the substrate side and light is extracted from the substrate side, whereas in an element having a top emission structure, a reflective anode made of metal is used and light is extracted from a transparent electrode (cathode) in the opposite direction from the substrate. Hence, with regard to the anode material, for example, when fabricating a device having a bottom emission structure, a transparent anode of ITO or the like is used, and when manufacturing a device having a top emission structure, a reflective anode of Al/Nd or the like is used.

The organic EL device of the invention, in order to prevent a deterioration in the device characteristics, may be sealed in the usual manner with, if necessary, a desiccant or the like.

EXAMPLES

Synthesis Examples, Working Examples and Comparative Examples are given below to more concretely illustrate the invention, although the invention is not limited by these Examples. The equipment used was as follows.

| | | |
|---|---|---|
| (1) | $^1$H-NMR Measurement: | 400NB NMR system, from Varian, Inc. |
| (2) | Substrate Cleaning: | Substrate cleaning machine (reduced-pressure plasma system), from Choshu Industry Co., Ltd. |
| (3) | Varnish Coating: | MS-A100 Spin Coater, from Mikasa Co., Ltd. |
| (4) | Measurement of Contact Angle: | Contact angle meter, from Kyowa Interface Science Co., Ltd. |
| (5) | Film Thickness Measurement: | Surfcorder ET-4000 microfigure measuring instrument, from Kosaka Laboratory, Ltd. |
| (6) | Fabrication of Organic EL Device: | C-E2L1G1-N Multifunction Vapor Deposition System, from Choshu Industry Co., Ltd. |
| (7) | Measurement of Organic EL Device Brightness: | I-V-L Measurement System from Tech World, Inc. |
| (8) | Measurement of Organic EL Device Longevity: | PEL-105S Organic EL Brightness Life EvaluationSystem, from EHC K.K. |

[1] Compound Synthesis

[Synthesis Example 1] Synthesis of Amide Compound A

[Chemical Formula 31]

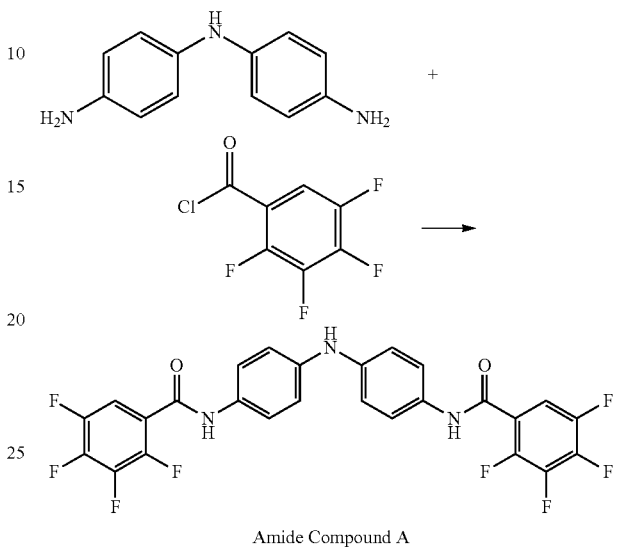

Amide Compound A

A flask was charged with 2.00 g of N1-(4-aminophenyl) benzene-1,4-diamine, 20 mL of toluene and 3.34 mL of triethylamine, following which the flask interior was flushed with nitrogen, 6.36 g of 2,3,4,5-tetrafluorobenzoyl chloride was added dropwise and the system was stirred at room temperature for 2 hours. The reaction mixture was filtered and the resulting filtered matter was dried, after which it was dissolved in N,N-dimethylformamide. The resulting solution was added dropwise to 400 mL of deionized water, following which stirring was carried out at room temperature. The suspension was filtered and the filtered matter thus obtained was dried, giving the target Amide Compound A (yield, 3.82 g). The $^1$H-NMR measurement results are shown below.

$^1$H-NMR (400 MHz, DMSO-d6): 10.43 (s, 2H), 8.18 (s, 1H), 7.73-7.79 (m, 2H), 7.56 (d, J=8.8 Hz, 4H), 7.06 (d, J=8.8 Hz, 4H).

[Synthesis Example 2] Synthesis of Amide Compound B

[Chemical Formula 32]

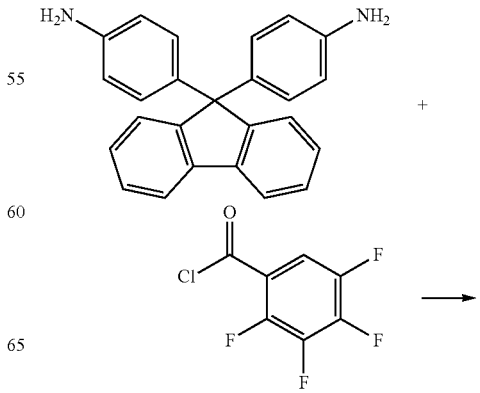

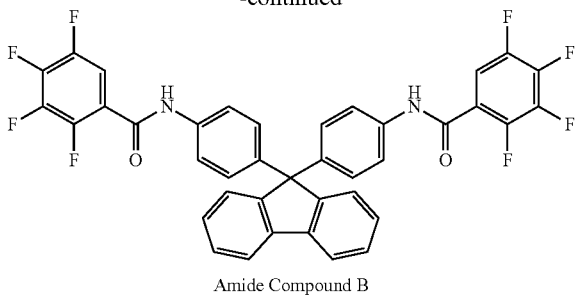

Amide Compound B

A flask was charged with 2.00 g of 4,4'-(9H-fluorene-9,9-diyl)dianiline, 40 mL of toluene and 2.07 mL of triethylamine, following which the flask interior was flushed with nitrogen, 3.01 g of 2,3,4,5-tetrafluorobenzoyl chloride was added dropwise and the system was stirred at room temperature for 4 hours. The reaction mixture was filtered and the resulting filtered matter was dried, after which it was dissolved in N,N-dimethylformamide. The resulting solution was added dropwise to 450 mL of deionized water, following which stirring was carried out at room temperature. The suspension was filtered and the filtered matter thus obtained was dried, giving the target Amide Compound B (yield, 3.81 g). The $^1$H-NMR measurement results are shown below.

$^1$H-NMR (400 MHz, DMSO-d6): 10.58 (s, 2H), 7.91 (d, J=7.6 Hz, 2H), 7.67-7.73 (m, 2H), 7.54 (d, J=8.8 Hz, 4H), 7.44 (d, J=7.6 Hz, 2H), 7.38 (t, J=7.6 Hz, 2H), 7.30 (t, J=7.6 Hz, 2H), 7.09 (d, J=8.8 Hz, 4H).

[Synthesis Example 3] Synthesis of Amide Compound C

[Chemical Formula 33]

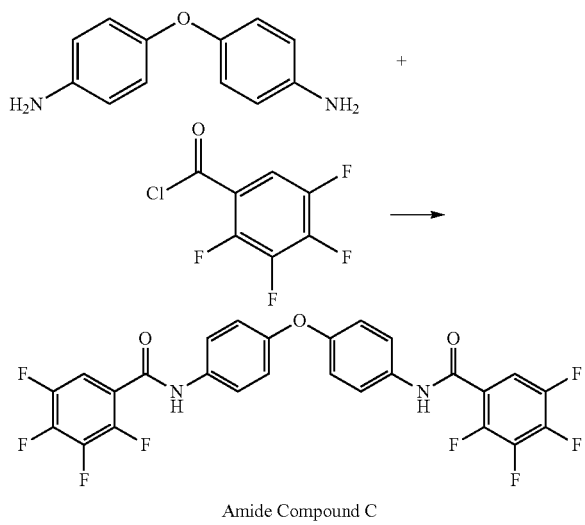

Amide Compound C

A flask was charged with 1.00 g of di(4-aminophenyl) ether, 20 mL of toluene and 1.80 mL of triethylamine, following the flask interior was flushed with nitrogen, 2.59 g of 2,3,4,5-tetrafluorobenzoyl chloride was added dropwise and the system was stirred at room temperature for 2 hours. The reaction mixture was filtered and the resulting filtered matter was dried, after which it was dissolved in N,N-dimethylformamide. The resulting solution was added dropwise to 300 mL of deionized water, following which stirring was carried out at room temperature. The suspension was filtered and the filtered matter thus obtained was dried, giving the target Amide Compound C (yield, 2.04 g). The $^1$H-NMR measurement results are shown below.

$^1$H-NMR (400 MHz, DMSO-d6): 10.60 (s, 2H), 7.72-7.78 (m, 2H), 7.67 (d, J=8.8 Hz, 4H), 7.01 (d, J=8.8 Hz, 4H).

[Synthesis Example 4] Synthesis of Amide Compound D

[Chemical Formula 34]

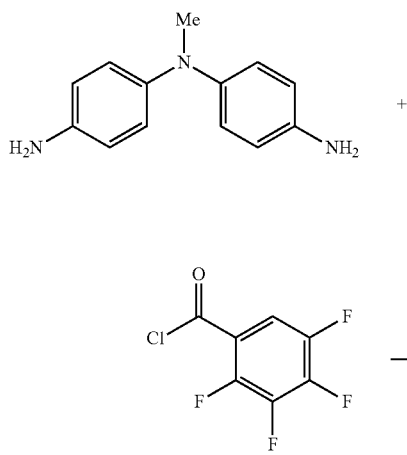

Amide Compound D

A flask was charged with 1.00 g of N1-(4-aminophenyl)-N1-methylbenzene-1,4-diamine, 40 mL of toluene and 1.70 mL of triethylamine, following which the flask interior was flushed with nitrogen, 2.41 g of 2,3,4,5-tetrafluorobenzoyl chloride was added dropwise and the system was stirred at room temperature for 20 hours. The reaction mixture was filtered and the resulting filtered matter was dried, after which it was dissolved in N,N-dimethylformamide. The resulting solution was added dropwise to 250 mL of deionized water, following which stirring was carried out at room temperature. The suspension was filtered and the filtered matter thus obtained was dried, giving the target Amide Compound D (yield, 2.40 g). The $^1$H-NMR measurement results are shown below.

$^1$H-NMR (400 MHz, THF-d8): 9.40 (s, 2H), 7.59-7.65 (m, 6H), 6.99 (d, J=8.8 Hz, 4H), 3.29 (s, 3H).

[Synthesis Example 5] Synthesis of Amide Compound E

[Chemical Formula 35]

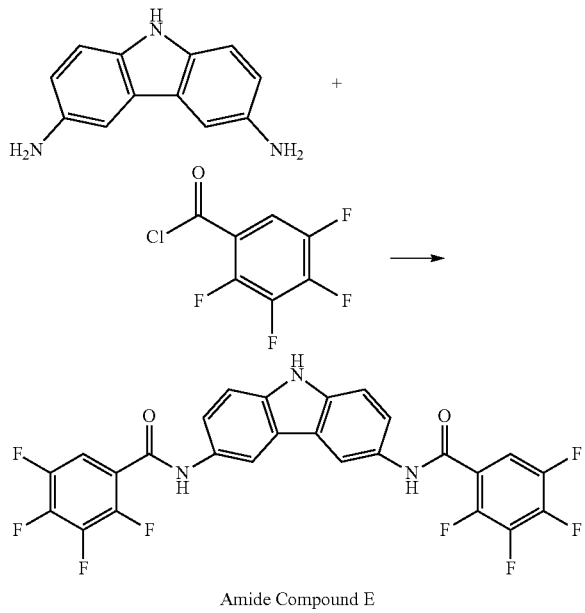

Amide Compound E

A flask was charged with 0.96 g of 9H-carbazole-3,6-diamine, 20 mL of toluene and 1.62 mL of triethylamine, following which the flask interior was flushed with nitrogen, 2.55 g of 2,3,4,5-tetrafluorobenzoyl chloride was added dropwise and the system was stirred at room temperature for 2 hours. The reaction mixture was filtered and the resulting filtered matter was dried, after which it was dissolved in N,N-dimethylformamide. The resulting solution was added dropwise to 250 mL of deionized water, following which stirring was carried out at room temperature. The suspension was filtered and the filtered matter thus obtained was suspended in and washed with isopropanol and then dried, giving the target Amide Compound E (yield, 1.86 g). The $^1$H-NMR measurement results are shown below.

$^1$H-NMR (400 MHz, DMSO-d6): 11.27 (s, 1H), 10.58 (s, 2H), 8.46 (s, 2H), 7.77-7.82 (m, 2H), 7.58 (dd, J=8.8, 2.0 Hz, 2H), 7.45 (d, J=8.8 Hz, 2H).

[Synthesis Example 6] Synthesis of Amide Compound F

[Chemical Formula 36]

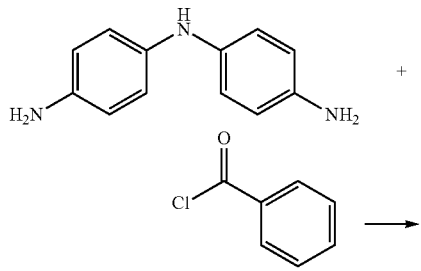

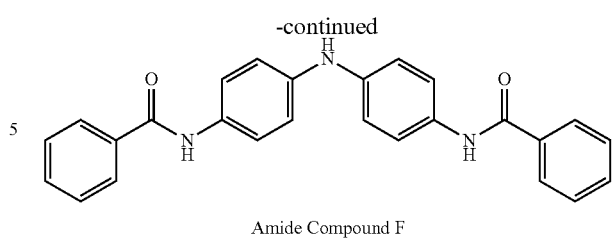

Amide Compound F

A flask was charged with 1.00 g of N1-(4-aminophenyl)benzene-1,4-diamine, 30 mL of toluene and 1.8 mL of triethylamine, following which the flask interior was flushed with nitrogen, 1.70 g of benzoyl chloride was added dropwise and the system was stirred at room temperature for 1 hour. The reaction mixture was filtered and the resulting filtered matter was dried, after which it was dissolved in N,N-dimethylformamide. The resulting solution was added dropwise to 200 mL of deionized water, following which stirring was carried out at room temperature. The suspension was filtered, and the filtered matter thus obtained was washed with ethanol and then dried, giving the target Amide Compound F (yield, 1.46 g). The $^1$H-NMR measurement results are shown below.

$^1$H-NMR (400 MHz, THF-d8): 9.20 (s, 2H), 7.91 (d, J=7.2 Hz, 4H), 7.63 (d, J=7.6 Hz, 4H), 7.40-7.48 (m, 6H), 7.19 (s, 1H), 7.01 (d, J=7.6 Hz, 4H).

[Synthesis Example 7] Synthesis of Aniline Derivative X

[Chemical Formula 37]

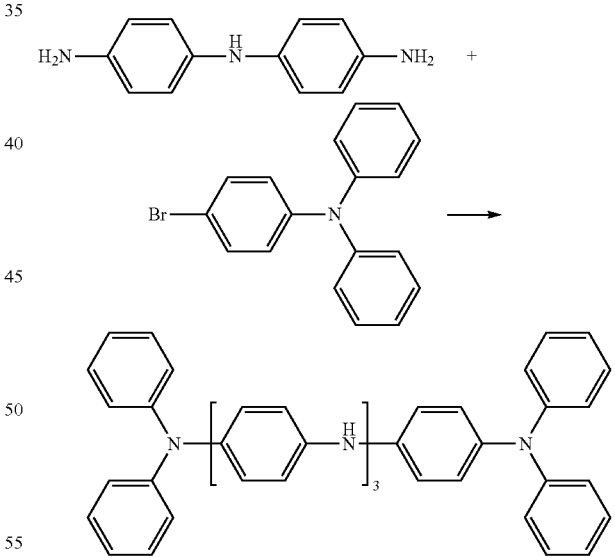

Aniline Derivative X

A flask was charged with 4,4'-diaminodiphenylamine (3.18 g, 16.0 mmol), 4-bromotriphenylamine (11.4 g, 35.2 mmol), Pd(dba)$_2$ (0.185 g, 0.322 mmol) and t-BuONa (3.38 g, 35.2 mmol) and the flask interior was flushed with nitrogen, following which toluene (200 mL) and PhP(t-Bu)$_2$ (0.142 g, 0.639 mmol) were added and the system was stirred at 80° C. for 5 hours. The reaction mixture was cooled to room temperature, following which water was added, thereby stopping the reaction, and the organic layer was separated off by liquid separation. The organic layer was washed with saturated saline water and dried over MgSO$_4$, following which the solvent was distilled off under reduced pressure, giving a crude product. The crude product was purified by silica gel column chromatography (toluene/ethyl acetate), giving the target Aniline Derivative X (yield, 6.83 g).

[2] Preparation of Charge-Transporting Varnishes

[Working Example 1-1] Preparation of Charge-Transporting Varnish A

Charge-Transporting Varnish A was prepared by dissolving 0.051 g of Amide Compound A synthesized in Synthesis Example 1, 0.129 g of Aniline Derivative X synthesized in Synthesis Example 7 and 0.383 g of Arylsulfonic Acid A of the formula shown below, under a nitrogen atmosphere, in a mixed solvent of 6.7 g of 1,3-dimethyl-2-imidazolidinone (DMI), 10 g of cyclohexanol (CHA) and 3.3 g of propylene glycol (PG). Arylsulfonic Acid A was synthesized in accordance with WO 2006/025342.

[Chemical Formula 38]

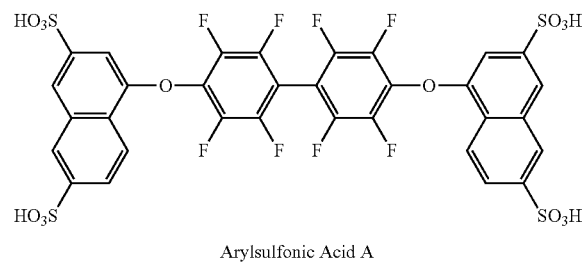

Arylsulfonic Acid A

[Working Example 1-2] Preparation of Charge-Transporting Varnish B

Charge-Transporting Varnish B was prepared by dissolving 0.051 g of Amide Compound B synthesized in Synthesis Example 2, 0.129 g of Aniline Derivative X synthesized in Synthesis Example 7 and 0.383 g of Arylsulfonic Acid A, under a nitrogen atmosphere, in a mixed solvent of 6.7 g of DMI, 10 g of CHA and 3.3 g of PG.

[Working Example 1-3] Preparation of Charge-Transporting Varnish C

Charge-Transporting Varnish C was prepared by dissolving 0.051 g of Amide Compound C synthesized in Synthesis Example 3, 0.129 g of Aniline Derivative X synthesized in Synthesis Example 7 and 0.383 g of Arylsulfonic Acid A, under a nitrogen atmosphere, in a mixed solvent of 6.7 g of DMI, 10 g of CHA and 3.3 g of PG.

[Working Example 1-4] Preparation of Charge-Transporting Varnish D

Charge-Transporting Varnish D was prepared by dissolving 0.051 g of Amide Compound D synthesized in Synthesis Example 4, 0.129 g of Aniline Derivative X synthesized in Synthesis Example 7 and 0.383 g of Arylsulfonic Acid A, under a nitrogen atmosphere, in a mixed solvent of 6.7 g of DMI, 10 g of CHA and 3.3 g of PG.

[Working Example 1-5] Preparation of Charge-Transporting Varnish E

Charge-Transporting Varnish E was prepared by dissolving 0.051 g of Amide Compound E synthesized in Synthesis Example 5, 0.129 g of Aniline Derivative X synthesized in Synthesis Example 7 and 0.383 g of Arylsulfonic Acid A, under a nitrogen atmosphere, in a mixed solvent of 6.7 g of DMI, 10 g of CHA and 3.3 g of PG.

Comparative Example 1-1

Preparation of Charge-Transporting Varnish F

Charge-Transporting Varnish F was prepared by dissolving 0.051 g of Amide Compound F synthesized in Synthesis Example 6, 0.129 g of Aniline Derivative X synthesized in Synthesis Example 7 and 0.383 g of Arylsulfonic Acid A, under a nitrogen atmosphere, in a mixed solvent of 6.7 g of DMI, 10 g of CHA and 3.3 g of PG.

[3] Production of Thin Films and Measurement of Contact Angle.

The contact angle was measured by the following method for the charge-transporting varnishes produced in Working Examples 1-1 to 1-5 and Comparative Example 1.

In each case, the charge-transporting varnish was spin-coated onto an indium-tin oxide (ITO) substrate to form a film, dried in open air at 80° C. on a hot plate for 1 minute and then baked under applied heat at 230° C. for 15 minutes, thereby producing a thin film. The contact angle of cyclohexylbenzene on the resulting thin film was measured. The results are shown in Table 10.

TABLE 10

| | Charge-transporting varnish | Contact angle of cyclohexylbenzene (°) |
|---|---|---|
| Working Example 1-1 | A | 2.8 |
| Working Example 1-2 | B | 2.0 |
| Working Example 1-3 | C | 2.4 |
| Working Example 1-4 | D | 2.2 |
| Working Example 1-5 | E | 3.0 |
| Comparative Example 1 | F | 29.3 |

When the contact angle of the solvent used in the upper layer material is 10° or more, crawling of the upper layer material may occur at the time of deposition, as a result of which a uniform film may not be obtainable. As shown in Table 10, the contact angle of the solvent on the thin film produced from the charge-transporting varnish in Comparative Example 1 is very high, and so there is a risk of the solvent used in the upper layer material being repelled. On the other hand, the contact angle of the solvent on the thin films produced from the charge-transporting varnishes in Working Examples 1-1 to 1-5 which include the fluorine atom-containing amide compound of the invention is 3° or less in each case. Hence it is expected that crawling will not arise at the time of deposition and that the coatability of the upper layer will be good, resulting in formation of the upper layer material into a uniform film.

[4] Device Fabrication and Evaluation of Device Characteristics

In the following Working Examples and Comparative Examples, a glass substrate with dimensions of 25 mm×25 mm×0.7 mm (t) and having ITO patterned on the surface to a film thickness of 150 nm was used as the ITO substrate.

Prior to use, impurities on the surface were removed with an O$_2$ plasma cleaning system (150 W, 30 seconds).

[4-1] Fabrication of Single-Layer Devices (SLD) and Evaluation of Device Characteristics

Working Example 2-1

The varnish obtained in Working Example 1-1 was coated onto an ITO substrate using a spin coater and was subsequently, in open air, pre-baked at 80° C. for 1 minute and then subjected to a main bake at 230° C. for 15 minutes, thereby forming a 40 nm thin film on the ITO substrate.

Next, using a vapor deposition system (degree of vacuum, 4.0×10$^{-5}$ Pa), a thin film of aluminum was deposited thereon, giving a single-layer device. Vapor deposition was carried out at a deposition rate of 0.2 nm/s. The thickness of the aluminum thin film was set to 100 nm.

To prevent the device characteristics from deteriorating due to the influence of oxygen, moisture and the like in air, the SLD was sealed with sealing substrates, following which the characteristics were evaluated. Sealing was carried out by the following procedure.

The SLD was placed between sealing substrates in a nitrogen atmosphere having an oxygen concentration of 2 ppm or less and a dew point of not more than −85° C., and the sealing substrates were laminated together using an adhesive (MORESCO Moisture Cut WB90US(P), from Moresco Corporation). At this time, a desiccant (HD-071010W-40, from Dynic Corporation) was placed, together with the SLD, within the sealing substrates. The laminated sealing substrates were irradiated with UV light (wavelength, 365 nm; dosage, 6,000 mJ/cm$^2$) and then annealed at 80° C. for 1 hour to cure the adhesive.

Working Examples 2-2 to 2-5

Aside from using the varnishes obtained in Working Examples 1-2 to 1-5 instead of the varnish obtained in Working Example 1-1, SLDs were fabricated in the same way as in Working Example 2-1.

Comparative Example 2

Aside from using the varnish obtained in Comparative Example 1 instead of the varnish obtained in Working Example 1-1, an SLD was fabricated in the same way as in Working Example 2-1.

[4-2] Fabrication of Hole-Only Devices (HOD) and Evaluation of Device Characteristics

Working Example 3-1

The varnish obtained in Working Example 1-1 was coated onto an ITO substrate using a spin coater and was subsequently, in open air, pre-baked at 80° C. for 1 minute and then subjected to a main bake at 230° C. for 15 minutes, thereby forming a 40 nm thin film (hole-injecting layer) on the ITO substrate.

Next, using a vapor deposition system (degree of vacuum, 2.0×10 Pa), thin films of α-NPD and aluminum were successively deposited thereon, giving a hole-only device. Vapor deposition was carried out at a deposition rate of 0.2 nm/s. The thicknesses of the α-NPD and aluminum thin films were set to 20 nm and 100 nm, respectively.

To prevent the device characteristics from deteriorating due to the influence of oxygen, moisture and the like in air, the HOD was sealed with sealing substrates, following which the characteristics were evaluated. Sealing was carried out in the same way as described above.

Working Examples 3-2 to 3-5

Aside from using the varnishes obtained in Working Examples 1-2 to 1-5 instead of the varnish obtained in Working Example 1-1, HODs were fabricated in the same way as in Working Example 3-1.

Comparative Example 3

Aside from using the varnish obtained in Comparative Example 1 instead of the varnish obtained in Working Example 1-1, an HOD was fabricated in the same way as in Working Example 3-1.

The current densities at a driving voltage of 3 V were measured for the SLDs and HODs fabricated in the above Working Examples and Comparative Examples. The results are shown in Table 11. In addition, the relative strength of the HOD current density to the SLD current density at the same voltage is also shown. The fact that this relative strength is high indicates that the efficient supply of holes to the hole-transporting layer is being achieved.

TABLE 11

| | Charge-transporting varnish | Current density (mA/cm$^2$) | | HOD/SLD (%) |
|---|---|---|---|---|
| | | SLD | HOD | |
| Working Examples 2-1, 3-1 | A | 2,840 | 1,330 | 46.8 |
| Working Examples 2-2, 3-2 | B | 2,890 | 1,250 | 43.3 |
| Working Examples 2-3, 3-3 | C | 2,970 | 1,210 | 40.7 |
| Working Examples 2-4, 3-4 | D | 2,590 | 1,120 | 43.2 |
| Working Examples 2-5, 3-5 | E | 2,990 | 1,340 | 44.7 |
| Comparative Examples 2, 3 | F | 2,530 | 879 | 34.7 |

As shown in Table 11, devices that used a hole-injecting layer produced from a charge-transporting varnish of the invention, compared with devices fabricated in the Comparative Examples, all had high relative strengths of the HOD current density to the SLD current density.

[4-3] Fabrication of Organic EL Devices and Evaluation of Device Characteristics

Working Example 4-1

The varnish obtained in Working Example 1-1 was coated onto an ITO substrate using a spin coater and then dried at 80° C. for 1 minute and baked in an open-air atmosphere at 230° C. for 15 minutes, thereby forming a uniform 40-nm thin film (hole-injecting layer) on the ITO substrate.

Using a vapor deposition system (degree of vacuum, 2.0×10$^{-5}$ Pa), a 20 nm film of α-NPD was formed thereon at a deposition rate of 0.2 nm/s. CBP and Ir(PPy)$_3$ were then co-vapor deposited. Co-vapor deposition was carried out while controlling the vapor deposition rate so that the Ir(PPy)$_3$ concentration becomes 6%, thereby depositing a 40 nm layer. Next, thin-films of BAlq, lithium fluoride and aluminum were successively deposited, thereby giving an organic EL device. At this time, vapor deposition was carried out at a rate of 0.2 nm/s each for BAlq and aluminum, and at a rate of 0.02 nm/s for lithium fluoride. The thicknesses of the BAlq, lithium fluoride and aluminum thin films were set to respectively 20 nm, 0.5 nm and 100 nm.

To prevent the device characteristics from deteriorating due to the influence of oxygen, moisture and the like in air, the organic EL device was sealed with sealing substrates, following which the characteristics were evaluated. Sealing was carried out in the same way as described above.

Working Example 4-2 to 4-5

Aside from using the varnishes obtained in Working Examples 1-2 to 1-5 instead of the varnish obtained in Working Example 1-1, organic EL devices were fabricated in the same way as in Working Example 4-1.

Comparative Example 4

Aside from using the varnish obtained in Comparative Example 1 instead of the varnish obtained in Working Example 1-1, an organic EL device was fabricated in the same way as in Working Example 4-1.

The voltage, current density, current efficiency and half-life (initial brightness, 5,000 cd/m$^2$) at a brightness of 5,000 cd/m$^2$ were measured for these devices. The results are shown in Table 12. The size of the light-emitting surface on each device was set to a surface area of 2 mm×2 mm.

TABLE 12

| Charge-transporting varnish | Voltage (V) | Current density (mA/cm$^2$) | Current efficiency (cd/A) | Half-life (h) |
|---|---|---|---|---|
| Working Example 4-1 | A | 9.49 | 17.45 | 28.66 | 365 |
| Working Example 4-2 | B | 9.51 | 17.19 | 29.09 | 366 |
| Working Example 4-3 | C | 9.49 | 17.19 | 29.09 | 318 |
| Working Example 4-4 | D | 9.46 | 17.63 | 28.36 | 347 |
| Working Example 4-5 | E | 9.49 | 17.35 | 28.82 | 380 |
| Comparative Example 4 | F | 9.50 | 17.40 | 28.73 | 331 |

As shown in Table 12, compared with the organic EL device obtained in Comparative Example 4, all of the organic EL devices according to the invention had the same degree of driving voltages and current efficiencies, and had similar or better half-lives.

The invention claimed is:

1. A charge-transporting varnish comprising a fluorine atom-containing amide compound of formula (1) below and a charge-transporting substance,

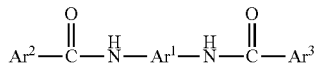
(1)

wherein Ar$^1$ is a group of any of formulas (1-1) to (1-9) below,

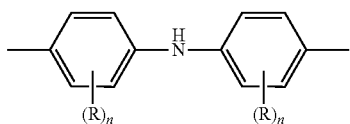
(1-1)

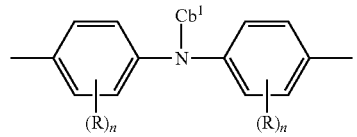
(1-2)

(1-3)

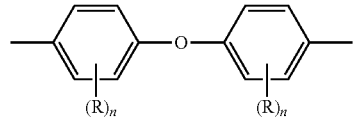
(1-4)

(1-5)

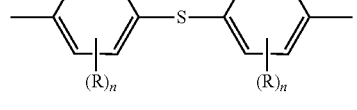
(1-6)

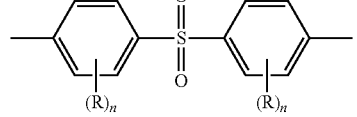
(1-7)

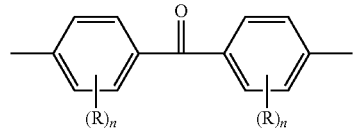
(1-8)

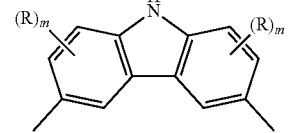

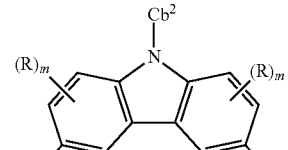
(1-9)

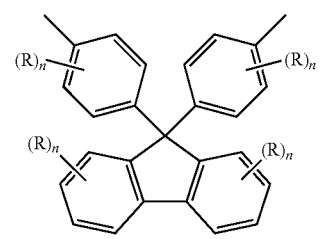

wherein each R is independently a cyano group, a nitro group, a halogen atom, an alkyl group of 1 to 20 carbon atoms or a haloalkyl group of 1 to 20 carbon atoms, Cb$^1$ and Cb$^2$ each are independently an alkyl group of 1 to 20 carbon atoms or an aryl group of 6 to 20 carbon atoms, n is an integer from 0 to 4, and m is an integer from 0 to 3; and Ar$^2$ and Ar$^3$ are each independently a fluoroaryl group of 6 to 20 carbon atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms;

an aryl group of 6 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms; a fluoroaralkyl group of 7 to 20 carbon atoms which may be substituted with a cyano group, a chlorine atom, a bromine atom, an iodine atom, a nitro group, a fluoroalkoxy group of 1 to 20 carbon atoms, a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms; or an aralkyl group of 7 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms.

2. The charge-transporting varnish of claim 1, wherein $Ar^2$ and $Ar^3$ are each independently a fluoroaryl group of 6 to 20 carbon atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or an aryl group of 6 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms.

3. The charge-transporting varnish of claim 2, wherein $Ar^2$ and $Ar^3$ are each independently a phenyl group which is substituted with three or more fluorine atoms and may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or a 2-(trifluoromethyl)phenyl, 3-(trifluoromethyl)phenyl, 4-(trifluoromethyl)phenyl, 4-ethoxy-3-(trifluoromethyl)phenyl, 3-fluoro-4-trifluoromethylphenyl, 4-fluoro-3-trifluoromethylphenyl, 4-fluoro-2-trifluoromethylphenyl, 2-fluoro-5-(trifluoromethyl)phenyl, 3-fluoro-5-(trifluoromethyl)phenyl, 3,5-di(trifluoromethyl)phenyl, 2,4,6-tri(trifluoromethyl)phenyl, 4-(pentafluoroethyl)phenyl, 4-(3,3,3-trifluoropropyl)phenyl, 2,3,5,6-tetrafluoro-4-trifluoromethylphenyl, 4-(perfluorovinyl)phenyl, 4-(perfluoropropenyl)phenyl or 4-(perfluorobutenyl)phenyl group.

4. The charge-transporting varnish of any one of claims 1 to 3, wherein $Ar^2$ and $Ar^3$ are identical groups.

5. The charge-transporting varnish of claim 1, wherein n and m are both 0.

6. The charge-transporting varnish of claim 1, wherein $Ar^1$ is a group of formula (1-1), (1-2), (1-3), (1-7) or (1-9).

7. The charge-transporting varnish of claim 1, further comprising a dopant.

8. A charge-transporting thin film produced using the charge-transporting varnish of claim 1.

9. An organic electroluminescent device comprising the charge-transporting thin film of claim 8.

10. A fluorine atom-containing amide compound of formula (1′) below,

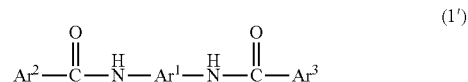

(1′)

wherein $Ar^1$ is a group of any of formulas (1-1) to (1-9) below,

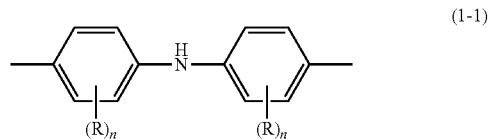

(1-1)

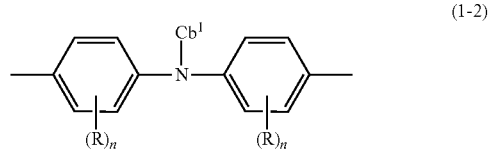

(1-2)

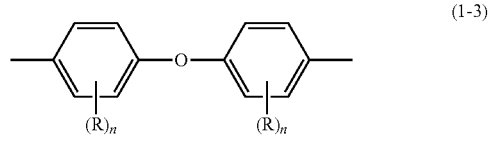

(1-3)

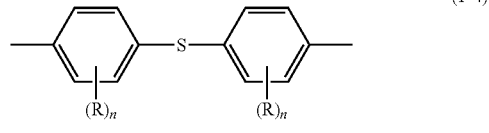

(1-4)

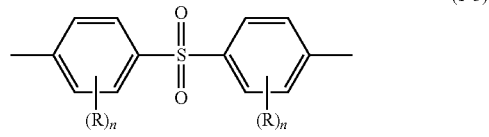

(1-5)

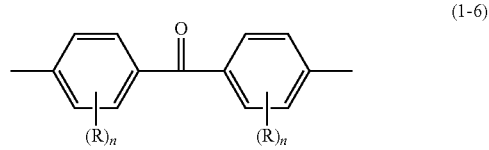

(1-6)

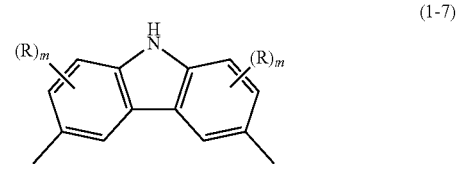

(1-7)

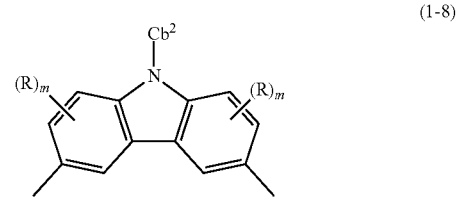

(1-8)

-continued

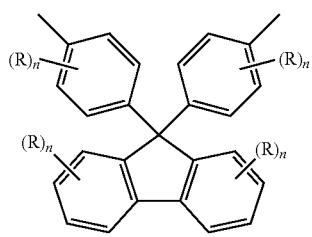
(1-9)

wherein each R is independently a cyano group, a nitro group, a halogen atom, an alkyl group of 1 to 20 carbon atoms or a haloalkyl group of 1 to 20 carbon atoms, $Cb^1$ and $Cb^2$ each are independently an alkyl group of 1 to 20 carbon atoms or an aryl group of 6 to 20 carbon atoms, n is an integer from 0 to 4, and m is an integer from 0 to 3; and $Ar^2$ and $Ar^3$ are each independently a fluoroaryl group of 6 to 20 carbon atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; an aryl group of 6 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms; a fluoroaralkyl group of 7 to 20 carbon atoms which may be substituted with a cyano group, a chlorine atom, a bromine atom, an iodine atom, a nitro group, a fluoroalkoxy group of 1 to 20 carbon atoms, a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms; or an aralkyl group of 7 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms;

exclusive of combinations that represent fluorine atom-containing amide compounds of any of formulas (K1) to (K18) below:

(K1)
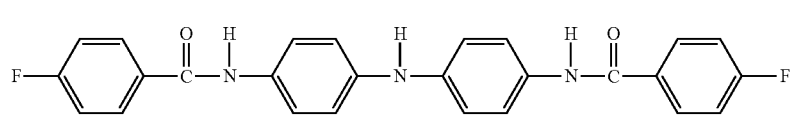

(K2)
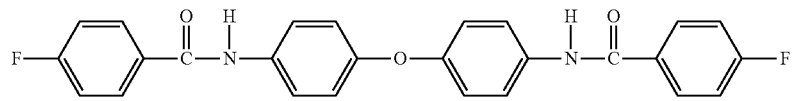

(K3) (K4)
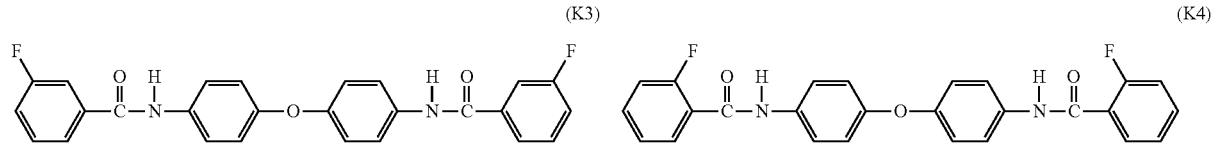

(K5)
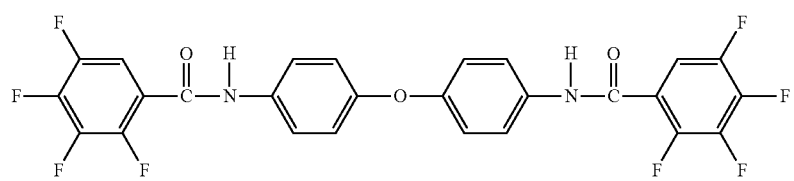

(K6)
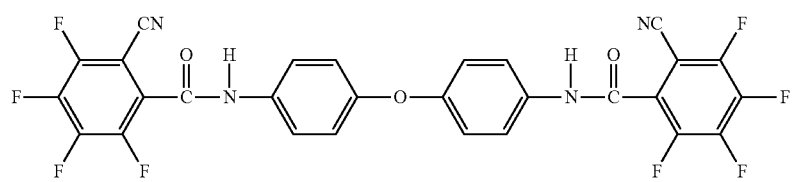

(K7)
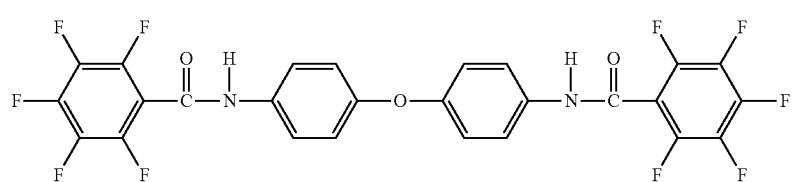

(K8)
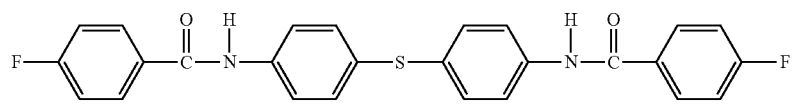
(K9)
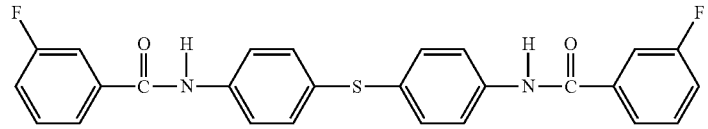
(K10)
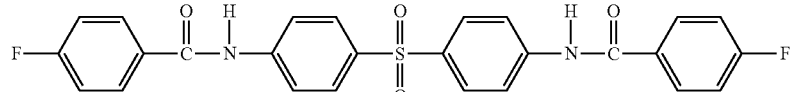
(K11)
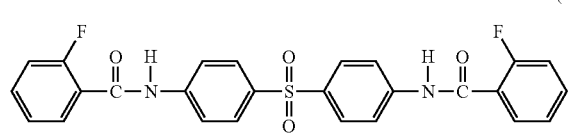
(K12)
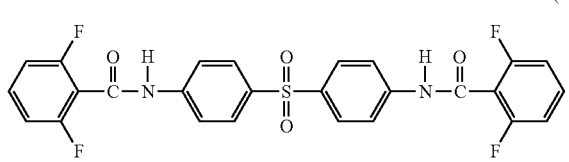
(K13)
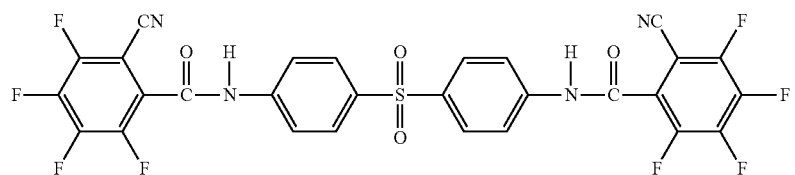
(K14)
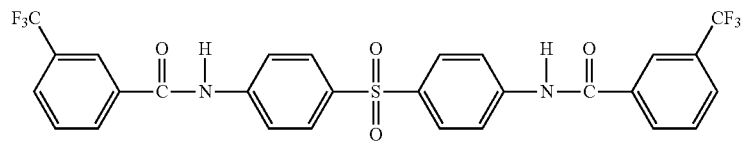
(K15)
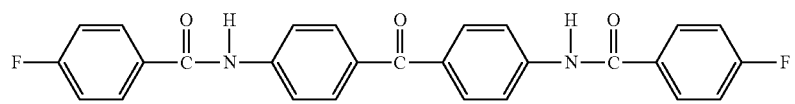
(K16)
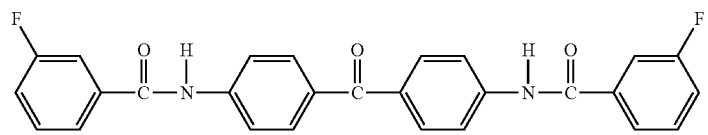
(K17)
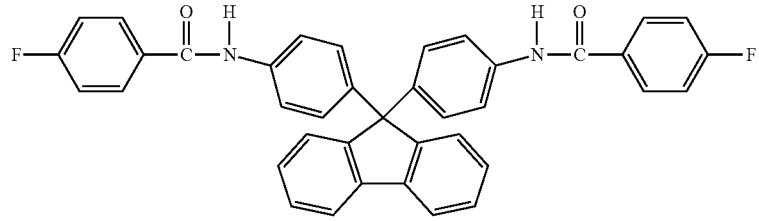
(K18)
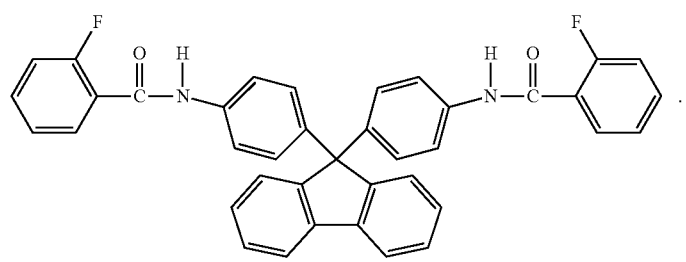

11. The fluorine atom-containing amide compound of claim 10, wherein $Ar^2$ and $Ar^3$ are each independently a fluoroaryl group of 6 to 20 carbon atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or an aryl group of 6 to 20 carbon atoms which is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, and which may be additionally substituted with a cyano group, a halogen atom or a fluoroalkoxy group of 1 to 20 carbon atoms.

12. The fluorine atom-containing amide compound of claim 11, wherein $Ar^2$ and $Ar^3$ are each independently a phenyl group which is substituted with three or more fluorine atoms and may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or a 2-(trifluoromethyl)phenyl, 3-(trifluoromethyl)phenyl, 4-(trifluoromethyl)phenyl, 4-ethoxy-3-(trifluoromethyl)phenyl, 3-fluoro-4-trifluoromethylphenyl, 4-fluoro-3-trifluoromethylphenyl, 4-fluoro-2-trifluoromethylphenyl, 2-fluoro-5-(trifluoromethyl)phenyl, 3-fluoro-5-(trifluoromethyl)phenyl, 3,5-di(trifluoromethyl)phenyl, 2,4,6-tri(trifluoromethyl)phenyl, 4-(pentafluoroethyl)phenyl, 4-(3,3,3-trifluoropropyl)phenyl, 2,3,5,6-tetrafluoro-4-trifluoromethylphenyl, 4-(perfluorovinyl)phenyl, 4-(perfluoropropenyl)phenyl or 4-(perfluorobutenyl)phenyl group.

13. The fluorine atom-containing amide compound of any one of claims 10 to 12, wherein $Ar^2$ and $Ar^3$ are identical groups.

14. The fluorine atom-containing amide compound of claim 10, wherein n and m are both 0.

15. The fluorine atom-containing amide compound of claim 10, wherein $Ar^1$ is a group of formula (1-1), (1-2), (1-3), (1-7) or (1-9).

* * * * *